(12) United States Patent
Kim et al.

(10) Patent No.: US 9,394,553 B2
(45) Date of Patent: Jul. 19, 2016

(54) **BIOSYNTHETIC GENE CLUSTER FOR CHEJUENOLIDE OF MARINE MICROORGANISM *HAHELLA CHEJUENSIS***

(71) Applicant: KOREA UNIVERSITY RESEARCH AND BUSINESS FOUNDATION, Seoul (KR)

(72) Inventors: Beom Seok Kim, Seoul (KR); Hyuncheol Oh, Busan (KR); Bee-Gek Ng, Seoul (KR); Jae-Woo Han, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 0 days.

(21) Appl. No.: 14/380,696

(22) PCT Filed: Dec. 14, 2012

(86) PCT No.: PCT/KR2012/010879
§ 371 (c)(1),
(2) Date: Dec. 2, 2014

(87) PCT Pub. No.: WO2013/125777
PCT Pub. Date: Aug. 29, 2013

(65) Prior Publication Data
US 2015/0203883 A1 Jul. 23, 2015

(30) Foreign Application Priority Data

Feb. 24, 2012 (KR) ........................ 10-2012-0019271

(51) Int. Cl.
| | |
|---|---|
| *C12P 17/06* | (2006.01) |
| *C12N 9/10* | (2006.01) |
| *C07D 309/32* | (2006.01) |
| *C12N 15/52* | (2006.01) |
| *C12P 13/02* | (2006.01) |

(52) U.S. Cl.
CPC .............. *C12P 17/06* (2013.01); *C07D 309/32* (2013.01); *C12N 9/1029* (2013.01); *C12N 15/52* (2013.01); *C12P 13/02* (2013.01)

(58) Field of Classification Search
CPC ...... C12N 9/1029; C12N 15/52; C12P 17/06; C12P 13/02; C07D 309/32
USPC ............................................... 435/252.3, 125
See application file for complete search history.

(56) References Cited

U.S. PATENT DOCUMENTS 4,914,206 A 4/1990 Minamida et al.

FOREIGN PATENT DOCUMENTS

| | | |
|---|---|---|
| CN | 1014050 B | 9/1991 |
| EP | 0226896 B1 | 9/1993 |
| JP | 62-240687 A | 10/1987 |
| JP | 2006/296419 A | 11/2006 |
| KR | 10-0661175 B1 | 12/2006 |
| WO | 2007/073011 A1 | 6/2007 |

OTHER PUBLICATIONS

Choi, Y. H., et al., "Chejuenolides A and B, new macrocyclic tetraenes from the marine bacterium *Hahella chejuensis*", Tetrahedron Letters, 2008, vol. 49, pp. 7128-7131.
Seo, et al., "Chejuenolide C: A New Macrocyclic Metabolite from the Marine Bacterium *Hahella chejuensis*", Korean Chem. Soc., 2009, vol. 30, No. 5, pp. 1181-1183.
GenBank YP_434661.1, "Polyketide synthase modules-like protein [*Hahella chejuensis* KCTC 2396]", Jun. 10, 2013.
GenBank YP_434646.1, "Amino acid ABC transporter periplasmic protein [*Hahella chejuensis* KCTC 2396]", Jun. 10, 2013.
GenBank YP_434654.1, "Major facilitator superfamily permease [*Hahella chejuensis* KCTC 2396]", Jun. 10, 2013.
GenBank YP_434309.1, "Transcriptional regulator [*Hahella chejuensis* KCTC 2396]", Jun. 10, 2013.
GenBank YP_434311.1, "Xaa-Pro aminopeptidase [*Hahella chejuensis* KCTC 2396]", Jun. 10, 2013.
GenBank CP000155.1, "*Hahella chejuensis* KCTC 2396, complete genome", Jan. 31, 2014.
International Search Report dated Apr. 12, 2013 of PCT/KR2012/010879 which is the parent application—6 pages.
Aparicio, et al., "Organization from the biosynthetic gene cluster for rapamycin in *Streptomyces hygroscopicus*: analysis of the enzymatic domains in the modular polyketide synthase", Elsevier Science B.V., 1996, pp. 9-16, vol. 169.
Arakawa, et al., "Cyclization Mechanism for the Synthesis of Macrocyclic Antibiotic Lankacidin in *Streptomyces rochei*", Chemistry & Biology, 2005, pp. 249-256, vol. 12.
Cortes, et al., Repositioning of a Domain in a Modular Polyketide Synthase to Promote Specific Chain Cleavage, Science Magazine, Jun. 1995, pp. 1487-1489, vol. 268.
Dickschat, et al., "An Additional Dehydratase-Like Activity is Required for Lankacidin Antibiotic Biosynthesis", ChemBioChem, Sep. 2011, pp. 2408-2412, vol. 12.
Donadio, et al., "Organization of the enzymatic domains in the multifunctional polyketide synthase involved in erythromycin formation in *Saccharopolyspora erythraea*", Elsevier Science Publishers, 1992, pp. 51-60, vol. 111.
Fenical, et al., "Developing a new resource for drug discovery: marine actinomycete bacteria", Nature Chemical Biology, Dec. 2006, pp. 666-673, vol. 2, No. 12.

(Continued)

*Primary Examiner* — Younus Meah
(74) *Attorney, Agent, or Firm* — Knobbe Martens Olson & Bear LLP

(57) ABSTRACT

The present invention relates to a biosynthetic gene cluster for a chejuenolide of the marine microorganism *Hahella chejuensis*, and to the function of an enzyme involving the biosynthetic pathway of a chejuenolide encoded by the genes. Since the present invention can be applied to the development of a novel material as a mechanism for biosynthesis by combining of biosynthetic genes for chejuenolide, the present invention can suggest a new direction in the study of polyketide antibiotics, and is thus very useful.

6 Claims, 4 Drawing Sheets

(56) References Cited

OTHER PUBLICATIONS

Gokhale, et al., "Dissecting and Exploiting Intermodular Communication in Polyketide Synthases", Science Magazine, Apr. 1999, pp. 482-485, vol. 284.

Harada, "Studies on Lankacidin-Group (T-2636) Antibiotics. VI. Chemical Structures of Lankacidin-Group Antibiotics. II", Chemical and Pharmaceutical Bulletin, 1975, pp. 2201-2210, vol. 23, No. 10.

Harada, et al., "Studies on Lankacidin-Group (T-2636) Antibiotics. V. Chemical Structures of Lankacidin-Group Antibiotics. I", Chemical and Pharmaceutical Bulletin, pp. 99-108, vol. 22, No. 1.

Harada, et al., "Studies on Lankacidin-Group (T-2636) Antibiotics VIII. Metabolism of Lankacidin C 14-Propionate in Rats and Mice", The Journal of Antibiotics, Nov. 1973, pp. 658-668, vol. 26, No. 11.

Hayashi, et al., "In Vitro and In Vivo Activities of Sedecamycin against Treponema hyodysenteriae", American Society for Microbiology, Apr. 1988, pp. 458-461, vol. 32, No. 4.

Higashide, et al., "Taxonomy of *Streptomyces rochei* Var. *Volubilis* Var. Nov. and Production of the Antibiotics and an Esterase", The Journal of Antibiotics, Jan. 1971, pp. 1-12, vol. 24, No. 1.

Hutchinson, "Polyketide Synthase Gene Manipulation: A Structure-Function Approach in Engineering Novel Antibiotics", Annual Reviews in Microbiology, 1995, pp. 201-238, vol. 49.

Jacobsen, et al., "Precursor-Directed Biosynthesis of Erythromycin Analogs by an Engineered Polyketide Synthase", Science Magazine, Jul. 1997, pp. 367-369, vol. 277.

Katz, "Manipulation of Modular Polyketide Synthases", American Chemical Society, 1997, pp. 2557-2575, vol. 97.

Kennedy, et al., "Modulation of Polyketide Synthase Activity by Accessory Proteins During Lovastatin Biosynthesis", Science Magazine, May 1999, pp. 1368-1372, vol. 284.

MacNeil, et al., "Complex organization of the *Streptomyces avermitilis* genes encoding the avermectin polyketide synthase*", Elsevier Science Publishers B.V., 1992, pp. 119-125, vol. 115.

Marris, "Drugs from the Deep", Nature Publishing Group, Oct. 2006, pp. 904-905, vol. 443.

McDaniel, et al., "Multiple genetic modifications of the erythromycin polyketide synthase to produce a library of novel "unnatural" natural products", Applied Biological Sciences, Mar. 1999, pp. 1846-1851, vol. 96.

Menzella, et al., Combinatorial polyketide biosynthesis by de novo design and rearrangement of modular polyketide synthase genes, Nature Biotechnology, Sep. 2005, pp. 1171-1176, vol. 23, No. 9.

Muller, "Don't Classify Polyketide Synthases", Chemistry & Biology, Jan. 2004, pp. 4-6, vol. 11.

Oliynyk, et al., "A hybrid modular polyketide synthase obtained by domain swapping", Chemistry & Biology, 1996, pp. 833-839, vol. 3, No. 10.

Shen, "Polyketide biosynthesis beyond the type I, II and III polyketide synthase paradigms", Current Opinion in Chemical Biology, 2003, pp. 285-295, vol. 7.

Staunton, et al., "Polyketide biosynthesis: a millennium review", The Royal Society of Chemistry, 2001, pp. 380-416, vol. 18.

Tatsuno, et al., "Analysis of Modular-iterative Mixed Biosynthesis of Lankacidin by Heterologous Expression and Gene Fusion", Journal of Antibiotics, 2007, pp. 700-708, vol. 60, No. 11.

Tatsuno, et al., "Extensive Mutational Analysis of Modular-Iterative Mixed Polyketide Biosynthesis of Lankacidin in *Streptomyces rochei*" Biochemistry, 2009, pp. 2712-2719, vol. 73, No. 12.

Uramoto et al., "The Structures of Bundlin A (Lankacidin) and Bundlin B", Tetrahedron Letters, 1969, pp. 2249-2254, vol. 27.

Oostu et al., "Antitumor and Immunosuppressive Activities of Lankacidin-Group Antibiotics: Structure-Activity Relationships", Cancer Chemotherapy Reports, 1975, vol. 59, No. 5, pp. 919-928.

BIOSYNTHETIC GENE CLUSTER FOR CHEJUENOLIDE OF MARINE MICROORGANISM *HAHELLA CHEJUENSIS*

TECHNICAL FIELD

The present invention relates to a biosynthetic gene cluster for chejuenolide that is a polyketide macrolide-based natural substance. More particularly, the present invention relates to isolated DNAs encoding enzymes associated with a biosynthetic pathway for a chejuenolide, and the function of a gene product associated with the production of chejuenolide. Also, the present invention relates to a mutant strain in which genes and enzymes associated with the biosynthesis of chejuenolide are disrupted, a linear polyketide that is a chejuenolide precursor for biosynthesizing the mutant strain, and a method of preparing the same.

BACKGROUND ART

Marine organisms have attracted attention as an important source for development of new medicines. In particular, marine microorganisms have been known to produce secondary metabolites having various structures and activities. The marine microorganisms often produce natural bioactive substances different from the species found in land environments as the biochemical metabolisms in the body are adapted to marine environments (salinity, a pressure, a high-concentration halogen, etc.) which are completely different from the land environments (Fenical and Jensen 2006; Marris 2006).

New 17-membered carbocyclic tetraene natural substances, chejuenolides A, B and C, have been found from a culture extract of a marine microorganism *Hahella chejuensis* MB-1084 isolated from a marine sediment within the intertidal region in coastal waters of Geojedo Island (Choi, Sohn et al. 2008; Seo and Oh 2009). Only an antibiotic, lankacidin, isolated from *Streptomyces greseofuscus, S. violaceoniger*, and *S. rochei* var. *volubilis* was previously reported as the antibiotic containing a 17-membered carbocyclic ring (Uramoto, Otake et al. 1969; Higashide, Fugono et al. 1971). Lankacidin is a very powerful antibacterial agent that is currently used to treat an infection of *Serpulina* (*Treponema*) *hyodysenteriae* that is a type of bacteria called a spirochete causing diseases in animals and also known to have an anticancer activity and an immunosuppressive effect (Oostu, Matsumoto et al. 1975; Hayashi, Suenaga et al. 1988). Lankacidin have various kinds of analogs (some analogs are also referred to as T-2636 or bundlins). In this case, lankacidin C and chejuenolide highly resemble each other in a structural aspect (Harada and Kishi 1974; Harada 1975; Nakahama, Harada et al. 1975). However, the lankacidin is different from the chejuenolide in that the lankacidin has a 6-membered-δ-lactone ring structure in a 17-membered macrocyclic ring and a 2-hydroxy-propanamide chain at a $3^{rd}$ carbon atom (Harada and Kishi 1974; Harada 1975; Choi, Sohn et al. 2008). It was reported that δ-lactone rings are disrupted as the metabolites, lankacyclinol and lankacyclinol A (12-O-acetyl lankacyclinol), obtained after administration of lankacidin C into rats undergo a decarboxylation action, but a macrolide-based polyketide natural substance having a 17-membered carbocyclic tetraene residue without a 6-membered-δ-lactone ring (deficient in ester bonds) is only a chejuenolide (Harada, Tanayama et al. 1973; Choi, Sohn et al. 2008).

The polyketide-based natural substance is one of the secondary metabolites from the microorganisms which are of medicinal importance, and belong to the antibiotics (tetracycline, erythromycin A, rifamycin S, etc.), the anticancer drugs (daunorubicin, epothilone, etc.), the cholesterol lowering agents (lovastatin, etc.), the anthelminthics (Avermectin, etc.), the antimicrobial drugs (Amphotericin B, etc.), the pesticides (Spinosy A, etc.), and the immunosuppressive drugs (rapamycin, FK506, etc.) (Staunton and Weissman 2001; Shen 2003).

A polyketide is biosynthesized by several simple condensation reactions of carboxylic acid by a polyketide synthase (PKS), a pathway of which is similar to the biosynthesis pathway of fatty acid (Shen 2003; Muller 2004). Type I polyketide is biosynthesized by type I PKS that is a huge multifunctional enzyme, one protein of which shows various enzymatic activities. In this case, such a PKS complex is composed of several modules associated with consecutive condensation reactions (Gokhale, Tsuji et al. 1999; Muller 2004). Each of the modules is composed of acyl transferase (AT), acyl carrier protein (ACP) and β-ketoacyl synthase (KS) domains, which are directly associated with the condensation reaction of carboxylic acid, and ketone reductase (KR), dehydratase (DH) and enoyl reductase (ER) domains which are associated with the reduction of β-ketone groups produced as a result of the condensation reaction (Kennedy, Auclair et al. 1999). The type of carboxylic acid that is an extension unit used in each condensation reaction is widely determined according to the characteristics of the AT domains of each module, a level of reduction of β-ketone groups produced as a result of the condensation reaction varies according to the presence of the reduction domains (KR, DH, and ER) in each module, and the length of the polyketide chain is determined according to the total number of the modules (Donadio and Katz 1992; MacNeil, Occi et al. 1992; Aparicio, Molnar et al. 1996). That is, polyketides having various structures may be biosynthesized according to the combinations of the respective modules and domains. In this aspect, PKS has become an important study subject for combinatorial biosynthesis in addition to a non-ribosomal peptide synthetase (NRPS; a peptide synthetase that is not synthesized in the ribosomes) (Cortes, Wiesmann et al. 1995; Hutchinson and Fujii 1995; Oliynyk, Brown et al. 1996; Jacobsen, Hutchinson et al. 1997; Katz 1997; McDaniel, Thamchaipenet et al. 1999; Menzella, Reid et al. 2005).

The marine microorganism *H. chejuensis* biosynthesizes a polyketide chejuenolide having a peculiar 17-membered macrocyclic structure. When enzymes contributing to the biosynthesis pathway of chejuenolide, and genes encoding the enzymes are elucidated and then applied to development of novel materials as a mechanism for combinatorial biosynthesis, there is a high probability of addressing the new directionality to studies of polyketide-based antibiotics. As the prior-art technique of the present invention, Korean Registered Patent No. 10-0661175 (Dec. 22, 2006) discloses an algicidal preparation including prodigiosin and a prodigiosin biosynthetic gene cluster, and Japanese Unexamined Patent Laid-open Publication No. JP P2006-296419A (Nov. 2, 2006) discloses a method for producing an antibiotic-producing microorganism by gene disruption and the resultant antibiotic-producing microorganism and a method for producing an antibiotic metabolic intermediate (Wnashi Y. and Arakawa K. (2006).). Also, U.S. Pat. No. 4,914,206 (Apr. 3, 1900) discloses lankacidin derivatives and a production method thereof (Minamida. I. and Hashimoto N. (1993) Lankacidin derivatives and production thereof; JP62240687 (Oct. 21, 1987), U.S. Pat. No. 4,914,206 (Apr. 3, 1990), CN1014050 (Jun. 20, 1993), and EP00226896 (Sep. 15, 1993)). However, the isolated gene cluster required to biosynthesize a chejuenolide, and the functions of enzymes encoded by the gene cluster remains to be elucidated.

PRIOR-ART DOCUMENTS

Patent Documents

Korean Registered Patent No. 10-0661175 (Dec. 22, 2006)
Japanese Unexamined Patent Laid-open Publication No. JP P2006-296419A (Nov. 2, 2006)
U.S. Registered Patent No. 04914206 (Apr. 3, 1900)

Non-patent Documents

Arakawa, K., F. Sugino, et al. (2005). "Cyclization mechanism for the synthesis of macrocyclic antibiotic lankacidin in *Streptomyces* rochei." Chem. Biol. 12(2): 249-256.
Choi, Y. H., J. H. Sohn, et al. (2008). "Chejuenolides A and B, new macrocyclic tetraenes from the marine bacterium *Hahella chejuensis*." Tetrahedron Lett. 49 (50): 7128-7131.
Dickschat, J. S., O. Vergnolle, et al. (2011). "An Additional Dehydratase-Like Activity is Required for Lankacidin Antibiotic Biosynthesis." ChemBioChem 12 (16): 2408-2412.
Seo, C. and H. Oh (2009). "Chejuenolide C: A New Macrocyclic Metabolite from the Marine Bacterium *Hahella chejuensis*." Bull. Korean Chem. Soc. 30(5): 1181-1183.
Tatsuno, S., K. Arakawa, et al. (2007). "Analysis of modular-iterative mixed biosynthesis of lankacidin by heterologous expression and gene fusion." J. Antibiot. 60(11): 700-708.
Tatsuno, S., K. Arakawa, et al. (2009). "Extensive mutational analysis of modular-iterative mixed polyketide biosynthesis of lankacidin in *Streptomyces* rochei." Biosci. Biotechnol. Biochem. 73(12): 2712-2719.

DISCLOSURE

Technical Problem

The present inventors cloned a chejuenolide biosynthetic gene from a marine microorganism *Hahella chejuensis* and sequenced the chejuenolide biosynthetic gene. Therefore, the present invention has been completed based on these facts.

Therefore, an object of the present invention provides DNA sequences of genes encoding respective proteins associated with the biosynthesis of a chejuenolide from *H. chejuensis*.

Another object of the present invention provides a method of preparing a chejuenolide mutant using a mutant strain in which one or more of the genes having the DNA sequences are deleted or inactivated.

However, the other objects and advantages of the present invention will become more apparent to those of ordinary skill in the art by describing in detail exemplary embodiments thereof.

Technical Solution

According to one aspect of the present invention, there is provided a biosynthetic gene cluster for an isolated chejuenolide having a DNA sequence set forth in SEQ ID NO: 1.

According to another aspect of the present invention, there is provided a protein having amino acid sequences set forth in SEQ ID NOS: 2 to 27 encoded by the biosynthetic gene cluster.

According to still another aspect of the present invention, there is provided an isolated gene encoding the protein having amino acid sequences set forth in SEQ ID NOS: 2 to 27.

According to still another aspect of the present invention, there is provided a gene encoding a protein having at least one amino acid sequence selected from the group consisting of the followings:

(a) a polyketide synthesis module protein having an amino acid sequence set forth in at least one selected from the group consisting of SEQ ID NO: 6, SEQ ID NO: 7, SEQ ID NO: 10, SEQ ID NO: 11, SEQ ID NO: 12, and SEQ ID NO: 13;

(b) an amine oxidase having an amino acid sequence set forth in SEQ ID NO: 9;

(c) an ABC transporter membrane permease, a transmembrane protein, an ABC transporter periplasmic protein, or an ABC transporter ATPase having an amino acid sequence set forth in at least one selected from the group consisting of SEQ ID NO: 2, SEQ ID NO: 3, SEQ ID NO: 4, SEQ ID NO: 5, SEQ ID NO: 19, SEQ ID NO: 20, SEQ ID NO: 21, SEQ ID NO: 22, and SEQ ID NO: 23;

(d) a transcriptional regulatory enzyme having an amino acid sequence set forth in SEQ ID NO: 14 or SEQ ID NO: 26; and (e) an isochorismatase, a haloacid dehalogenase, an aminopeptidase, or a NADPH-quinone reductase having an amino acid sequence set forth in at least one selected from the group consisting of SEQ ID NO: 8, SEQ ID NO: 15, SEQ ID NO: 24 and SEQ ID NO: 25.

According to still another aspect of the present invention, there is provided a vector containing at least one of the genes.

According to still another aspect of the present invention, there is provided a microorganism transformed with the vector.

According to still another aspect of the present invention, there is provided a method of preparing a chejuenolide, which includes culturing the microorganism.

According to still another aspect of the present invention, there is provided a transformant microorganism for producing a chejuenolide or a precursor thereof in which one or more of genes encoding proteins having amino acid sequences set forth in SEQ ID NOS: 2 to 27 are disrupted, wherein the transformant microorganism includes a chejuenolide biosynthetic gene set forth in SEQ ID NO: 1 in the genome thereof.

According to still another aspect of the present invention, there is provided a chejuenolide precursor O3P2 represented by the following Formula 1

[Formula 1]

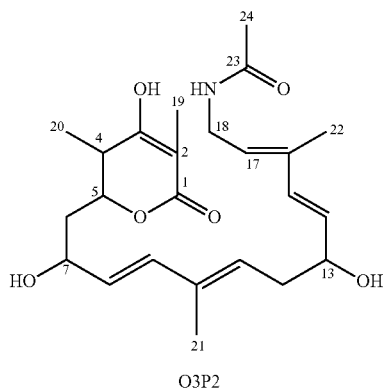

O3P2

According to yet another aspect of the present invention, there is provided a method of preparing a precursor of chejuenolide. Here, the method includes culturing a *H. chejuensis* mutant strain in which a $20,900^{th}$ to $19,482^{nd}$ region (orf3)

encoding the amine oxidase in the DNA sequence set forth in SEQ ID NO: 1 is deleted or inactivated.

Hereinafter, the present invention will be described in detail.

The present invention provides a set of isolated nucleic acid molecules required to biosynthesize a chejuenolide. According to one exemplary embodiment of the present invention, the nucleic acid molecules represent a cluster of biosynthetic genes for a chejuenolide isolated from *H. chejuensis* sp. MB-1084, and are selected from an adjacent DNA sequence (SEQ ID NO: 1) consisting of 26 open reading frames (ORFs) encoding enzymes required for the chejuenolide formation (see FIG. 1). Amino acid sequences of the enzymes encoded by the 26 ORFs are set forth in SEQ ID NOS: 2 to 27, respectively.

Therefore, according to one aspect of the present invention, there is provided a biosynthetic gene cluster for an isolated chejuenolide having a DNA sequence set forth in SEQ ID NO: 1.

According to another aspect of the present invention, there is provided a protein having amino acid sequences set forth in SEQ ID NOS: 2 to 27 encoded by the biosynthetic gene cluster.

According to still another aspect of the present invention, there is provided an isolated gene encoding the protein having amino acid sequences set forth in SEQ ID NOS: 2 to 27.

According to still another aspect of the present invention, there is provided a gene encoding a protein having at least one amino acid sequence selected from the group consisting of the followings:

(a) a polyketide synthesis module protein having an amino acid sequence set forth in at least one selected from the group consisting of SEQ ID NO: 6, SEQ ID NO: 7, SEQ ID NO: 10, SEQ ID NO: 11, SEQ ID NO: 12, and SEQ ID NO: 13;

(b) an amine oxidase having an amino acid sequence set forth in SEQ ID NO: 9;

(c) an ABC transporter membrane permease, a transmembrane protein, an ABC transporter periplasmic protein, or an ABC transporter ATPase having an amino acid sequence set forth in at least one selected from the group consisting of SEQ ID NO: 2, SEQ ID NO: 3, SEQ ID NO: 4, SEQ ID NO: 5, SEQ ID NO: 19, SEQ ID NO: 20, SEQ ID NO: 21, SEQ ID NO: 22, and SEQ ID NO: 23;

(d) a transcriptional regulatory enzyme having an amino acid sequence set forth in SEQ ID NO: 14 or SEQ ID NO: 26; and (e) an isochorismatase, a haloacid dehalogenase, an aminopeptidase, or a NADPH-quinone reductase having an amino acid sequence set forth in at least one selected from the group consisting of SEQ ID NO: 8, SEQ ID NO: 15, SEQ ID NO: 24 and SEQ ID NO: 25.

According to one exemplary embodiment, the gene encoding the protein in group (a) may have DNA sequences set forth in a $11,776^{th}$ to $8,576^{th}$ region (orfA) of SEQ ID NO: 1, a $18,803^{rd}$ to $11,766^{th}$ region (orf1) of SEQ ID NO: 1, a $21,800^{th}$ to $20,919^{th}$ region (orf4) of SEQ ID NO: 1, a $27,598^{th}$ to $21,863^{rd}$ region (orf5) of SEQ ID NO: 1, a $28,462^{nd}$ to $27,605^{th}$ region (orf6) of SEQ ID NO: 1, and a $33,473^{rd}$ to $28,431^{st}$ region (orf7) of SEQ ID NO: 1.

The gene encoding the protein in group (b) may have a DNA sequence set forth in a $20,900^{th}$ to $19,482^{nd}$ region (orf3) of SEQ ID NO: 1.

The gene encoding the protein in group (c) may have DNA sequences set forth in a $8,507^{th}$ to $7,212^{th}$ region (orfB) of SEQ ID NO: 1, a $6,300^{th}$ to $2,431^{st}$ region (orfC) of SEQ ID NO: 1, a $2,082^{nd}$ to $1,327^{th}$ region (orfD) of SEQ ID NO: 1, a $1,071^{st}$ to $307^{th}$ region (orfE) of SEQ ID NO: 1, a $39,788^{th}$ to $41,404^{th}$ region (orf13) of SEQ ID NO: 1, a $41,488^{th}$ to $42,408^{th}$ region (orf14) of SEQ ID NO: 1, a $42,517^{th}$ to $43,350^{th}$ region (orf15) of SEQ ID NO: 1, a $43,445^{th}$ to $44,410^{th}$ region (orf16) of SEQ ID NO: 1, and a $44,435^{th}$ to $45,430^{th}$ region (orf17) of SEQ ID NO: 1.

The gene encoding the protein in group (d) may have DNA sequences set forth in a $34,641^{st}$ to $35,405^{th}$ region (orf8) of SEQ ID NO: 1, and a $48,357^{th}$ to $49,250^{th}$ region (orf20) of SEQ ID NO: 1.

The gene encoding the protein in group (e) may have DNA sequences set forth in a $19,469^{th}$ to $18,915^{th}$ region (orf2) of SEQ ID NO: 1, a $36,205^{th}$ to $35,576^{th}$ region (orf9) of SEQ ID NO: 1, a $45,557^{th}$ to $47,344^{th}$ region (orf18) of SEQ ID NO: 1, and a $48,233^{rd}$ to $47,682^{nd}$ region (orf19) of SEQ ID NO: 1.

According to one exemplary embodiment, each of the isolated nucleic acid molecules according to one exemplary embodiment of the present invention may include a combination of the ORFs selected from orfA to orfE and orf1 to orf21 (SEQ ID NOS: 2 to 27, respectively), which are required to biosynthesize the polyketide chain of the chejuenolide.

According to another exemplary embodiment, each of the nucleic acid molecules according to one exemplary embodiment of the present invention may include a combination of the ORFs selected from orfA to orfE and orf1 to orf21 (SEQ ID NOS: 2 to 27, respectively), which encode enzymes required to extend the polyketide chain of the chejuenolide.

According to still another exemplary embodiment, each of the nucleic acid molecules according to one exemplary embodiment of the present invention may include a combination of the ORFs selected from orfA to orfE and orf1 to orf21 (SEQ ID NOS: 2 to 27, respectively), which encode enzymes required to terminate the extension of the polyketide chain of the chejuenolide and cyclize the polyketide chain of the chejuenolide.

According to still another exemplary embodiment, each of the nucleic acid molecules according to one exemplary embodiment of the present invention may include a combination of the ORFs selected from orfA to orfE and orf1 to orf21 (SEQ ID NOS: 2 to 27, respectively), which encode enzymes required to transport the chejuenolide to the outside and have a tolerance to the chejuenolide.

According to still another exemplary embodiment, each of the nucleic acid molecules according to one exemplary embodiment of the present invention may include a combination of the ORFs selected from orfA to orfE and orf1 to orf21 (SEQ ID NOS: 2 to 27, respectively), which encode enzymes required to regulate expression of the enzymes for biosynthesizing a chejuenolide.

According to yet another exemplary embodiment, each of the nucleic acid molecules including at least one DNA segment selected from SEQ ID NO: 1, which promote an expression level of the ORFs selected from orfA to orfE and orf1 to orf21 (SEQ ID NOS: 2 to 27, respectively) are provided.

The present inventors appreciate that the present invention providing the nucleic acid sequences encoding the enzymes associated with the chejuenolide biosynthesis also provides nucleic acid bases encoding fragments derived from such enzymes. In addition, the present inventors appreciate that the same enzymes set forth in SEQ ID NOS: 2 to 27 may be encoded by nucleic acid sequences rather than the nucleic acid sequences of natural or artificial variants of the orfA to orfE and the orf1 to orf21, that is, the nucleic acid sequences of the genomes, which encode the same enzymes but are set forth in the orfA to orfE and the orf1 to orf21, due to the degeneracy of the genetic code. Also, the present inventors appreciate that the variants having the same function(s) as the original enzymes but including additions, deletions or substitutions of amino acids which are not essential to the folding or functions, or conservative substitutions of essential amino acids may occur as the naturally occurring or artificially constructed variants of the enzymes set forth in SEQ ID NOS: 2 to 27.

Also, the present inventors appreciate that the present invention providing the entire nucleic acid sequence of the cluster required to biosynthesize a chejuenolide also provide a nucleic acid sequence required for expression of the genes present in the cluster. A non-limiting example of such a regulatory sequence includes a promoter and enhancer sequence, an antisense sequence, and a transcription terminator and semi-terminator sequence. Such sequences are useful in regulating the expression of the genes present in the chejuenolide gene cluster. Cells having the nucleotide sequence alone or fused with another nucleotide sequence also fall within the scope of the present invention.

Further, the present invention provides orfA (SEQ ID NO: 6) encoding a polyketide synthesis module including ketosynthase-acyl carrier protein-thioesterase (KS-ACP-TE) domains that extend a polyketide chain by means of a condensation reaction and release the extended polyketide chain by means of a hydrolysis or cyclization procedure, orf1 (SEQ ID NO: 7) encoding a polyketide synthesis module having two pairs of the ketone reductase-ketosynthase-acyl carrier protein (KR-KS-ACP) domains that extend a polyketide chain by means of a condensation reaction and reduce a β-ketone residue of the extended polyketide chain, or orf2 (SEQ ID NO: 8) encoding an enzyme, isochorismatase, that catalyze hydrolysis of isochorismate into 2,3-dihydroxy-2,3-dihydrobenzoate. Also, the present invention provides orf3 (SEQ ID NO: 9) encoding an amine oxidase that oxidize an amine group. In addition, the present invention provides orf4 (SEQ ID NO: 10) encoding a polyketide synthesis module having one acyl transferase (AT) domain providing a malonyl-co-enzyme A (malonyl-CoA) required to extend a polyketide, orf5 (SEQ ID NO: 11) encoding a polyketide synthesis module having ketone reductase-transmethylase-acyl carrier protein1-acyl carrier protein2-ketosynthase (KR-MT-ACP1-ACP2-KS) domains that condense a polyketide chain, reduce the condensed polyketide chain and add one methyl molecule derived from methionine to the polyketide chain, orf6 (SEQ ID NO: 12) encoding a polyketide synthesis module having one dehydratase (DH) domain useful in removing one molecule of water from a β-hydroxyl group during extension of the polyketide to form a double bond between α- and β-carbon atoms, or orf7 (SEQ ID NO: 13) encoding an NRPS-PKS hybrid module coding for condensase-adenylase-peptidyl carrier protein-ketosynthase (C-A-PCP-KS) domains that condense one molecule of glycine with one molecule of malonyl-co-enzyme A during polyketide biosynthesis, or an isolated nucleic acid molecule having a nucleic acid sequence encoding a naturally occurring variant or derivative of the enzyme.

Further, the present invention provides a nucleic acid molecule having a nucleic acid sequence encoding an enzyme encoded by at least one selected from the group consisting of orfB to orfE and orf13 to orf17 (SEQ ID NOS: 2 to 5 and SEQ ID NOS:19 to 23, respectively), which are useful in transporting a chejuenolide or a chejuenolide precursor from cells to the outside and giving tolerance to the chejuenolide or chejuenolide precursor, an enzyme encoded by at least one selected from the group of orf8 and orf20 (SEQ ID NOS: 14 and 26, respectively), which directly or indirectly permit or activate biosynthesis and expression of tolerance-related genes during preparation of the chejuenolide, an enzyme encoded by at least one selected from the group consisting of orf9, orf18 and orf19 (SEQ ID NOS: 15, 24 and 25, respectively), which are considered to indirectly participate in biosynthesis pathway of the chejuenolide, or a naturally occurring or artificially constructed variant or derivative of the enzyme.

According to still another aspect of the present invention, there are provided a vector including the gene, a microorganism transformed with the vector, and a method of preparing chejuenolide, which includes culturing the microorganism.

According to still another aspect of the present invention, there is provided a transformant microorganism for producing a chejuenolide or a precursor thereof which includes a chejuenolide biosynthetic gene set forth in SEQ ID NO: 1 in the genome thereof and in which one or more of genes encoding proteins having amino acid sequences set forth in SEQ ID NOS: 2 to 27 are disrupted. Preferably, the microorganism is a mutant strain *H. chejuensis* O3KO (International Accession No.: KCTC 12315BP; and Korean Accession No. KACC91712P) in which a gene encoding an amine oxidase in the DNA sequence set forth in SEQ ID NO: 1 is disrupted.

According to one exemplary embodiment, there may be provided a chejuenolide-producing strain having extra copies of the nucleic acid sequence specifying one ORF selected from the group consisting of orfA to orfE and orf1 to orf21 (SEQ ID NOS: 2 to 27, respective).

According to preferred exemplary embodiments, such a chejuenolide-producing strain is any strain belonging to the *Oceanospirillales* order. According to other preferred exemplary embodiments, such a chejuenolide-producing strain is a family of the *Hahella* genus. According to one additional aspect of the present invention, there is provided a *Hahella* strain having one or more modifications in the nucleic acid sequence set forth in SEQ ID NO: 1, which results in increased or decreased expression of one or more of orfA to orfE and orf1 to orf21 (SEQ ID NOS: 2 to 27, respectively).

According to one preferred exemplary embodiment, the present invention provides a nucleic acid molecule having a nucleic acid sequence set forth in SEQ ID NO: 1 or a partial region thereof, which contains at least one vector, wherein the nucleic acid molecule is useful in preparing at least one of a chejuenolide and a precursor thereof, or a derivative of the chejuenolide in other cells. According to preferred exemplary embodiments, the nucleic acid sequence or partial region thereof is included in a single vector. According to other preferred exemplary embodiments, such a vector is a bacterial artificial chromosome (BAC).

Also, the present invention provides a knockout cassette and a knockout vector, both of which includes at least one selected from the group consisting of a gene orfA having a thioesterase domain positioned at the end of the polyketide synthase cluster among the 26 ORFs, a gene orfB encoding a membrane permease, genes orfC and orfD downstream of the orfB, genes orf8, orf9 and orf19 upstream of a gene orf7 encoding a polyketide/peptide hybrid synthesis module, and genes orf2 and orf3 accompanied in a PKS-related gene cluster forming the backbone of a chejuenolide.

Specifically, the present invention provides various pairs of DNA knockout cassettes in which at least one selected from a thioesterase domain in the polyketide synthesis module designated as the orfA positioned at the end of the polyketide synthase cluster, a membrane permease designated as the orfB positioned downstream of the polyketide synthase cluster, a transmembrane protein designated as the orfC, an isochorismatase designated as the orf2 positioned inside the polyketide synthase cluster, an amine oxidase designated as the orf3, a transcriptional regulatory enzyme designated as the orf8 positioned upstream of the polyketide synthase cluster, a haloacid dehalogenase designated as the orf9, and a NADPH-quinone reductase designated as the orf19 is substituted with an antibiotic apramycin-resistant gene (see Table 2). PCR primers having a sequence of 36 nucleic acid bases tailored immediately upstream and downstream of the initiation codon and the stop codon of each of the above-described genes are constructed to amplify an apramycin-resistant gene cassette consisting of an antibiotic-resistant gene and an origin of transfer (OriT) gene (FIG. 2). The amplified DNA fragment serves as a knockout cassette. Then, the knockout cassette may be used to construct a knockout vector in which the antibiotic-resistant gene and ORF are optionally substituted (FIG. 2). For this purpose, a PCR targeting approach (Gust, Challis et al. 2003) is used, but various approaches may be applied.

The present invention provides a knockout cassette including at least one selected from the group consisting of the thioesterase domain, the membrane permease, the transmembrane protein, the isochorismatase, the amine oxidase, the transcriptional regulator, and the dehalogenasor NADPH-quinone reductase gene.

According to specific exemplary embodiments of the present invention, there are provided a pBG6E11-derived knockout vector in which each of the transcriptional regulator, dehalogenase, NADPH-quinone reductase, isochorismatase and amine oxidase genes constructed as the knockout cassette are substituted with the antibiotic-resistant gene, and a pBG19A6-derived knockout vector derived in which the thioesterase, membrane permease or transmembrane protein gene is substituted with the antibiotic-resistant gene.

In addition, the present invention provide gene mutant strains in which at least one selected from the group consisting of the thioesterase domain, the membrane permease, the transmembrane protein, the isochorismatase, the amine oxidase, the transcriptional regulator, and the dehalogenasor NADPH-quinone reductase genes is disrupted, wherein the gene mutant strains are transformed by means of conjugation between *Escherichia coli* and a heterogeneous bacterial strain using the knockout vectors (FIG. 2).

When *H. chejuensis* is transformed using the knockout vector according to one exemplary embodiment of the present invention, the DNA sequences upstream and downstream of the ORF substituted with the antibiotic-resistant gene in the knockout vector have the same DNA sequence as chromosomal DNA, resulting in induction of a homologous recombination event. A mutant strain in which the ORF is optionally disrupted by means of the homologous recombination is prepared (FIG. 2).

The present inventors extracted secondary metabolites from the *H. chejuensis* mutant strain using a liquid-liquid chromatography technique, and finally examined an effect of the disrupted genes and enzymes on biosynthesis of a chejuenolide using high-performance liquid chromatography (HPLC) and mass spectrometry (MS).

Among the mutant strains constructed through a series of procedures, a *H. chejuensis* mutant strain O3KO in which the amine oxidase is 기 disrupted was deposited (International Accession No.: KCTC 12315BP; and Korean Accession No. KACC91712P). In this case, a compound produced by the mutant strain O3KO is a linear polyketide O3P2 (Formula: $C_{24}H_{35}NO_6$) that is a chejuenolide precursor represented by the following Formula 1.

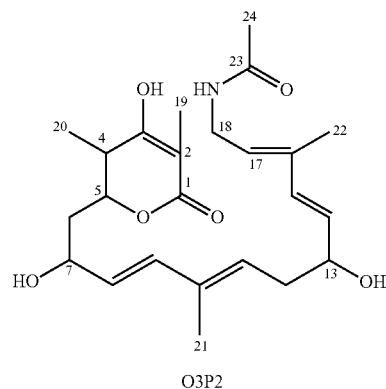

[Formula 1]

O3P2

Furthermore, the present invention provides a method of preparing the gene-disrupted mutant strain, a method of producing a linear polyketide, and a linear polyketide produced using the method.

More particularly, the present invention provides a method of preparing a precursor of a chejuenolide, which includes culturing a *H. chejuensis* mutant strain in which a $20,900^{th}$ to $19,482^{nd}$ region (orf3) encoding the amine oxidase in the DNA sequence set forth in SEQ ID NO: 1 is deleted or inactivated (Gust, B., G. L. Challis, et al. (2003). "PCR-targeted *Streptomyces* gene replacement identifies a protein domain needed for biosynthesis of the sesquiterpene soil odor geosmin." Proceedings of the National Academy of Sciences 100 (4): 1541.)

A. Chejuenolide Biosynthetic Gene from *H. chejuensis*

A chejuenolide is a polyketide macrolide-based natural metabolite produced by a marine microorganism *H. chejuensis* MB-1084. The present invention provides a nucleic acid sequence of a gene cluster for biosynthesis of a chejuenolide, and enzymes. A physical hierarchy of the chejuenolide gene cluster is shown together with an adjacent DNA sequence in FIG. 1. FIG. 1 shows a physical map of a nucleic acid molecule having a length of 51.4 kb from the chromosomal DNA of *H. chejuensis*, and a set of fosmids specifying such a segment. A genetic hierarchy of the DNA segments governing the chejuenolide biosynthesis is shown in FIG. 1, and a nucleic acid sequence of the genetic construct is set forth in SEQ ID NO: 1.

An exact boundary of the cluster may be constructed through comparison with another biosynthetic gene cluster for a polyketide, particularly comparison with another biosynthetic gene cluster for a 17-membered carbocyclic tetraene antibiotic lankacidin, and the functions of a gene product of the another biosynthetic gene cluster. Therefore, as shown in the left end of FIG. 1, the chejuenolide cluster is demarked by a gene orfE (SEQ ID NO: 2) encoding an amino acid ABC transporter periplasmic protein having a width spanning from a $1,071^{st}$ residue to a $307^{th}$ residue of the nucleic acid sequence set forth in SEQ ID NO: 1. As shown in the right end of FIG. 1, the chejuenolide cluster is demarked by the remainder of ORF whose functions are not known and which has a width spanning from a $49,530^{th}$ residue to a $50,609^{th}$ residue of the nucleic acid sequence set forth in SEQ ID NO: 1. The chejuenolide cluster includes 26 ORFs which have a width of approximately 51,400 base pairs and are set forth in orfA to orfE and orf1 to orf21, respectively.

The nucleic acid sequence set forth in SEQ ID NO: 1 encodes 26 enzymes set forth in SEQ ID NOS: 2 to 27, respectively. The orfE (SEQ ID NO: 2) represents a sequence of 254 amino acid residues derived by translating a 1,071st to 307$^{th}$ nucleic acid sequence on the complementary double helix. The orfD (SEQ ID NO: 3) represents a sequence of 251 amino acid residues derived by translating a 2,082$^{nd}$ to 1,327$^{th}$ nucleic acid sequence on the complementary double helix. The orfC (SEQ ID NO: 4) represents a sequence of 1,269 amino acid residues derived by translating a 6,300$^{th}$ to 2,431$^{st}$ nucleic acid sequence on the complementary double helix. The orfB (SEQ ID NO: 5) represents a sequence of 431 amino acid residues derived by translating a 8,507$^{th}$ to 7,212$^{th}$ nucleic acid sequence on the complementary double helix. The orfA (SEQ ID NO: 6) represents a sequence of 1,066 amino acid residues derived by translating a 11,776$^{th}$ to 8,576$^{th}$ nucleic acid sequence on the complementary double helix. The orf1 (SEQ ID NO: 7) represents a sequence of 2,345 amino acid residues derived by translating a 18,803$^{rd}$ to 11,766$^{th}$ nucleic acid sequence on the complementary double helix. The orf2 (SEQ ID NO: 8) represents a sequence of 184 amino acid residues derived by translating a 19,469$^{th}$ to 18,915$^{th}$ nucleic acid sequence on the complementary double helix. The orf3 (SEQ ID NO: 9) represents a sequence of 472 amino acid residues derived by translating a 20,900$^{th}$ to 19,482$^{nd}$ nucleic acid sequence on the complementary double helix. The orf4 (SEQ ID NO: 10) represents a sequence of 293 amino acid residues derived by translating a 21,800$^{th}$ to 20,919$^{th}$ nucleic acid sequence on the complementary double helix. The orf5 (SEQ ID NO: 11) represents a sequence of 1,911 amino acid residues derived by translating a 27,598$^{th}$ to 21,863$^{rd}$ nucleic acid sequence on the complementary double helix. The orf6 (SEQ ID NO: 12) represents a sequence of 285 amino acid residues derived by translating a 28.462$^{nd}$ to 27,605$^{th}$ nucleic acid sequence on the complementary double helix. The orf7 (SEQ ID NO: 13) represents a sequence of 1,680 amino acid residues derived by translating a 33,473$^{rd}$ to 28,431$^{st}$ nucleic acid sequence on the complementary double helix. The orf8 (SEQ ID NO: 14) represents a sequence of 254 amino acid residues derived by translating a 34,641$^{st}$ to 35,405$^{th}$ nucleic acid sequence on the complementary double helix. The orf9 (SEQ ID NO: 15) represents a sequence of 209 amino acid residues derived by translating a 36,205$^{th}$ to 35,576$^{th}$ nucleic acid sequence on the complementary double helix. The orf10 (SEQ ID NO: 16) represents a sequence of 147 amino acid residues derived by translating a 37,230$_{th}$ to 36,787$^{th}$ nucleic acid sequence on the complementary double helix. The orf11 (SEQ ID NO: 17) represents a sequence of 158 amino acid residues derived by translating a 38,496$^{th}$ to 38,020$^{th}$ nucleic acid sequence on the complementary double helix. The orf12 (SEQ ID NO: 18) represents a sequence of 126 amino acid residues derived by translating a 38,963$^{rd}$ to 38,583$^{rd}$ nucleic acid sequence on the complementary double helix. The orf13 (SEQ ID NO: 19) represents a sequence of 538 amino acid residues derived by translating a 39,788$^{th}$ to 41,404$^{th}$ nucleic acid sequence on the complementary double helix. The orf14 (SEQ ID NO: 20) represents a sequence of 306 amino acid residues derived by translating a 41,488$^{th}$ to 42,408$^{th}$ nucleic acid sequence on the complementary double helix. The orf15 (SEQ ID NO: 21) represents a sequence of 277 amino acid residues derived by translating a 42,517$^{th}$ to 43,350$^{th}$ nucleic acid sequence on the complementary double helix. The orf16 (SEQ ID NO: 22) represents a sequence of 321 amino acid residues derived by translating a 43,445$^{th}$ to 44,410$^{th}$ nucleic acid sequence on the complementary double helix. The orf17 (SEQ ID NO: 23) represents a sequence of 331 amino acid residues derived by translating a 44,435$^{th}$ to 45,430$^{th}$ nucleic acid sequence on the complementary double helix. The orf18 (SEQ ID NO: 24) represents a sequence of 595 amino acid residues derived by translating a 45,557$^{th}$ to 47,344$^{th}$ nucleic acid sequence on the complementary double helix. The orf19 (SEQ ID NO: 25) represents a sequence of 183 amino acid residues derived by translating a 48,233$^{rd}$ to 47,682$^{nd}$ nucleic acid sequence on the complementary double helix. The orf20 (SEQ ID NO: 26) represents a sequence of 297 amino acid residues derived by translating a 48,357$^{th}$ to 49,250$^{th}$ nucleic acid sequence on the complementary double helix. The orf21 (SEQ ID NO: 27) represents a sequence of 359 amino acid residues derived by translating a 49,530$^{th}$ to 50,609$^{th}$ nucleic acid sequence on the complementary double helix.

The biosynthetic gene cluster for the chejuenolide is summarized in the following Table 1.

TABLE 1

| Chejuenolide cluser | | | Lke cluster[a] | | Gene bank[b] | | | |
|---|---|---|---|---|---|---|---|---|
| | DNA sequence | | Size | | Volume | | | |
| ORF[c] | Start | End | (bp) | Gene | match[d] | Entry[e] | Error[f] | Proposed function[g] | CD[h] |
| orfB | 1071 | 307 | 765 | | | YP_434645.1 | 3e-170 | Amino acid ABC transporter periplasmic protein | Bacterial periplasmic substrate binding protein |
| orfD | 2082 | 1927 | 756 | | | YP_434646.1 | 2e-174 | Amino acid ABC transporter periplasmic protein | Bacterial periplasmic substrate binding protein |
| orfC | 6300 | 2431 | 3870 | | | ZP_1696941.1 | 0.0 | Transmembrane protein | G8 domain-VCBS repeat |
| orfB | 8507 | 7212 | 1295 | orf20 | 53% | YP_434654.1 | 0.0 | Membrane permease | MFS carrier |
| orfA | 11776 | 8576 | 3201 | LkeG | 51% | YP_434655.1 | 0.0 | Polyketide synthesis module | KS-ACP-TB |
| orf1 | 18803 | 11766 | 7038 | LkeF | 49% | YP_434656.1 | 0.0 | Polyketide synthesis module | KR1-ACP1-KS1-KR2-ACP2-KS2 |
| orf2 | 19469 | 18915 | 555 | LkeH | 51% | YP_434657.1 | 6e-131 | Nicotinamidase-like enzyme | Isochorismatase |
| orf3 | 20900 | 19482 | 1419 | LkeE | 63% | YP_434658.1 | 0.0 | Amine oxidase | Amine oxidase |
| orf4 | 21800 | 20919 | 882 | LkeD | 54% | YP_434659.1 | 0.0 | Acyl transferase | AT |
| orf5 | 27598 | 21863 | 5735 | LkeC | 54% | YP_434660.1 | 0.0 | Polyketide synthesis module | KR-MT-ACP1-ACP2-Ks |
| orf6 | 28452 | 27605 | 858 | LkeB | 50% | YP_434661.1 | 0.0 | Dehydratase | DH |
| orf7 | 33473 | 28431 | 5043 | LkeA | 49% | YP_434662.1 | 0.0 | Polyketide/peptide hybrid synthesis module | C-A-PCP-KS |
| orf8 | 34641 | 35405 | 755 | | | ZP_8991191.1 | 0.0 | Transcriptional regulatory enzyme | |
| orf9 | 36205 | 35576 | 630 | | | YP_3807586.1 | 2e-70 | Haloacid dehalogenase | Haloacid dehalogenase-like enzyme |
| orf10 | 37230 | 36787 | 444 | | | YP_1518378.1 | 0.001 | Unknown | |
| orf11 | 38496 | 38020 | 477 | | | YP_434319.1 | 3e-103 | Unknown | |

TABLE 1-continued

| | Chejuenolide cluser | | | Lke cluster[a] | | Gene bank[b] | | |
|---|---|---|---|---|---|---|---|---|
| | DNA sequence | | Size | | Volume | | | |
| ORF[c] | Start | End | (bp) | Gene | match[d] | Entry[e] | Error[f] | Proposed function[g] | CD[h] |
| orf12 | 38953 | 38569 | 381 | | | YP_434318.1 | 2e-77 | Unknown | |
| orf13 | 39733 | 41404 | 1617 | | | YP_434316.1 | 0.0 | Oligopeptide ABC transporter periplasmic protein | Oligopeptide ABC transporter periplasmic protein |
| orf14 | 41499 | 42408 | 921 | | | YP_434315.1 | 0.0 | Dipeptide/oligopeptide/Ni ABC transporter membrane permease | Dipeptide/oligopeptide/Ni ABC transporter membrane permease |
| orf15 | 42517 | 48350 | 834 | | | YP_434314.1 | 0.0 | Dipeptide/oligopeptide/Ni ABC transporter membrane permease | Dipeptide/oligopeptide/Ni ABC transporter membrane permease |
| orf16 | 43445 | 44410 | 966 | | | YP_434313.1 | 0.0 | Dipeptide/oligopeptide/Ni ABC transporter ATPase | Dipeptide/oligopeptide/Ni ABC transporter ATPase |
| orf17 | 44435 | 45430 | 996 | | | YP_434312.1 | 0.0 | Oligopeptide ABC transporter ATPase | Oligopeptide ABC transporter ATPase |
| orf18 | 45557 | 47344 | 1788 | | | YP_434311.1 | 0.0 | Aminopeptidase | Xaa-Pro aminopeptidase |
| orf19 | 48233 | 47682 | 552 | | | YP_434310.1 | 0.0 | NADPH-quinone reductase | NADPH-quinone reductase |
| orf20 | 48357 | 49250 | 894 | | | YP_434309.1 | 0.0 | Transcriptional regulatory enzyme | Transcriptional regulatory enzyme |
| orf21 | 49530 | 50609 | 1083 | | | YP_390605.1 | 0.0 | Unknown | YaaC-like protein |

[a]Lankacidin Biosynthetic gene cluster
[b]BLAST search results from GenBank
[c]Open reading frame having a DNA sequence translated as an amino acid sequence. i.e., a DNA sequence spanning from initiation to a stop codons
[d]This column reports the sequence homology (%) of the optimum matches from lankacidin biosynthetic gene cluster
[e]Accession Number GenBank Entry with the highest score
[f]Error probability score obtained from the BLAST research
[g]Proposed functions of lankacidin cluster and chejuenolide gene cluster based on the combined results from the BLAST reserach
[h]Conservative domains reported by the BLAST research In fact, a gene encoding a polyketide synthase (PKS) associated with polymerization of a polyketide chain was constructed into a region separated by a 24.9-kb segment to be transcribed (FIG. 1). This indicated that the PKS gene modules were concentrated in a compact region, which coincided with a common opinion indicating that most of the genes required for PKS or NRPS biosynthesis form a cluster.

Unlike another known type I polyketide biosynthesis enzyme, all the PKS modules in the chejuenolide cluster coded for an acyl transferase (AT) domain and a dehydratase (DH) domain under separate ORFs of orf4 (SEQ ID NO: 10) and orf6 (SEQ ID NO: 12). Also, a PKS module encoding orf7 (SEQ ID NO: 13) is hybridized with a condensation domain (C), an adenylation domain (A) and a peptide carrier peptide (PCP) of NPRS.

Such characteristics are also examined in another known 17-membered carbocyclic tetraene biosynthesis cluster. Representatively, the biosynthetic gene cluster for lankacidin is similar to the biosynthetic gene cluster for the chejuenolide in that the biosynthetic gene cluster for lankacidin includes the PKS modules similar to those of the biosynthetic gene cluster for the chejuenolide, the configuration and arrangement of the domains constituting the PKS modules are similar to each other, and both the amino acid sequences constituting the PKS gene modules have a similarity of 49 to 63%. However, the biosynthetic gene cluster for lankacidin is different from the biosynthetic gene cluster for the chejuenolide in that a position of the orf2 (SEQ ID NO: 8) encoding the isochorismatase of the chejuenolide on the biosynthetic gene cluster is different from that of LkcH encoding an isochorismatase of the lankacidin cluster unlike the lankacidin. Also, the biosynthetic gene cluster for lankacidin is highly different from the biosynthetic gene cluster for the chejuenolide in a structural aspect in that the substantially biosynthesized lankacidin and chejuenolide are deficient in 6-membered-5-lactone rings linked via an ester bond formed by a thioesterase, and the biosynthetic gene cluster for lankacidin has an acetyl amide chain at the 3$^{rd}$ carbon atom instead of the 2-hydroxypropane amide chain (Arakawa et al. 2007; Choi, Sohn et al. 2008).

In conclusion, the genetic hierarchy of the chejuenolide cluster disclosed herein is distinguished from the hierarchies of other clusters participating in the synthesis of other polyketide macrolides, and are substantially different from that of the lankacidin cluster having a structure similar to the chejuenolide cluster in aspect of the configuration and contexts. Therefore, the gene cluster according to one exemplary embodiment of the present invention presents the first example of the cluster having a new genetic hierarchy.

B. Role of Chejuenolide Biosynthetic Gene

In particular, the present invention discloses a DNA sequence encoding PKS resulting in synthesis of a 17-membered carbocyclic tetraene polyketide precursor of H. chejuensis MB-1084. The PKS of the chejuenolide consists of six enzymes, each of which includes one and two modules. The six enzymes are represented by orfA, orf1, orf4, orf5, orf6, and orf7 (SEQ ID NOS: 6, 7, 10, 11, 12, and 13, respectively). The synthesis of the polyketide by the PKS is performed by a modular system in which a series of extension modules proceed after a loading module.

In general, the PKS loading module is composed of an acyl transferase (AT) and an acyl carrier protein (ACP). Each module consists of a ketosynthase (KS), AT, ACP, and enzyme domains serving to change β-ketone groups in an extending polyketide chain, that is, a ketone reductase (KR), a dehydratase (DH) and a methyl transferase (MT). The final module includes a thioesterase (TE) domain serving to terminate the extension by separating the mature polyketide chain from the PKS.

The PKS of the chejuenolide is composed of six modules, each of which consists of a total of 5 KS domains, 5 ACP domains, 3 KR domains, one DH domain, one AT domain, one MT domain, one C domain, one A domain, and one PCP domain. Specifically, the orf7 (SEQ ID NO: 13) specifies a sequence of C-A-PCP-KS as an NRPS-PKS hybrid module, and is a loading module of the chejuenolide that provides a starting material as one molecule of amino acid; the orf6 (SEQ ID NO: 12) is a module consisting of one DH domain in which an unsaturated bond is formed between α-carbon and β-carbon by removing one hydroxyl group of the β-carbon in the form of a water molecule in an extension procedure; the orf5 (SEQ ID NO: 11) specifies KR-MT-ACP1-ACP2-KS as a PKS extension module, and participates in rarely and repeatedly polymerizing a polyketide chain as type I PKS; the orf4 (SEQ ID NO: 10) supplies malonate required for an extension procedure as a module consisting of one AT domain; the orf3 (SEQ ID NO: 9) coats an amine oxidase, and participates in macrocyclization of a chain extending in a post PKS procedure; the orf2 (SEQ ID NO: 8) coats an isochorismatase, and is also assumed to play a role in the post PKS procedure; the orf1 (SEQ ID NO: 7) specifies KR1-ACP-KS1-KR2-ACP2-KS2 as a PKS extension module, and polymerizes a polyketide chain in which ketone groups of condensed β-carbons are reduced into hydroxyl groups; and the orfA (SEQ ID NO: 6) is a PKS extension termination module, and separates an extended chain from the module by means of hydrolysis.

Other genes present in the chejuenolide cluster represent genetic factors useful in synthesizing novel metabolites. Among theses, the orf3 (SEQ ID NO: 9) coats an amine oxidase that is an enzyme participating in oxidation of amines, and plays an important role in macrocyclization of a chejuenolide. This gene is closed and expressed in a heterologous host, and thus may be used to cyclize different types of polyketide chains having characteristics similar to the chejuenolide precursor. Optionally, the orf3 may be inactivated in a producing strain to produce a linear polyketide chain that is the chejuenolide precursor. Such a linear polyketide may be obtained by chemical approaches, but it is desirable to produce the linear polyketide chain using a single fermentation process without any chemical intervention.

Also, the chejuenolide cluster includes many genes transporting chejuenolide intermediates or final products from the cytoplasm to the outside or resulting in endowment of tolerance to producer cells. These genes include orfB to orfE and orf13 to orf17 (SEQ ID NOS: 2 to 5 and SEQ ID NOS: 19 to 23, respectively). The orfB, orf14 and orf15 coat an ABC transporter membrane permease, the orfC coats a transmembrane protein, the orfD, orfE and orf13 coat an ABC transporter periplasmic protein, and the orf16 and orf17 coat an ABC transporter ATPase. The genes may be cloned alone or in combination, and expressed in another polyketide producer strain, thereby causing an increase in yield of the formed products. Alternatively, the genes may be overexpressed alone or in combination in a chejuenolide-producing strain, thereby increasing the yield of the chejuenolide.

Further, the chejuenolide cluster many regulatory genes that directly or indirectly permit or activate biosynthesis and expression of resistant genes during production of the chejuenolide. These genes also include orf8 and orf20 (SEQ ID NOS: 14 and 26, respectively). The three genes may be cloned alone or in combination, and expressed in another polyketide-producing strain, thereby increasing the yield of the formed products. Alternatively, the genes may be overexpressed alone or in combination in a chejuenolide-producing strain, thereby increasing the yield of the chejuenolide.

Further, the chejuenolide cluster includes genes encoding enzymes indirectly contributing to biosynthesis of a chejuenolide. The genes also include orf2, orf9, orf18 and orf19 (SEQ ID NOS: 8, 15, 24, and 25, respectively). The orf2 coats an enzyme, isochorismatase, that catalyzes hydrolysis of isochorismate into 2,3-dihydroxy-2,3-dihydrobenzoate, the orf9 coats a haloacid dehalogenase that dehalogenates haloacid by means of hydrolysis, the orf18 coats an aminopeptidase that is an N-terminal peptide hydrolase, and the orf19 coats an NADPH-quinone reductase that converts quinone into hydroquinone. The four genes may be cloned alone or in combination, and expressed in another polyketide-producing strain, thereby causing an increase in yield of the formed products. Alternatively, the genes may be overexpressed alone or in combination in a chejuenolide-producing strain, thereby increasing the yield of the chejuenolide.

C. Use of Chejuenolide Biosynthetic Gene Cluster

Also, the present invention provides a nucleic acid molecule for expressing any one of a full-length chejuenolide molecule, and a precursor or derivative thereof. Such a nucleic acid molecule includes an isolated gene cluster(s) containing ORF, which coat a polyketide sufficient to direct the assembly of a chejuenolide. By way of example, the full-length chejuenolide cluster (SEQ ID NO: 1) may be introduced into a proper vector, and used to transform a desired producing host. In an aspect, this DNA segment is introduced into a proper vector in which a larger DNA segment may be handled. Non-limiting examples of such a vector include bacterial artificial chromosome (BAC) vectors or differentiated derivatives. In another aspect, the two separate segments are cloned into two distinct vectors with which the chejuenolide cluster may have compatibility in a desired producing host. In still another aspect, the chejuenolide cluster may be sub-cleaved into three segments, which may be cloned into separate compatible vectors. Use examples of 1-, 2- or 3-vector systems are disclosed in Tatsuno, Arakawa et al. 2007; Tatsuno, Arakawa et al. 2009; and Dickschat, Vergnolle et al. 2011. Once the chejuenolide cluster is cloned into at least one proper vector, the vector may be introduced into many proper producing hosts that can produce a chejuenolide more effectively than the natural hosts. Desirable host cells are host cells from species and strains that can effectively express these genes. Alternatively, the second copy of the chejuenolide cluster cloned into at least one proper vector may be introduced into a chejuenolide-producing strain, and the second copies of the chejuenolide biosynthetic genes may be expressed in the chejuenolide-producing strain to increase the yield of the chejuenolide.

The endowment of well-specified host with production capability may substantially improve various parts of processes causing optimization and development. That is, the optimum concentration of natural products in the producing strain may be effectively enhanced; the natural products may be purified under the known background of purifiable interference activities; compositions of a complex may be adjusted more effectively; and modified derivatives of the natural products may be more effectively produced through handling of fermentation conditions or by pathway engineering treatment.

Alternatively, the biosynthetic gene cluster may be modified, inserted into host cells, and widely used to synthesize various metabolites or chemically modify the metabolites. That is, for example, the open reading frames may be re-arranged, modified, and combined with another antibiotic biosynthetic gene cluster. By using information provided herein, the cloning and expression of a chejuenolide nucleic acid molecule may be achieved using conventional methods known in the related art.

As another possible use of the chejuenolide gene cluster, the ORFs selected from the chejuenolide gene cluster may be isolated and inactivated using conventional molecular biological techniques. An ORF substituted with an antibiotic marker cloned into a proper vector containing a DNA segment flanking the ORF in the MB-1804 chromosome is introduced into the producer strain, and two double crossing-over events of homogenous combinations result in inactivation of the ORF in the producer strain. This procedure is useful in producing the precursors or derivatives of the chejuenolide in an effective manner.

As still another possible use of the chejuenolide gene cluster, the ORFs selected from the chejuenolide gene cluster may be isolated, and brought under control of a desirable promoter. Then, the engineered ORF cloned into a proper vector is replaced with an original ORF as described above, or is introduced into a H. chejuensis strain as an additional copy of the ORF. This procedure is useful in increasing or decreasing an expression level of the ORF which is important to produce a chejuenolide molecule, or a precursor or a derivative thereof.

D. Construction of Mutant Strain and Production of Precursor

According to the present invention, a method of preparing a gene mutant strain in which an amine oxidase gene is disrupted, and a method of producing a novel linear polyketide from the gene mutant strain includes:

(1) constructing a chromosomal DNA library of H. chejuensis using a fosmid vector and obtaining a fosmid clone including a chejuenolide biosynthetic gene cluster (operation 1);

(2) constructing a knockout cassette (an antibiotic-resistant gene cassette) including DNA sequence upstream and downstream of the ORF used to encode an amine oxidase in the chejuenolide biosynthetic gene cluster (operation 2);

(3) constructing a knockout vector by replacing an amine oxidase gene with an antibiotic-resistant gene in a fosmid including the chejuenolide biosynthetic gene cluster using the knockout cassette (operation 3);

(4) introducing the knockout vector into H. chejuensis by means of an E. coli-Hahella fusion (operation 4);

(5) screening a H. chejuensis mutant strain, in which the amine oxidase gene is replaced with the antibiotic-resistant gene to be disrupted by means of homologous recombination, using an antibiotic (operation 5);

(6) culturing the mutant strain in which the screened amine oxidase is disrupted in a ZoBell liquid medium to obtain a culture broth (operation 6); and (7) separating and purifying a novel linear polyketide from the culture broth through a series of chromatographic processes (operation 7).

Advantageous Effects

As described above, according to the exemplary embodiments of the present invention, a nucleic acid molecule and a DNA sequence of a gene cluster biosynthesizing a natural polyketide-based chejuenolide having a peculiar 17-membered macrocyclic tetraene structure, which is produced by a marine microorganism H. chejuensis MB-1084, are provided, and the functions of gene products (enzymes) encoded by the nucleic acid molecule are disclosed.

Specifically, the genes of the chejuenolide cluster is selectively disrupted using a molecular biological method, and an effect of an enzyme encoded by the selected gene on the chejuenolide biosynthesis is disclosed, a knockout cassette and a knockout vector in which the gene is disrupted are provided, and a mutant strain prepared using the knockout vector, and a chejuenolide precursor produced by the mutant strain are also disclosed.

Furthermore, the chejuenolide biosynthetic gene(s) is applicable to development of novel materials as a mechanism for combinatorial biosynthesis, and is very useful in offering new guidance for studies of polyketide-based antibiotics.

BEST MODE

Hereinafter, preferred embodiments of the present invention will be described in further detail with reference to the accompanying drawings. It should be understood that the description proposed herein is merely a preferable example for the purpose of illustration only, and not intended to limit the scope of the invention, as apparent to those skilled in the art.

Example 1

Detection and Characterization of Chejuenolide Biosynthetic Gene

The present inventors constructed a chromosomal DNA library of H. chejuensis, and screened clones including a biosynthetic gene cluster for a polyketide synthase (PKS). DNA information of the two clones was combined to construct one contig, and the functions of the protein encoded by DNA were characterized using database BLASTP (a basic local alignment search tool for protein).

More particularly, a chromosomal DNA library was constructed from a chejuenolide-producing strain, H. chejuensis MB-1084, using a fosmid vector pCC2FOS (Epicentre, USA), and clones having a nucleic acid molecule encoding a ketosynthase was screened from the library using a PCR-based screening method.

To determine whether the fosmid vector was included in the screened clones, a ketosynthase was disrupted using a knockout system. As a result, it was confirmed through HPLC and MS that no chejuenolide extracted from a culture broth of H. chejuensis was produced.

Two fosmids having a group of the biosynthetic genes were screened from the library, and designated as 'pBG6E11' and 'pBG19A6,' respectively. The shotgun whole genome sequencing and primer walking of the two fosmids were requested to Macrogen Inc. to analyze a full-length base sequence of the chejuenolide biosynthetic gene cluster (SEQ ID NO: 1).

Next, the full-length 54.9 kb-long DNA sequence was divided into a total of 26 open reading frames (ORF) based on the BLASTp database from the National Center for Biotechnology Information (NCBI) (Table 1).

Figure 1:
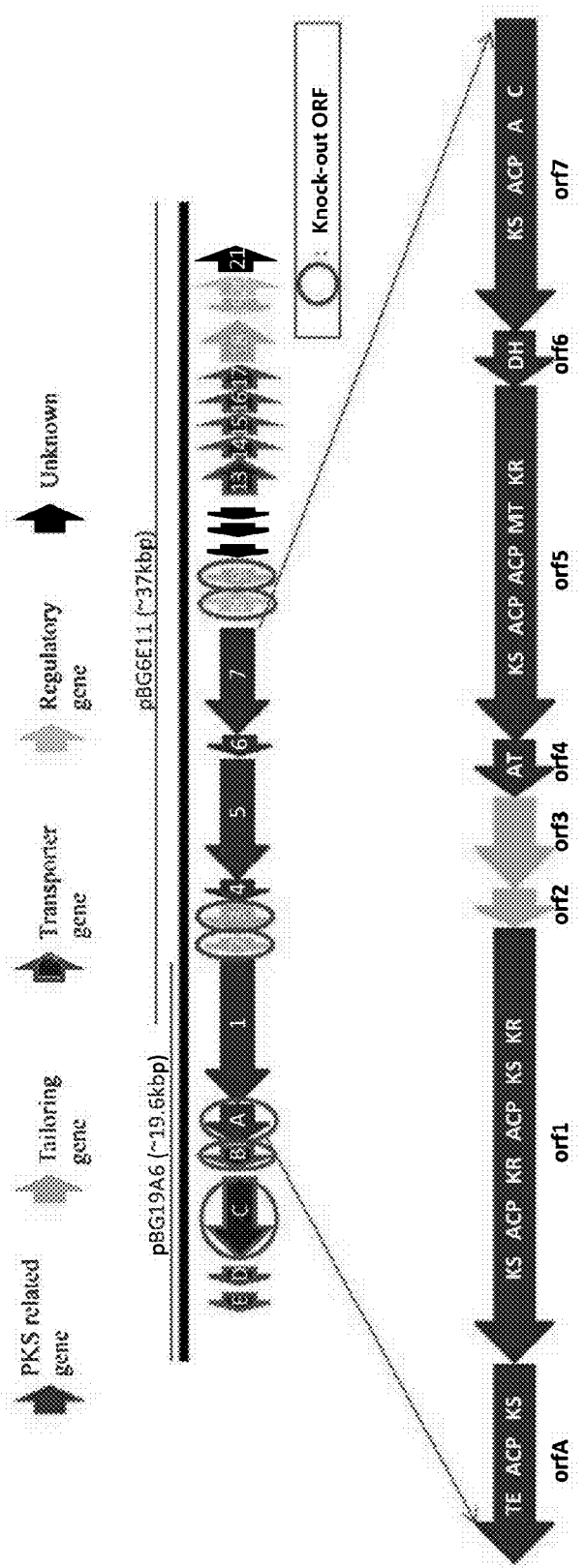
FIG. 1 shows a genetic map for isolated DNA segments and a chejuenolide biosynthesis cluster derived from the chromosome of H. chejuensis MB-1804 according to one exemplary embodiment of the present invention. A thick line represents a segment set forth in SEQ ID NO: 1, and fosmids carrying the isolated DNA segment are represented by pBG6E11 and pBG19A6. Each ORF is indicated by arrow, and numbered in Table 1. The direction of the genes is shown in FIG. 1.

Therefore, the present invention provides one contig containing the chejuenolide biosynthetic gene cluster, and two fosmids including the contig. The contig set forth in SEQ ID NO: 1 had a full-length 54.9 kb-long DNA sequence, and consisted of a total of 26 ORFs (see FIG. 1). In addition to the genes directly associated with biosynthesis of the polyketide, an isochorismatase, an amine oxidase, a dehalogenase, various reductases, a transporter, and transcriptional regulatory enzymes were found in the gene cluster. A clone including the two fosmids designated respectively as pBG6E11 (International Accession No.: KCTC 12316BP; and Korean Accession No. KACC91713P) and pBG19A6 (International Accession No.: KCTC 12317BP; and Korean Accession No. KACC91714P) was deposited in the International Depositary Authorities, Korean Collection for Type Cultures (KCTC) and Korean Agricultural Culture Collection (KACC).

Example 2

Figure 2:
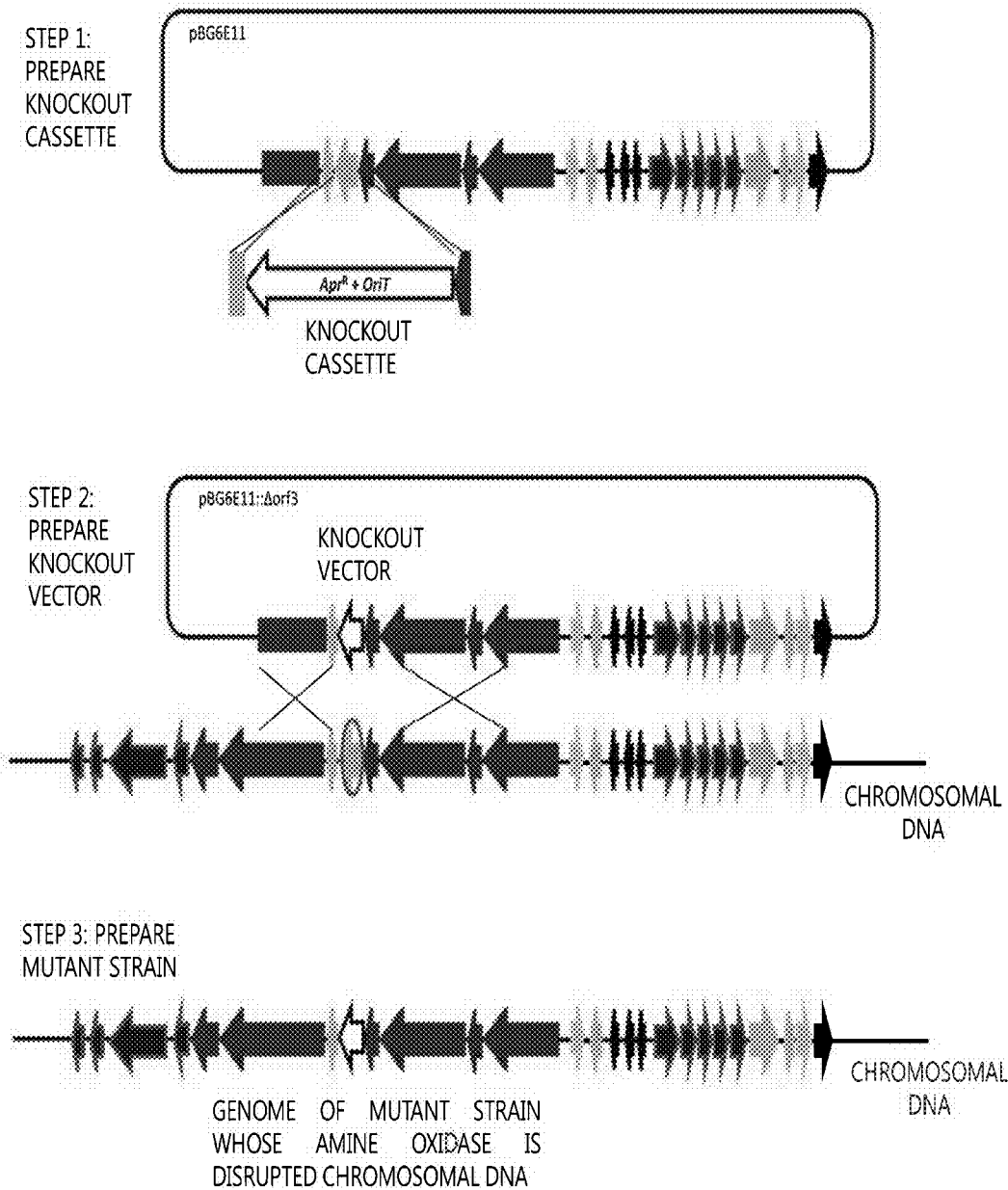
FIG. 2 is a schematic diagram showing a knockout system using homologous recombination according to one exemplary embodiment of the present invention. An orf3 knockout cassette encoding an amine oxidase is constructed using PCR, and a recombinant vector in which the orf3 in a fosmid pBG6E11 is substituted with an apramycin-resistant gene cassette (AprR+OriT) is prepared using homologous recombination, and introduced into a chejuenolide-producing strain by means of an E. coli-heterologous strain fusion to screen a homologously recombined knockout mutant strain.

Construction of Knockout Cassette for Amine Oxidase Gene Orf3 that is One of Chejuenolide Biosynthetic Genes and Method of Constructing a Knockout Fosmid Vector in which an Amine Oxidase Gene is Substituted with an Antibiotic-Resistant Gene To remove an amine oxidase from the fosmid clone (pBG6E11) obtained in Example 1, a knockout cassette was constructed using an antibiotic-resistant gene cassette. To knock out an amine oxidase gene (FIG. 2), a PCR targeting approach (Gust, Challis et al. 2003) using an apramycin antibiotic-resistant gene and a gene OriT associated with a fusion between Actinomyces sp. and E. coli was used.

For this purpose, a knockout cassette, which had an apramycin antibiotic-resistant gene and an OriT gene positioned therein and in which DNA sequences having a length of 36 nucleotides upstream and downstream of the initiation codon and the stop codon of the amine oxidase gene were included at the 5' terminus and 3' terminus of the gene, was constructed and used (Table 2).

To replace the amine oxidase gene in the fosmid clone pBG6E11 carrying a group of chejuenolide biosynthetic genes using an apramycin-resistant gene-OriT cassette, first of all, a pBG6E11 vector was transformed into E. coli BW25113/pHS8 using electrophoration, and the knockout cassette obtained by a PCR method was then transfected into BW25113/pHS8/pBG6E11 using electrophoration. Thereafter, the transfected cell line was induced so that the knockout cassette was recombined with pBG6E11 using a Lambda Red recombination vector pHS8, and cultured in a Luria-Bertani (LB) agar medium supplemented with 50 μg/ml of ampicillin, 50 μg/ml of chloramphenicol and 50 μg/ml of apramycin to screen transformants in which the amine oxidase gene was recombined with the knockout cassette.

To determine whether the amine oxidase gene was replaced with the knockout cassette in the E. coli strain (BW25113/pHS8/pBG6E11::Δorf3) screened thus, primers for confirming the knockout from the nucleic acid sequence spaced at approximately 100 bp from both of the primers used in the knockout were constructed to re-determine whether the amine oxidase gene was replaced with the apramycin-OriT cassette. The recombinant fosmid constructed thus was used to transform H. chejuensis with an amine oxidase knockout vector.

To introduced the constructed amine oxidase knockout vector pBG6E11::Δorf3 into H. chejuensis, the knockout vector was isolated from E. coli BW25113 and electroporated into DNA methylase-deficient E. coli (dam–/dcm– E. coli) ET12567/pUZ8002 in order to avoid a potent methyl-specific restriction system of a heterogeneous strain, and a transformed strain (ET12567/pUZ8002/pBG6E11::Δorf3) was screened on an LB agar medium supplemented with 50 μg/ml of apramycin and 50 μg/ml of kanamycin. A list of primers for constructing a knockout cassette is summarized in Table 2 below.

TABLE 2

| Primers | DNA Sequence (5'-3') |
|---|---|
| CheORF2_F | CACAAATTCATCAAGGACTTAATGGTTTAAAGGAGTCGAATGattccggggatccgtcgacc (SEQ ID NO: 28) |
| CheORF2_R | TGCTCCGGGAGGGATTGCGCCTGCGCTCAGACAGGGTCAtgtaggctggagctgcttc (SEQ ID NO: 29) |
| CheORF3_F3 | CACGCACAGGCTTAACCCATAGAGGTAATCAAAATGAAAATGattccggggatccgtcgacc (SEQ ID NO: 30) |
| CheORF3_R3 | CGCTTTTTCTTTTTGTAGCAACATTGTTCGACTCCTTTATCAtgtaggctggagctgcttc (SEQ ID NO: 31) |
| CheORF8_F | AGCATCCTAACAACAAAAATCACGGAGTCTGGCGAGATGattccggggatccgtcgacc (SEQ ID NO: 32) |
| CheORF8_R | TCCCTGCACGATCACGCCAAATCATCCCCACTAAGCCTTTCAtgtaggctggagctgcttc (SEQ ID NO: 33) |

TABLE 2-continued

| Primers | DNA Sequence (5'-3') |
|---|---|
| CheORF9_F | GGGGAGAGGACGTGCATCTAGTCATGTTTGACATAGACATGattccggggatccgtcgacc (SEQ ID NO: 34) |
| CheORF9_R | TTATTTTAATCCAATAAACCTAAAGGCCTTATCAGATTCAtgtaggctggagctgcttc (SEQ ID NO: 35) |
| CheORF19_F | ACGCACTGAAAACCGAACTGAAAAGGACCGCCCGACATGattccggggatccgtcgacc (SEQ ID NO: 36) |
| CheORF19_R | GATAACGCTCACAGGCGATATCCAGTTCCGCATCCATCAtgtaggctggagctgcttc (SEQ ID NO: 37) |
| CheORFA_F | TGTTGCTGTGTCTGGGCGGTCTGGCGATGAGCTATGTCTATGattccggggatccgtcgacc (SEQ ID NO: 38) |
| CheORFA_R | ACCGCAAACGGGACAGCGTTGTTTATTTTGCTAATCCGCTCAtgtaggctggagctgcttc (SEQ ID NO: 39) |
| CheORFB_F | TGTTGCTGTGTCTGGGCGGTCTGGCGATGAGCTATGTCTATGattccggggatccgtcgacc (SEQ ID NO: 40) |
| CheORFB_R | ACCGCAAACGGGACAGCGTTGTTTATTTTGCTAATCCGCTCAtgtaggctggagctgcttc (SEQ ID NO: 41) |
| CheORFC_F | TGCACTGTGGAAGACTATAAAATGAACTTGGGTGAAACGATGattccggggatccgtcgacc (SEQ ID NO: 42) |
| CheORFC_R | TCCGGCGCATAAGAAAGACTAGCGGTCGCTAATCAGATATCAtgtaggctggagctgcttc (SEQ ID NO: 43) |

Example 3

Construction of H. chejuensis Mutant Strain in which a Chejuenolide Amine Oxidase Gene is Disrupted To obtain a mutant strain in which an amine oxidase gene was disrupted in the chejuenolide biosynthetic gene cluster from H. chejuensis according to one exemplary embodiment of the present invention, the amine oxidase knockout vector constructed in Example 2 was introduced by means of a fusion between E. coli ET12567/pUZ8002/pBG6E11::Δorf3 and H. chejuensis.

For this purpose, the ET12567/pUZ8002/pBG6E11::Δorf3 strain was pre-cultured overnight in 5 ml of an LB liquid medium supplemented with 50 μg/ml of apramycin and 50 μg/ml of kanamycin, pre-cultured in 10 ml of an LB liquid medium supplemented with the same concentrations of the antibiotics, and then cultured at 37° C. for approximately 4 to 5 hours until an optical density of 600 nm (OD600) reached 0.4. The culture broth was centrifuged to obtain a pellet. Then, the pellet was washed twice with the same volume of LB to remove the antibiotics completely, and suspended in 0.5 ml of an LB medium.

As the same time, the H. chejuensis was cultured overnight at 28° C. while stirring in 5 ml of a Zobell medium (5 g of peptone, 1 g of yeast extract, 10 mg of $FePO_4$, 30 g of seawater salt, 15 g of agar, and 1 L of distilled water), and centrifuged to obtain a pellet. Then, the pellet was washed twice with the same volume of an LB medium, and suspended in 0.5 ml of a fresh LB medium.

Next, the cell suspensions of the E. coli strain ET12567/pUZ8002/pBG6E11::Δorf3 and H. chejuensis were added into a 1.5 ml microcentrifuge tube (or an ependorf tube) at an amount of 0.5 ml, mixed, centrifuged at 13,000 rpm for 30 seconds. Thereafter, the resulting suspension remaining after discarding most of the supernatant was plated on a Zobell agar medium supplemented with 10 mM $MgCl_2$, and cultured at 28° C. for 16 to 20 hours. Subsequently, 0 ml of sterilized water including 0.5 mg of nalidixic acid and 1.25 mg of apramycin was added, and evenly plated again.

Clones were formed when the cells were cultured at 28° C. for approximately 2 to 3 days. The clones were transferred to a Zobell agar medium supplemented with 25 μg/ml of nalidixic acid and 50 μg/ml of apramycin. The formed mutant strain was subjected to PCR to re-determine whether the amine oxidase gene was replaced with the knockout cassette. The mutant strain from which the amine oxidase gene was removed was designated as H. chejuensis O3KO, and deposited in the KACC from the National Institute of Agricultural Botany (NIAB) (International Accession No.: KCTC 12315BP; Korean Accession No. KACC91712P).

Example 4

Purification of Novel Linear Polyketide Produced in Mutant Strain O3KO in which a Chejuenolide Amine Oxidase Gene is Disrupted 200 ml of a Zobell liquid medium was put into a 1 L shaking flask, and a seed of fresh clones from the amine oxidase mutant strain was inoculated in the liquid medium, and pre-cultured at 28° C. and 200 rpm for 1 to 2 days while stirring. The pre-culture broth was inoculated at a concentration of 1% in 1 L of a Zobell medium prepared in the same conditions as the pre-culturing conditions, and then cultured at 28° C. and 200 rpm for one day while stirring.

The culture broth obtained thus was centrifuged at 10,000 g for 30 minutes to obtain a pellet.

The obtained pellet was suspended in 500 ml of methanol, and then extracted for 2 hours using an ultrasonicator.

The methanol extract was evaporated under a reduced pressure, and finally recovered with a small amount of methanol.

The methanol extract was fractionated in a 0-to-100% aqueous methanol solution using Diaion HP-20 column chromatography (Mitsubishi Corporation, Japan).

Figure 3:
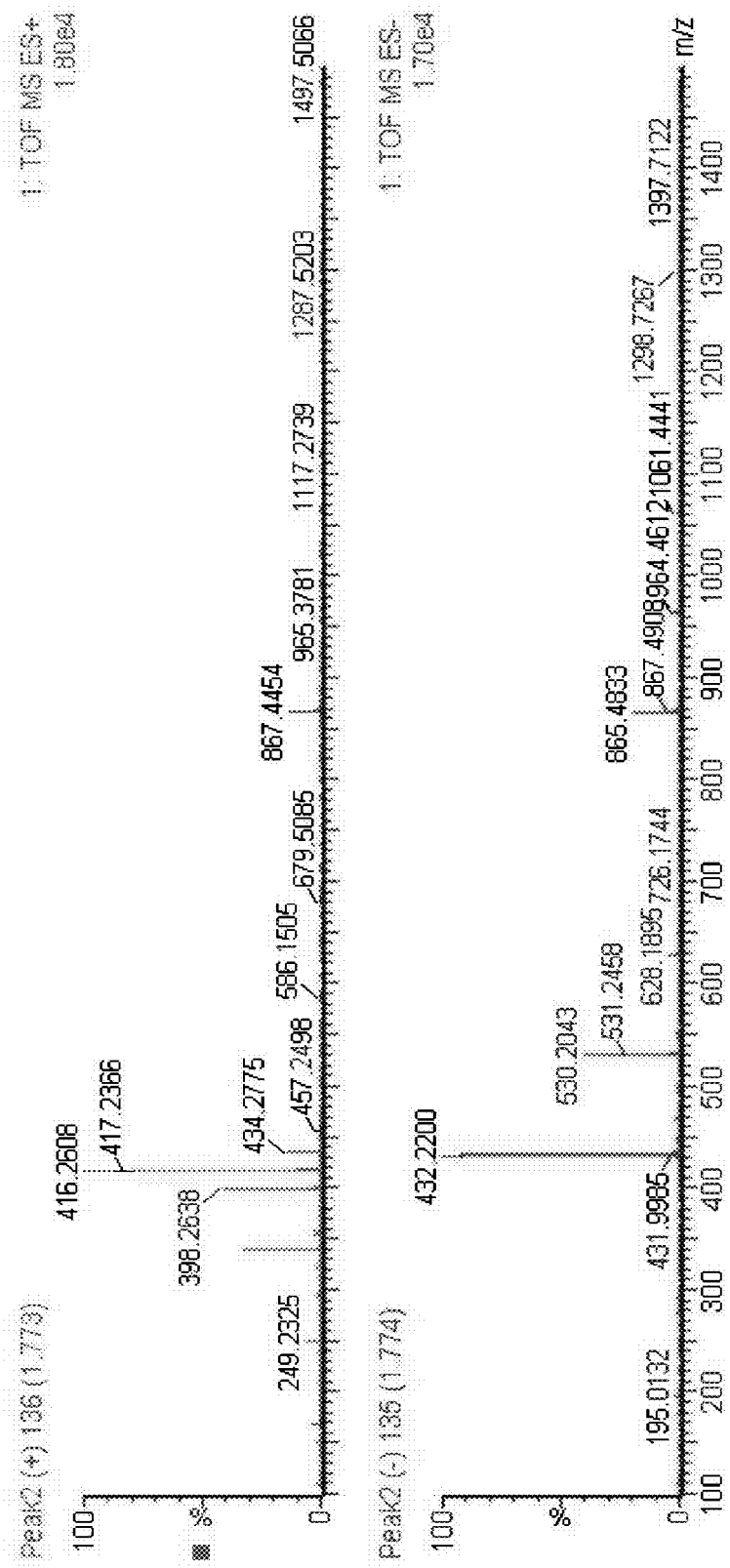
FIG. 3 is a diagram showing the results obtained by analyzing the molecular weight of a chejuenolide precursor. The ions of the precursor O3P2 are detected to be m./z 434 $[M+H]^+$ and 867 $[2M+H]^+$ in an ESI-MS$^+$ mode, and detected to be m/z 432 [M–H]- and 865 [2M–H]$^-$ in an ESI-MS$^-$ mode. Therefore, the molecular weight of the chejuenolide precursor O3P2 is 433 Da.

The resulting fractions of 40% aqueous methanol solution were concentrated under a reduced pressure, and recovered with a small amount of methanol. Then, the methanol extract was Peaks appearing when observed under a UV light of 254 nm while allowing a 20%-to-50% aqueous acetonitrile solution including 0.1% formic acid to flow at a flow rate of 2 ml/min through HPLC were analyzed using electrospray ionization mass spectrometry (ESI/MS) to obtain 2 mg of a metabolite having a molecular weight of 433 Da (FIG. 3).

The purified metabolite was dissolved in CD3OD (Cambridge Isotope Laboratories, USA), and subjected to $^1$H-, $^{13}$C- and $^2$D-NMR (COSY, HMBC, and HSQC) experiments using a 500 MHz nuclear magnetic resonance (NMR) spectrometer. As a result, it was confirmed that the general spectrum pattern resembled the NMR data for the chejuenolide, indicating that the purified metabolite was an intermediate produced in the chejuenolide biosynthesis pathway. It was confirmed that a new δC 169.5 ppm carbon signal which was not found in the NMR data for the chejuenolide was observed for the compound. In this case, the carbon signal corresponded to a carbon atom in a carbonyl group of a lactone ring, which corresponded to carbonyl carbon in a 6-membered d-lactone ring structure of the lankacidin.

Figure 4:
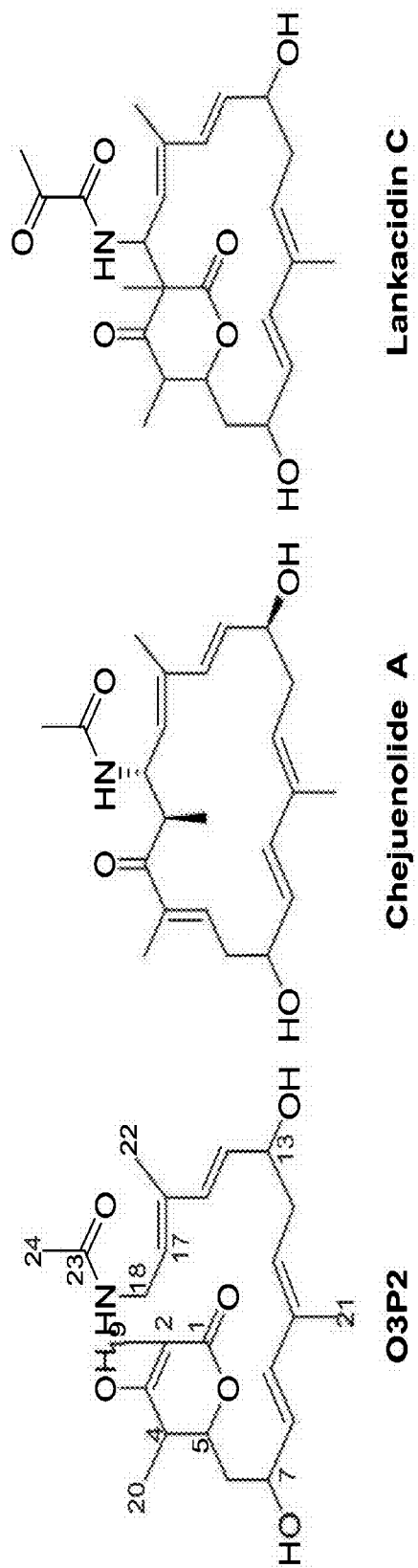
FIG. 4 shows a chemical structure of the chejuenolide precursor O3P2. The chemical structures of the chejuenolide precursor O3P2, chejuenolide A and lankacidin C are shown for comparison in the order from the left.

Also, it was revealed that a hydrogen atom appearing as a triplet corresponding to one hydrogen atom in δH 4.98 ppm linked to a $3^{rd}$ carbon atom of the chejuenolide moved upfield, and appeared as a doublet corresponding to two hydrogen atoms in δH 3.90 ppm. These results could be obtained when a bond between $2^{nd}$ and $3^{rd}$ carbon atoms disappeared. Also, the formation of a new double bond between $1^{st}$ and 2rd carbon atoms was confirmed from the fact that a $18^{th}$ methyl residue of δH 1.72 ppm appeared as a singlet, a $2^{nd}$ carbon atom of δC 49.9 ppm moved downfield toward δC 96.0 ppm, and a $3^{rd}$ carbon atom of the carbonyl group appeared in δC 205.6 ppm moved upfiled toward δC 169.5 ppm. It was confirmed a secondary metabolite having a molecular weight of 433 Da biosynthesized in *H. chejuensis* in which the amine oxidase gene was disrupted was a linear polyketide accumulated as a chejuenolide biosynthetic precursor, which was a novel compound whose structure was not reported so far (see Table 3 and FIG. 4).

TABLE 3

| Carbon No. | δH | δC | COSY | HMBC |
|---|---|---|---|---|
| 1 | | 169.5 | | |
| 2 | | 96.0 | | |
| 3 | | 171.2 | | |
| 4 | 2.48(1H, m) | 37.0 | 20 | 3, 20 |
| 5 | 4.15(1H, m) | 78.0 | 6a, 6b | 7 |
| 6a | 1.77(1H, m) | 40.6 | 5, 6b, 7 | 4, 5 |
| 6b | 2.08(1H, m) | | 5, 6a, 7 | 4, 5, 7, 8 |
| 7 | 4.29(1H, q, 7.0) | 69.4 | 6a, 6b, 8 | 5, 6, 7, 8 |
| 8 | 5.57(1H, dd, 15.5, 7.0) | 128.3 | 7, 9 | 7, 10 |
| 9 | 6.30(1H, d, 15.5) | 136.0 | 8 | 7, 10, 11, 21 |
| 10 | | 134.5 | | |
| 11 | 5.55(1H, t, 7.3) | 128.2 | 12a | 10, 12, 13, 21 |
| 12a | 2.39(1H, m) | 36.2 | 11 | 10, 11, 13, 14 |
| 12b | 2.43(1H, m) | | 13 | 10, 11, 13, 14 |
| 13 | 4.17(1H, m) | 71.9 | 12b, 14 | 11, 12, 14, 15 |
| 14 | 5.70(1H, dd, 6.7, 15.7) | 130.9 | 13, 15 | 13, 16 |
| 15 | 6.23(1H, d, 15.5J) | 133.8 | 14 | 13, 16, 17, 22 |
| 16 | | 135.5 | | |
| 17 | 5.46(1H, t, 6.8) | 126.9 | 18 | 15, 18, 22 |
| 18 | 3.9(2H, d, 7.0) | 37.0 | 17 | 16, 17, 23 |
| 19 | 1.72(3H, s) | 7.2 | | 1, 2, 3 |
| 20 | 1.25(3H, d, 7.5) | 15.2 | 4 | 3, 4, 5 |
| 21 | 1.77(3H, s) | 11.2 | | 9, 10, 11 |
| 22 | 1.80(3H, s) | 11.2 | | 15, 16, 17 |
| 23 | | 171.6 | | |
| 24 | 1.94(3H, s) | 21.0 | | 23 |
| N—H | 8.45(1H, br s) | | | |

The invention claimed is:

1. A transformant microorganism transformed from a microorganism having a genetic sequence of SEQ ID NO: 1 in its genome, wherein one or more genes encoding amino acid sequences of SEQ ID NOS: 2 to 27 that are included the SEQ ID: 1 are disrupted in the transformant microorganism.

2. The transformant microorganism according to claim 1, wherein the microorganism is a mutant strain Hahella chejuensis O3KO (International Accession No.: KCTC 12315BP) in which a gene encoding an amine oxidase in the DNA sequence of SEQ ID NO: 1 is disrupted.

3. A method of preparing a precursor of chejuenolide, comprising:
(1) culturing a mutant strain in which one or more of genes encoding proteins having amino acid sequences set forth in SEQ ID NOS: 2 to 27 are disrupted by knockout system, wherein the mutant strain includes a chejuenolide biosynthetic gene set forth in SEQ ID NO: 1 in the genome thereof; and
(2) obtaining the precursor of chejuenolide from the culture broth.

4. The method according to claim 3, wherein the mutant strain is disrupted at a 20,900th to 19,482nd region (orf3) encoding an amine oxidase having an amino acid sequence set forth in SEQ ID NO: 9 by knockout system.

5. The method according to claim 4, wherein the mutant strain is a Hahella chejuensis O3KO (International Accession No.: KCTC 12315BP).

6. The method according to claim 3, wherein the precursor is a chejuenolide precursor O3P2 represented by Formula 1.

[Formula 1]
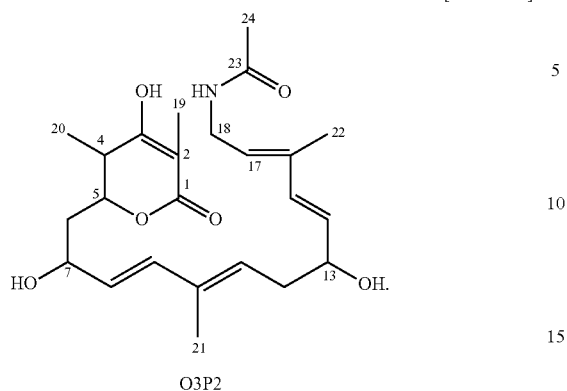
* * * * *

SEQUENCE LISTING

<160> NUMBER OF SEQ ID NOS: 43

<210> SEQ ID NO 1
<211> LENGTH: 51429
<212> TYPE: DNA
<213> ORGANISM: Hahella chejuensis

<400> SEQUENCE: 1

```
atggcttttc agtatcaggt acttttctt ctccaggcag gtcataccag cagttgtctt      60
tccaccgcag tagttggttt tctccgagcc cgttgggaaa ctttgttgac gctagaaaaa     120
tcccctccca ttttggagag ccttttttgcc attttacttt tctattcatt gatacccgtc    180
tttagactcg ctcattgctt gagcaggttt tttagttggc gtgggcgttg cccgacttgg     240
gcaaacggcg ggaaaatcat aacattctcc gtcagcatct tttctattgc tttaacgctc    300
aagttattat cgatacttat cccaaatccc ctcaatctcc ccactatcaa tcaacgcctt    360
aatcgccgca ttcaaccgct ccagcgcggc ggctttgttg gggtggatgc gtagcatgac    420
gtctacgccg ccgacttcga agccgggttc gaggcctcgg tagacgggt tttcgcgcat     480 gcggtaaagg gcgaggtctt tgttgatgat gacctggtcc aggcggccgg cgacgagcat    540
ggtgaggagt tgggattcgc cgttgacgtc gtagcgttcg atgtcgccgt tttggaagag    600
tttggtgaaa ctcgggtatt ggtagccgcg cacgacgccg atgcgtttgc cgattaagtc    660
```

-continued

```
cgagggcgct tcgacgggca ggcttttatt gcggccgaat agcaggatgt cgacggattg      720
cgcgtaggga atcgtaaaca gcccgagggt tttctcccct gcccgccatg cggggttcac      780
gcccgattcg atatccacca ggttttcatt gaacatcatc aagccgcggg ccaagggtg       840 agcttgattg ataaaggtgt cgcccgtgat acggctgatg cgtcgaaaa agtctttgta       900 gaagccggtg gggactccgt cctggtagaa ataatagggt ggaaattccg tattatgggc     960
aagcactctg aactcttccg cgtgcgcccc gcccttcggc ggccatatcc cgacaaggag     1020
aacgacgagg cttctcaaaa agatacccgc caacagcttt cgtagggtca ttcttgctct     1080
aacttctatg acaaaggcat gtgaaaagcg tggctctccc tgcgtccgtt tgacgccgcc     1140
tcagcgtaac gcgcttgctg ccggtagacg cctcgtacgt tacggtggct accggttaaa    1200
gcagtgtgct ctgatcatct ccttttggc atgacacatt tgtaaatcaa tgcaaattca    1260
accgccagac agtcccacct gttcgcacga aactgacttg tctggcggcc gatatgaaag    1320
tgcgggttat ttgaccccgt aatccgccag gatcttgtcg taggttccgt ccgctttgat    1380
ggcggcgaga ccccggttgt aggcctcaat aagtttctgg ccctgagcgt tggccttgcc    1440
tgtggccaca tgcaggtcgt tcactgacag agcgttattg gtgaattcca ccgagcccag    1500
gtcgatgccc gcctccttca tgacagactt ggcgacgatc tcatcttcca gggtcaggtc    1560
cacgcggtcg ctcaacagct ttttgacgtt ggcctcaatc gtccccgctt ccggtctgga    1620
gaaattagtc gcgtgggtga actcatcacc atagccgtag ccgctgacga tgccgaccttt    1680 cttcccagtg agactatcca gaccattgaa ctcaaacggg tcgcctttac gcttgataaa     1740
cttgatgctg ttctgcgcgt aatagttgct gtagttcagc accttggcgc gctcctccgt     1800
gaaccaggcg ccgggcaata tgtcgatatt gccgttgatc acatcattca acgcccgttt     1860
ccatggcagg attttaaaat ccaccgtgta cccctctttc tccatcgccg ctttcagcag     1920
cgcaatggat attccgggat cactcccctc ctgtataaat ggcggccaag gtcctgcgc      1980 agccgtgacg gtctccgcct cgcggaaaaa cgcaacgaac atggtcagaa tcaaggtgga     2040
aagagccttc atgcttatac ctctctgttt gagatagatc attggcgtag ccgataaac      2100 tttgggggga aaagttcatc ggacggaggg cgtggcgaaa cgaccagtaa ccgtattaag     2160
gttagtttat aaacagatct ccaacaaatt agagcgccgc tgggagtggg ttttttcggga    2220 gacaattttg ggcgtggcgg tagtttttgaa cgtgggagta gtcttgaacg tgggagtagt   2280
cttgaacgtt cgaatgttgg aaggcgcagc gcttttccaa cctaccgttg tgaggcggcg     2340
ttaattgtag gttggataag caaagcgcca tccaacagtt ttcgtggaac gagcgccgga    2400
gtccagcccg actccggcgc ataagaaaga ctagcggtcg ctaatcagat agacgttgtt    2460
ggcggagcct ttgggcagtt cggtggcgct ttggaacagg aagttctgga agttgttagc    2520
gccgttgagc acatgaattt ccgtactgtt cacgccattg cgtttgaaac cgatcaggtc    2580
cggcgcgccg tcgccattga aatccgcgac gcggaagctc cagttgtcat cggtgacatg    2640
cagcgccgtg gcgctgtgaa cgataaagtt atcgtagccg ctttgcgcac tcaggatgtg    2700
tacttccgtt ctgttggagc cgcctcgttt ggcgatgtac cagaggtcgg gccggccgtc    2760
gcggtcataa tcgctgacca ggaactcgtc ggaagagttc gggcgcaatc ccagccctgt    2820
ggcgtcatgc aacaggaagt tctgcggatt tctcccgtcc agcacatgca cttccgtgcg    2880
accgctgcct gttgtgttat gcatgatggc ccagatgtcc ggctggccgt cgccgttgta    2940
atcccgtatc gccatgtgat cgttgacgtt catgtaaccc aacgccgtgc cggactggaa    3000
gataaaacgc tgcaacccgc tcttgccgtc catgatgtgc acttctgtcg ttcccgtgcc    3060
```

```
ggtgttgcgt tccttgaatc cggcgatgtc catgtagccg tcgcgatccc aatccgtcat    3120
atcgaactgc caggcctcat tggtcgcttc caatgcgctg ttctgggcgg cggtggagat    3180
aaagctcttg ctgcgcaaca gcttctgaaa cgaggttctg gcgccgcctt gtttgttcag    3240
cacatagaca ttgggcgcca gtggacgatt ggcgccctgc gcgcatcctg aattcaaaca    3300
cacgaagata gagcccagtt cgccgggatt tctgaaatcc gcgccagccg gcgctttgaa    3360
gcgtacaaac aagctgccgt tttcataagc ccaggcgttg ccgtcaaacg cgcgcaacgc    3420
cgcccaggcg ccgaccgatc ccaactgaat cagcgggccg gagaagccgt actgtcccgc    3480
aggcgttccc agatagacat acacgttggg cgccacgccc ggcagctcca aagtcacgta    3540
ctcgccgcta ctcatactgt gataatcgaa gcgggtgatg ctgggaatct ggtcgtgata    3600
gatgtaggcg tagttataag cgccgtcgac catgggcaac agactgacgc cttcgatttc    3660
cttgcgggat tcggtatagc gcgcgccgtc actgcggaaa aaggtgctgt cctgacgtct    3720
gcggctgacc agcggcgccg gcggcagcca gatttcatcg gagggacgca cctccacgta    3780
ggcgaaacgg cggcgacttt ccatgccgct aagcccatct ctgatccggc tgctgttacc    3840
gtccaccagc atgggatggt cctgagtgat ggcggtcata ggctgaccgg tcaaggttcc    3900
atccacatcg taaatcgcgc cgttgaacca gaccggacca atgtaatcgt tgcgataacg    3960
cacttgataa ctgcccggcg agacggtggt gttgtgcagg gagtgcccgg agtatttgat    4020
gttggcgccc cattggtcga acagggtgaa attatcccgc tcgaaccccg tgaaatggga    4080
atcgcggata cgcactggac cgtcatacag aatatgcccg atcgccatgc cgattacgcc    4140
actggacgcg gatagaccca acggcgccac cggctcgtag ttttccgaag cgcccaccca    4200
caacacgcgg ttgtagtccg tcacccaggt gctggcttcg ccttcatagt tgtccgccac    4260
gatcaggtcg ttgtaggtgc ttttgccccg attgccgccc actcgggaat acattcccag    4320
atagttcttg tacaccgtca gcccattgat gaccggctcc tgttgaggca tgtagtcgtt    4380
gttcagatta ggcgtttgcg aagcgtcatt aggggtgggc gccatgccca gcaaccagcc    4440
gtggaaactg gagtgcgcgg tgttattgtc aatggcgccg gcgggcaggt tctgcacatt    4500
gggattcagt ccctgctgaa aaaccggact gttcggattc tgatgaaagg cgaaccagaa    4560
accggagccg tcggaaccgg cggcatggtt attctgtacg atattgttgg ggttggtgat    4620
ccagaaggtg gacgggccgc tggcgtttct caatctgcca ttggtgaaat cgctgggcag    4680
cagtgcgtat tccggtgcag gcttgcgggt caccatgccc agattgccga cgatacggtt    4740
gccggtttcg ttgccgtctt ccatgaagac cgcgtgtccc aagttgtcgt agcagacgtt    4800
gttttccact gacgcgttgt tcgtaccgtg aatggtaatg gcgcgattgt aggtgtggtg    4860
gatactggaa ctgcgaatgt attgcccggc ggcgttaccg gccagatgcc aatggaaagg    4920
ataacgtccc agcttgcggc gctgccccat acgggtcaac tccacattgg aaagacggcc    4980
gaaggcgccg cgcatcacca tgatgttgcc gccataggcg gtgcggtcgc tgtctgcgtc    5040
cccctgaatc cggagattac gggacaacag acccacttcc gcacgctcgt ccagcgtcca    5100
gctttgtccg ttgtcgctgt attgctgcag tttgccgaag tggttgtagg caaggcggtc    5160
attgagagtc agcgtctttc tgtcgccgct gatgctgacg atggtgaatt cttccgcgtg    5220
attcatgtcg aaatcgctgg aggcgatcac aatgcgatcc cctgcccgcc agttcaccga    5280 ctcctttcaac gtgatgctgt tgtcgccaat tgcggcggaa gcgcccaact gggtccagga    5340
tcgctgaggc tggccatgca tttcgatacg tccgccgttc atggcgtgaa tcagcttgga    5400
```

```
ttccgccgcc ggattatctc ccagcaaggt aatgacgccc tggccattga acggggcctc      5460
ttcccgaccc agctccaaca ccccgcccgc catgacgtgg atttccgcca catccagcgt      5520
aaagtcccgg ttaaccggcg cggtgagaat ccctcgttg atgatcacat tcgccgcgtt       5580
cagattatcc agcaccatgg tggcgccagc gggaatgtag acttcttcgc caggcccggg      5640
gaccgagttc tccagccagg acgacgcctc cgaccacacc ggcagcttct ccaattgcac      5700
gtcgtcgaca aaagcggtgt tatcgccgct tgcgttcaag ccgctcaaca ataattggta      5760
tttaccgggt tccagccaca tcgccgtgga gtgatacagg cgataattgc tgtcctgcgg      5820
acggattcgg ccaatctgac tgccggcgag ggatacgcgc agggtttgtc cttgaggaga      5880
gttgatacag ccccgttgcg ctccgcgcag attaacgcgg taaacgcctg cgttggggat      5940
ggtaatggtt ttctgcacct gccccgtctg ctgaataaac agcgcctgct ggccctgggg      6000
cgtggcggga ttgcatgagg taaacgcaga gccgttttcg gtaatgcccg cgccatcggc      6060
gaaggcccac tcaccgcctc tgggaagata ttgatagcct cccgagggaa catccggcgt      6120
ctcaaaaccg gactcgccga tgggcgtcat gacgccctcg ctgaccgccg tcaccgccat      6180
cgcgctctga caaaaagtca gcgcagcgac ggtcgtcagt acggagagcg cccccttgcg      6240
ttttaagaca gagccgcgcg caggcccgtc tgtatgaata ttcgtttcac ccaagttcat      6300
tttatagtct tccacagtgc attgattctt agctctggct cgcctgaaca ggcataaaag      6360
cgattccggg tcggcgctta aaacagacgc agaaatccca catccaaaat caccccttaaa     6420 cgtttcagac ccggcataga taaattaagt aaaaagctcg gcattgctat cttgtcgccg      6480
aaaccagaac ctcatccttt aaggcgaata accgaaatgc atcaagccaa taccgccgg      6540 cgcagccatc aaattaacgc ggtgtttctg ttatccgtat cccaggcgaa cattaacata      6600
agttcacagt caatcctcta gggcaatatt aataacccat acgggataac aattaataga      6660
gaattatcgg ggttaatata caattcaatc tgcatctcca atgacagatt ttcatatttt      6720
aattatgcgc ggttggaacc tgttttgtat gatcaaaaag ccctgctgac aggccctgca      6780
agcctcattt agactactca gcgacatagc gacatataga tatggagagc ttttcgtgtc      6840
agaactcatt agtgaaaaga agaaatttga agaaacctgg gaaaaggagg cgctcaaagc      6900 ttttttctcgt ttgttttcat cacagcaaat aacggagttt gatcaggctt tgttcggcga      6960
tcaatttgat aactttcgtc agggaatgag cgtcatgttt cctgattcgg atgatattaa      7020
ttttaaaaga ataaggtcca acagattaaa gcgtctcggt tatagctggc aggcggatat      7080
aaagacatgg atcaaagtgt cggattaatt gcatcatgat gcatagccgc ctgcttttca      7140
tttaaacaac cagaaagaca ggcggcggaa ttcaaacgct gaccgcaaac gggacagcgt      7200
tgtttatttt gctaatccgc gtatttcacc tgccgcgcca ggctcatttg ctctttacag      7260
caaaccagaa tcgccaggca gacgcaaagc agtgcggaca ggataggagc gctgacgctg      7320
atgttagcca caaagccaaa ggcgaagccg gagaagcctg cgctgaaggc ggcgatggcg      7380
gcggccattc ccatgatgga gccctgccgg ctggcgtcga cgctcatgga taattgcgcc      7440
atcaggccgc tgtaggacag gccgaacccc acggctccca gggccgccag cagatacagg      7500
gcgtagacat tggtgctgat cagggttccg ccgatgcaga gcgccatcag cgccaacgcc      7560
actccgacca tgccgagggg cttcagcatt ttcatggcga cgcccaccag aaacaggaac      7620
gccgacgcca ggccaaagcc gacccaggag acgaaactac tcacttcctg ctgccccagg      7680
cccagctccc ctgtcagata cagaccgata aactggaaga aggtattcca gcccaccagc      7740
atcaacagca ggagcaaggc gtaggtgcgg atgtccttga ttcgcactgc gtcgagcagg      7800
```

```
ttcgcaatgg ggttgggaag ggtcatcccg cggccgtcgg cgtccgcttg ctgatcctga   7860
aacaccagca gcaggatcag caaattcacc acagacaacg ccgccacaaa gacaaacggc   7920
gtctgcagat tgaaccaggg aactagcgca ggatcgctca gataaccgcc gatcaacggg   7980
ccgacgacat aacccaggga gacaaagaac atgatgtagc cgatgtactt ggcccgcagc   8040
ttttcctcag taacgtcaat aatggacgcc tgcgcgacag gcagactgcc agagaaaaag   8100
ccgccgataa ggcgcccggc catgaacagc acaggctttt gaacgccag ggcgagcgcc    8160 agaaagacat agctcatcgc cagaccgccc agacacagca acagcgtctt ctttcggccc   8220
aggccatcgg acaaggcccc cagcaacggc gcgccgaaaa acatggcgat ggaaaacgcg   8280
cccaacgcca cgccatagac gccattgcgg aaactctccg atccctcgct gatcagtcct   8340
gccgccggat cgtgggcgat gggcgtcagc atgggaataa tcaggctggc gcccaggtta   8400
tcaatgaaga taaccagata aatgccgatt aaactcaaca tccttatgtt tgtcataaaa   8460
cctctcgtac tggagcgccc tacaaggacg ccctttattt tttccattat ttgctattgg   8520
gtttgccgct ttactggcct ctttatcttg gccgcttcac cgcagcttct tcgtcttaac   8580
cgatgccctc cccattgaga aagcgcagta attgcgtatt aaaaaaccgg ctcgcggtca   8640
gggggataaa gtgaccgtgt cccttcacga ccagttcggc ggcttgagga atgcggcgta   8700
actgatcgaa tgtggcttca tcgatgacgc agtcgttttg tccatgcgtc aacaacaccg   8760
gcatggcgat cccgccaaga cgcgcattga cgtcgaagcg catcagcgca tcgtagtaat   8820
aacgcagcac gctcattggc gcgccagcgc ccaggctggc gacaatatcc tccgcgccgt   8880
caaacacgat ctccagcatg tcgcgatgcg ccttcagttc atcatgcagg tccagcgtat   8940
tgccgaatac gtcctcgccg aagctcggcg ccgtgctgat cagggtcagc gaacgcacta   9000
aatccggatg atgaatggcg atcagacagg acaggcagcc gccagagac cagcccacca    9060 gatcgacggc gttactgctt aactcttgtc tgataaaaat cgccatgtct ccgccagcg    9120 cttccaggga aaacgcagca cgtcgaaag gcagtctttt gtggccggga tagattggaa    9180
ttaacacccg tcgaccggac tgggtcagcg cattgatttg ctgcgtccag gcttccgcgc   9240
tggtgttcag gggcggcgcc agaataatgg ccgccttc cccatagctt aaccattgcg     9300
ccatggggcc agatgcggtc gcagatgcgc tttctctcgg cgcttccgct ttcaccttct   9360
cttccgctat tccctctct tccgctattc ccctctcttc cgctattccc ctctcttccg    9420
ctattcccct ctcttccgct atcaccttct gctccactat ccccttctcc tctgcgacag   9480
tggcgctctc aacgcctgcc gcggctatag cggcggcgag atccgccagc gtgcgatatc   9540
ggaacaagtc atgagcctgc aggcctgggc cgcgctgttg atagggggcc agcagtttca   9600
gggcggacag ggaatccagc ccgagatctt cgattaacgc gtcccgaggc agttcatccg   9660
gcgcaaaccc cagcaggtct gacaccgcgg cgcgcagctc ttctacaatg gcttcggtgg   9720
aaagggtcga atcagcctgg gtggacggag aagcgtcagc aacttgctcg tcttcccggt   9780
catcaatcca ataacgcttg ccgtcaaacg gatatgccgg cgcgttgacg tctggattca   9840
gtgacgcgac cgcgtccaat cggcgccgca cttcccctg ctcgcccgcc cgccacagcg    9900
tcatcagggc cagtttatcc gtcgacaggg taagttctcg cacggccaaa ggcgcatttc   9960
gcaatgcgtc tccggcgtcc aactcgtgcg ccagttgctc caatgcggat agcaaatctg  10020
acttattcgc ggcgatgatg gcgcaatgca gcccgtaacg ggggcgacgc agtaacaact  10080
ggctgagatc ataaagcgcg tcctcgtcca gcttcccgac taattgccgc acccgtccga  10140
```

```
cactggcgat caggctgttg cggctttgcg ctgagagaca gaacggcagc gcctctcccg   10200
tcctgcgggc ggccagattc cgcgttgtcg aaggcatttt ccgcagtagc gcgtgcccat   10260
tggagcccgt gaacccgaag gcgctgacgg cgcacagggg tttatcctgg ggccatggca   10320
aaggttcgaa attcatgcga aagccggcga agtcaatcag cgcattggtt ttacgcaaag   10380
ccggaaatgg cggaatcgtc tcatgcttga aactcagcag cactttgatg atgccggcga   10440
gcccggagca caccagggag tggccgataa ttggcttgac cgcgcccaac agacaggcgt   10500
aatcctcgcc atggtctttg aacgcttcgg tcaatccgcg catctcaatc ggatcgccca   10560
aatgcgtgcc agtgccgtgg gtctccacat aggccagtcg cgcgacatcc acctcgtgac   10620
gacgatacag gttgcgaatc agcctgcttt gcgactgcgc gttgggcgcc atcaacccat   10680
tgcttctgcc gtcatgattc aagcccgttg cgacaatcgc gccgtagacg cgcagccccc   10740
gcgctttggc ttctccgtag cgcatcagga taaccgacgc gcatccctcc gctggcgtga   10800
aaccgtccgc atcgtcgctg aacgcggcgc agcggccgct tggcgatgac atattggagc   10860
gttgcgcaaa ctcaaacagc tccggcgtgc tgaacaccga cgccgccgcc acgatcgccg   10920
cgccgcaatg gcccgcctga atattgaggc aggcttcatg cagggcgctc aacgaggagg   10980
aacaggcggt gtccagagtc agcgacggcc cattgaaatc atagaaataa gagatcctgc   11040
cggacagggt cgaggtggcg ttgccaagaa aactgtgcgt actgaacgcc tgctcaggat   11100
gcctcgccac cacaaattta taatcgccgg gaagactgac tgcgaacact ccgcactgca   11160
gctcccgcaa ttcgtccagt cccaggtagc tgtcgtcaat ggcgtgctgc gcggactgca   11220
tcagcaggcg ctgctgcggg tccatgcatt tggcttcgtt gggggaaatt ttgaaaaagc   11280
cggcgtcaaa atgatcgtag tcaggcagaa agccgcccac gaactccctc gtcccctgcc   11340
tacgccagcg atctgtcgtc gtcagttggg aagtcccttg catgatggcg tcccaatagg   11400
cgtccacgcc atcgcagccg gcgaactgcg ccgccatgcc cacgacgacg atggcgtcat   11460
cctggattag gtcgtcttgt ggatcttcgc ctcgggaagc ctgcgtgggc tcactcgatt   11520
gctccgccgc cccggtttgc ggcgtgtccg ccagaacctt acttatgtgg acagtaagcc   11580
cgtcgatgct gatgcattcg tagatatccg tcggcgtgat tccacagtcg aaatggcgat   11640
tgatgagctt gctcaattgc gccgccagaa tggaatccac accgagggtc gcgacttccg   11700
cgcccgtttc aatatcgccg gggtccgcca atagcgcctc tgcaaacagc gcgacaaggc   11760
gctctttaac ttccatgatt caccctctttc atcgcggcgc tgtccgccgc ctgttcaaac   11820
caataaggct tggtgtcgaa gacatatccc ggcaagtgca gacgacgata agcgccctct   11880
gcaaacacgg gcgtccaatc aatcagggcg ccttgctgat attgcgcctg ggccgtctgc   11940
attagggcag tccaatcgct ttgcgacagg tccggcgtcc aatgcgacgt tttaccggcg   12000
cacttttcct ggccggtcgc atcggtggcg cgaatctgtg cggtcaggtc ggcgacggag   12060
gtggcgatcc agctcagacg atacgcaaag gcctcacgtc cggtgttcag ggtgaacgca   12120
atatccgcca actcatgatc ggcagtttga aggcgctcca ataagcgcgc cttcatggcc   12180
gccagcgaat aaggcgtctt ggcgctgagc gtcaccagcc agcagggctt tggcgcccgt   12240
tcgacaacgg ctgattgccg cccctcggac aggacgacat gagcgttgga gccgccaaac   12300
ccaaatgaac tgataccggc cactctcgga cccgtcgcct cccagtcgcg attctcggtc   12360
agcagccgga aggggccatc attgagatgg atcatgggat ttaggcggtt aaagtggata   12420
ttggccggta accgccgatg ttgcaggcac agcagcactt tcagcagcga cgcgatgcct   12480
gcggcgggct ccaggtggcc gacattggac ttcactgcgc ccagcgcgat actgcccttg   12540
```

```
ctcttgtgcg gcgccagtgc gtggaacgcc tgatgcaggg cgtcgatttc aatggggtcg    12600
cccaattgcg tgccggtgcc gtgggtttcg atatagctga cccgctccgc cagttccggc    12660
gtgtaggcct tttgcagcaa cgctgactgc gcctgtgggt tcggcgcggt taacgagttt    12720
gcgcgcccgc catggttttc cgcagaggct tcgatgacgc cataaatgct gtcgccatcc    12780
cgttgcgcat ccgccagccg cttgatcacc acgcacccga cgccttctgc gcgcacatag    12840
ccgttggcgt cggcatcgaa ggtcgcgcag cggtaatcgg cgagagcac ccccatgctt     12900 tgcgccgcat cgctgatagc cgggtcgatc agcagactca cccgcgccca cagcgccata    12960
tcacactcgt tgcgctgtaa agacatcacc ccgcgattga ccgccaccaa cgcgctggag    13020
caggcggtgt cgatggtctg actggggccg ttgaagttga acaggtacga cacccggtta    13080
gccagcatgg cgtgggcgtt gccggtggcc gcataggggg cgagctttg ccccaggtc      13140 tgcagcaagg tctgataatc gttgaactgc accccggcga acacccctac gctactcagt    13200
aacgccggcg catagcccgc gtcggtcagg cgttgtagc tggtctgcag aaacagacgg     13260
tgttgcgggt ccatcaacat cgcttcgcgg gcggagagac cgaaaaagcg cgcgtcgaaa    13320
cgctcgatat cgtcaatggt tcccgcgtaa taggatttat ccccccaacg cgccacaggg    13380
cgaatggcgc tgcggttttc cgtcagcaac gtccagaatg cctctagatc cgccgccccc    13440
ggcatgacgc cgctcatgcc gataatggcg aagcgttgct ctgacaattc ctcggagcgt    13500
ttctccgcca acggctgctc tactgacgcg acgccggcca gggaagacgc ggcggatgac    13560
gcctcaccgg tctgcgaaac cgcatcgtca gcactgctg cgcccgccag ggtggcgccc     13620
tgttgctgca gatattccgc cagtcgctgg atattgttgt aactgaacaa agcattaggc    13680
gggacctggg cgccgaaggt cttgccgata tcctgcgcca gggtctgcat catcaccgag    13740
ttcaggccga ggtcgcccca gctcttgtcc gtgctgatgt cctcttccgc gagcttggtc    13800
agcgcctcca ccaagcgggt cagccccgcc cggatctgcg cttcagaggc gacgacctga    13860
gaggcgtttt gattgccgtt tttagcctgt tgttgcgagt tctggactgt agacgacgtg    13920
aagcgcgcgc ggattttctc cagatccccc accagcccca tgacctggtc atattgatcg    13980
gcgacgccgt tgatccaggt gatgaaaagc cctgcgccct gagccagcgt caacggaaca    14040
aacccataat gacgtttcag gtagtccgcc agagagcggt actgatccat cagattttcg    14100
ctatcctgat cgtcaatcca cagaggccag ttgatgacaa cgctatgccc tttgcgcgcc    14160
ccttgcctga cccgtccatt gcgctctgcg gcaaactcat ccagaaaacg attggcggcg    14220
acatagtcgc actgccccac attgcccatg atgctggaca tggaagagaa caggcagaag    14280
aaatccagtt ccagatgggc ggtgcagcga tccaattgcc gggttccgc cacctttcgcc     14340 gccatgaccg cagaaaagtc cgccagcgac ttgttctgca cctgggcgtc tcttaatacg    14400
ccggcggact gaatgacccc atgcaaacgg ccatgctttt gcagcacatc ggcgatcagg    14460
cgctccgcct gaaccgggtc ggcgatatcc gcccgcaggt aactgatttc accctgcggc    14520
cactgctgca accaggcttc ccgctctggc gacaaggcgg agcgtccgac cagaatcact    14580
ttggcgttgt agtccgcgtg cagacgtcgg gcgatttctc tgccgatcat gcccatgccg    14640
ccgctgatca gatacacgcc gccctcgcgc aggcgcgcgc ccggagccgg ttcaatgctg    14700
gtcaggctgc gctcccagcg ctcttcttgc cggcgttcga cctccttaaa ttcgtccgtt    14760
gtatcggcct gttcggccaa cagccagcgc cagtcctcca attcccagga cccagcgggc    14820
ttggcgattt gcgcctgtct gtaatgaacg tccgtatttt ccagcgccag cactctgaaa    14880
```

```
actcccccca tggcgatttg ttcaggggc tgacggctgt cactgacatt caacagtgcg    14940
caagggcgcg cacaggcctg catcgccttc gccaggttca acgccatcgc gtcgctccag    15000
gggacgttgc agttgatcca gcggatctct tcctgctgca gttcatgggc gatgtaatcc    15060
agcgcctggg tgaaatcatc caggtgatcg ggccgcaggg tcagggcgtc atgttggaaa    15120
ctcaatgctg tccctggact gacgcgcaga acccgcgcac cgtcgatcat cggcggcaac    15180
acttgctctg acgagccat caccgccacc agcgggattg gcttcgacaa tgttggagat    15240
tcggtgtgtc gccatactgg cgtcagcaat acggcgggcg tcgagtccag cgtctgcgct    15300
gaacttggcg cgacaggttt aacaggatta gtcgctgccg aaacggcttg cgcttgcagc    15360
gtcggcgccc agtaaacatc acgggcgaaa ggatatttag gcgcgctccg cagcagggat    15420
ttcactggaa agctgccggc gaagtccacg ctgtcccctt gcaggtaggc gcgcattaac    15480
gacgcgaagg gctggttcgc cgggctgtcc gcattggcct cgcctgcgct ttccagtctg    15540
tcgatcaacg cggccgcaga cccgacgaca aaacatgcgc gctcggcgtg atgttggcgg    15600
gcgcaacaca gggtgtaact caagctgtat aaacaggtct gcggttgtgc gcgcaaatac    15660
gccgccagtt gttgccgcac ccgccgcagg ccgctgcgat tgggcgccga caaggcgata    15720
agatactccg cttgcgccgg gaccgtgccg gcagggtctt tagggaggta ctgctgcaga    15780
ataacgtgac cgttggcgcc ccccgcgcca aaagagctga gcccggcgaa gcgggtggcc    15840
gctcccgcca gaggccaggg ctgcttctcc cgcaccagtt gaaagcgggt ttgctcaata    15900
ttcagataag ggttctcaat ggcgcaatgc agcgtgggag caagctgctc gtgggcgaac    15960
tgctggacca ccttgaagag tcccgccatc gcggcggcgg actccagatg cccgatattg    16020
cttttcaccg agccgaggta acaaggcgtg tccgccccct ccagattagc gccgtatgcg    16080
ctttgcaacg cctgcagttc gatgggatcg cccagcccgg tgccggtgcc atgggcctcg    16140
atgtagttaa cctgggcggg attcacgccg gatttgcgca aggcgtcctg aatcacccgt    16200
tgttgcgctc gcgccgaggg aaccgtaaag ctgctggttt gccgccgga attaatcgcc    16260 gtggcgcgta cgatggcgta tatcacgtcc tgatcgcgca gggcgtcggc gacggacttc    16320
aacaccacca ccgccgcgcc ttcgccgggg acatagccgt ccgcctccac gccgaaagcg    16380
tggcaatgtc cgctggcgct gaggaacttg ccttgggata acagccggta tttacccgga    16440
tgcgccatga tattcacgcc gccggacagg gccatgcggc attcgcccag ccgcaggctg    16500
ttgcaggcca tatgcaacgc ggtcagagag cccgagcaca tggtgtctac agtcaggctg    16560
gggccttgca gatcaaatgc ataggacacg cggttggcga tggcggcgaa ggaactgctc    16620
accaccctgg aagcatccag gtcctgataa tggccgaaca tggcggcggc gaacacgccg    16680
acgtccttac tgggggaaac aaagtacccc gcgtcctcca aggcatggta gctgacctgc    16740
agaaaacgtc tttcctgagg atccagcagc gccgcatcca cgggcgcaat attgaaaaaa    16800
gccggatcga actcggcgac gccttccata aagccgccgt gacggccata ggtcgcctcc    16860
ccctgcgcgg ttgaggcgga gtaatcccgc cgccaatccc aacgggactg gggaatgacc    16920
cgcaccgcgt cttcaccggc ggcgagcgag cgccagaacg cttccggcgt cgcgccatta    16980
gggaactctc ccgccatgcc gatgatcgca atgtcgtcgt cccgataagc gtccgtcgag    17040
agtttgggtt cgttggtcaa cgttggtgta gcgccgccgc catgaggttt gacatgctca    17100
gagttagctt ctttgcgtc aggcgtattg tctgtggcgt caatttgcgc ttgttctgca    17160
ggtgctgttt ccacttgccg ggacgccgca gcgccctccg tgtccgccag acaggcgcat    17220
agcagcggct gcgcccgctc catcaagtgc tccgccaatt gcctgatggt ggagcactca    17280
```

```
aacagaatgg cgcgactgag tttgaagtcg ccttgaggcg atagctgcgc cgcaatgtcc  17340
gtgctgatct gaatgctggc gacgctgtcg agacctttgt ccagcaggtt gtcgtcgtct  17400
ttcaccgctt ttagaccgct atgccggcgc acgatgtccc gcagccagcg tcgcgtttgc  17460
gcttccagct caacgctatc cccctgcgcc agcggcgatt gctcgaccac ttcgggctca  17520
cttgccgatt gcggcgcgtc catgtcgcct cgtaacgcat tcattcccgc cgccgcgccc  17580
tcatagatca ccaaatggcg ctcccccgcc gccaggcgg ataacatgcg ttcacaggcc  17640
ggctgtggct ccatcgggcg cagaccggag tcatcctgag ccatttgcat gccttgggaa  17700
cgccatagcc cccaggcgaa gctgcaccag tttggaagca gctccgaggc cagctcgacg  17760
aactcgttgg cggctccgta agcgctctgc cccacattgc cgagggtcgc cgtcagcgag  17820
ctgaagttga ccacatactg aggctgataa tcctgttgca acgccgccag attcaagacc  17880
acgccgactt tggcgcgcag cgttcggtgc agacgttccg cagtcaggtt atgaaacaga  17940
cagtcgtcca gggttcccgc cagattaaac accgctttga tggcgccgaa tccctgctcg  18000
atatgggtga agccgccctt gagcacgccg taatccgtgg cgtcgacgcg cagatagctt  18060
tttacgccat aggccttcag cgtttgcgtc aacccggcgt cgggcgcctt gcggcccagc  18120
acgaacagat tcagccgccg cgtggactgc aacacgcgaa tcagctcctg ccaacgcct  18180 cccgcgccgc cgatcagcac gatattctcg ccgtcacgaa acggcgttag cgtcggcgcg  18240
ccctgcccgg cggcgaccca ggattcaacg cgcaggcccg tcccgtcaaa gcgcagacga  18300
cgccccggcc aggccagccc ggcggcgata taagccggca atgcggcgcc aatgggacca  18360
gcgggaatgc gcgcggacgt gaactggcag cgggacgttt ccaggctggc ggagcgcgcc  18420
aggccgtcga acaaggcggc aagcgcgtct tgctgcgaat gcaaagatag cagatggatc  18480
tgacgcttct gcgcgaatag ccagcgcagc agctcaaggc tgcgacgact gcaggacatc  18540
cagctcccct cggtcagcga cgccagaggc cggtcgcgac cggcgatcac cgccaccaca  18600
tcgcggccgc cgccaatctc ggtcaacctc gcctgcatac ccgcctcgtc cggaacctga  18660
tccagacgca acaccgctgc gcccatgtgg cgcgccgcgg tcgccgcttc ggcgcagtcc  18720
gtcgccacca gcactcgctc cgcttgaatt tcgccgtggg gaggcgcggc gacctccgtc  18780
aattgccgtc ttaatatttc cattcaaaca ccactgtaaa tatgctttga gtcttccgtc  18840
accgacgagc caggtatctt ttctgtgaag ggacgcgatg ctccgggagg gattgcgcct  18900
gcgctcagac agggtcagcg aatgtaacgc ccatccagat atttcatcgc cagatccaga  18960
taattggggt actcggaatg tcggatcagc tcgaaaaaga acatttcccg ggtgatcaat  19020
tgcacgccgt tttgctcaag ccgccgcaac gccgcctcgt gatcggtgcg cgagcgcgcg  19080
gagcaggtgt ccgccagcag aaacacctct ttcccctgag cttttaaacg caacgcggat  19140
tgcagcaggc agacgtgggt ttccgccccc gccagcacgt agtggtcccg cctggcggct  19200
tccacagaat gggcgacggc ctgttcctgc atgaaatcaa agtgggtttt ctccagaaat  19260
tccgcgtccc tggccacctc ggtcagcgat tgcgacaact tgccgagctt tttgtgctcg  19320
atgatctggg tgggaacctg cagatcgcaa cacatgtccg ccagccagcg gcagtcgttc  19380
aataattgag tgccgttttg cagcagcgga atcaactcca actgcatgtt gaaaataacc  19440
acagacgctt tttcttttg tagcaacatt gttcgactcc tttaaaccat taagtccttg  19500
atgaatttgt gcgattgctc tttatgcagg atagcgcct tggccacccg gaagatagcc  19560
tcgccgatcc aggaggcgac ttttcgccg ggcttgttca cccccataat gtccttgatg  19620
```

-continued

```
actttgaact gcacataagc aagggtgttg tcccggtagg gataggcggc gcccagtcga  19680
tctgcgatca ccatggcgga gacaatggcg ccttcgtgtc cggtcaggct ggtgtcggta  19740
ccgcagaacc aaaggttatt aacgccctga atctctttga tgcgggtctt gcgatagaaa  19800
tccaccggtc tgagtttggg caatttccat gatctttcgc aggcgatgcg ctccggcctg  19860
atactgtctt tcgggtcgaa agtgaccagc aacggcttgt ccaggttccg atacggcggc  19920
agcacgttat tgacccgggt cagggtcccg aactgcgcct ccggcgctgc gatattgaag  19980
ctgtccggca ttttgaactg acaatagtgc ccctctccct ggggactgat ccagcgctcg  20040
tcatgatgca gaaaactctt caccggcaca tgctcgaagc cgcccagaat gtcctggtac  20100
aggctttccg tcgtcgccag tatggacagc gttacgtcag cgtgggtggc gaatatcact  20160
tggtcgaagc gctggctctt cccgttgaac tccacggtga cgcccgaggc ggacggagtg  20220
acgcgctgca ccggcgtatt cagttgcacc cgctcgccca actcctcggc gatgcgcttc  20280
aggtagccgt tcaccccgcc tttggccttg cgccagtagc ccggtgaaaa gaacgacagc  20340
agattcatgt taaaggagat ggcgacgtac atgagcgtgt aatccaggga cggcgcgttg  20400
cagccggaat acaccgtcat cagcggcgac agcgcctggt gcttgaaggc gtccgaataa  20460
ccttgttcat ccagatactg gccgatgctc attttcttgt agcgctcgtc cccggagctc  20520
agcacggtgg ccatgtccag atgaaaacga tcgaattcct cgcgcagttc ttcccccaat  20580
tcgcccttac cggtgaggtt gttccagaag cgcccttccc cggaaaaatc cacgtgcatg  20640
gtcagcggcg ccacatagct gtcgacgccg aaatgcgtca gcaacgcgca caagttgggc  20700
gacaggcgct cgttgaaata ctccacccc atatcgatat actgcgttcc cgtctcggtt  20760
tcgacaggat gactgtaggc gtggccgccg agatagtcgc tggcttcgaa cagcgtgacc  20820
tggttgtttt tactgagcag ccacgcggcc attgcgccgg cgccgccccc gccgatgacg  20880
gcgatgttgc ttcctttcat tttgattacc tctatgggtt aagcctgtgc gtgcgttgcg  20940
accgcatgct gaattttctcc ctgcaggttg gtaagcaccc gacccggtcc cagttcgaca  21000
aaacgcgcct gcggataacg ccgcaacaga ctctgaatgg tcagcgacca gcgcacgggt  21060
tttaccagct gaaaagccat tcttcgata aggtgttcac cgctgatagc gtcgccactg  21120
gcgctggaaa tcaccgtctt ctgcggcgca tggagatcga gccccagcaa aaattcagtg  21180
aattccaccc ggcagggctc catgtagcgg gaatgaaacg cgccgctgac cggcaacgac  21240
acacagcgaa gcccgtcctt ttccagtcgc ggagataact gccgcatgcg cgcttcctgg  21300
ccgctcaaca ccacttggcc cggagcgtta tcgttggcca catccacatc aaaacagtcg  21360
agctggatca gcttttcccg caacctgtcg gcgctgacgc ccagcaccgc caacatgccg  21420
ccgccatgaa tcgcctgcat cagttccccg cgtttggcga cgatgcgcag cccggtcatc  21480
agatcgaaca ctcccgctgc gaacagcgcc ggaaacagcc ccaggctgtg cccgagcagg  21540
cgcccgtcaa atgagtcatg aaaacggcgg ccggcctgcc gcaggtagtc caggtaggtc  21600
aggcagcaca caaagtacag cgccggctgc gtataggcgg tctgattcaa acgcccttcc  21660
cggtcttgca gacacaggtc caccaggtcg taacccagga tctcctccgc gtcgcgacac  21720
tgcgtcgggt agcgctcgaa caggtctttc cccatgcccg gatgttgcga tccctgaccg  21780
ggaaacatca gtatttccat tgtttcaaca cttccatcgt tgtggtttta caggctgctt  21840
caaagcaggt tgaactccgg cgtcagctga gatcaaagac ctcaaagcgg ggctccggcc  21900
gcacctgtcg ggggcgcgta tcgacgtcgt cttcggcgtc tggccgcacc accacgaca  21960
ccatgtcttc cagcaggatc agcacctctc cctgtctgtc cgtgaagtag aaatcaaagc  22020
```

```
gtctggcctt gctggcctga ccggaagttc tctccaggca atagccgtac accgcctcgt   22080
tgtccggcag gcgtttcacc actaaccgac ccaggtggta tggcataaag accgtccct   22140 cgccgctgct ctcagcgccg aacccgccg ccagaatcgc cagttgcaga cctgaatcca   22200
gcagcgccgg agacaccagc cgcccccagt cgtggtcgac ctgcagcaac gccctcacca   22260
ggcccggttt gacctgcgcc cagcgtatcc cctgcagggg cgcgccatag tcataacccc   22320
gttgtttgaa gtccgcataa atctgcgcct gggacagacg cgggatggcg cccatctcct   22380
gcagcggatt tggcgggttt tccatgccca gtcgcgccag cacggcggcg atattcgctg   22440
gcgcgctggc gtcaggggtc cgctccgcgc tgcaatactg ggtatagccg ccgcgcccta   22500
cgaaaagcgt acgctcgccc tcttcaatca cgtccaccca ctgcgggtcg gtgatcttgt   22560 cttccacat aatgttggcg aaaccgccgt catcggcgct ttcacacagg gtcgacaggg   22620
tccaggcggc gggcgccatg gcgcggccat tgatgcgatg ggcttgagtc agagaagtga   22680
agcccttgaa gttggattca accgagtcga tccagtgacg atgacggatg aatacatatg   22740
gcgggaccgc cgccagacgc cgctgcggat agaaatcgcg ccagggcaaa tcgcccccgg   22800
cctcatacaa ggcggcgacg cgctcggcgt tgtcgcgggt caaccgctgc ggcggctgtt   22860
cctgtaatgg tcccgacgcc tctttgcggg acgcagcggt aacgacttgc aagtcctgac   22920
ccagttgctc aatcaggtca gcctgatcgc gacacaccaa cgcccggcgg aagcgatcat   22980
gatcccgcgc gcacgccagc gtatacgcca aagcgtccat atccacctgc cgcccctgca   23040
accactcccg caagctgtcc atggtctgct gcaatcctgc gttacagtga tgggacagcg   23100
gaatcacata gctatcccgc gccgcacgag gcgccgcatc gacggacgcc tgggccacgc   23160
cctgaatcac tacatgggcg ttgccgccgc cggcgccgaa cgaactaacg gcggaaaccc   23220
tgggcgccgt tgcgtcccat acccgccgct cccggttcag caggaacgga gtctgagtga   23280
agtccagatg gggattgagt tgctccgcgt gcaaagaagg aacccactcg ccgtgatgca   23340
tctgcagaac tgcttttagc acgccgcaaa gtcccgccgc cgattccaga tggcccaggt   23400
tcgacttgac cgaccccaga cgaatactct ggggcgctgc gtctccgtag cttttgctta   23460
atgcgcgcag ctcgatagga tcgcccagct ccgtgccggt gccgtgcgct tccacatagc   23520
ccacctcctg cggggatacg ccggcggcac gcagcgcttt gccgatcaac gccgcctgag   23580
cctccgggtt gggcgcggtg tagccgttgg agcggccgcc tgcgttaatg gcggagcctt   23640
tgataaaggc gtaaacgcga tccttgtcgc gaatggcgtc ctccgcccgc ttcaccacca   23700
gacagaccac gccttcgccg tcgacaaagc cgtccgcatt ggcgccgaat ggcttgcact   23760
gttcgctgcg ggacagcatg tgtaagccgc atagcagctc ataatgacgg ggatgggtaa   23820
tcaggttcac cccgcccacc accgcctgtt cgcagtcgcc gtttttcagc gcctggcagg   23880
ccagatgcaa ggcggtcagc gaggcggagc acgccgtgtc caccgccatg ctggggccgc   23940
gccagtcaaa gaaataggat gcgcggttgg ccatggacca gaacagggag gtcgccggcg   24000
ctgtcgtcgt ttgcgccggg gtgtgccagg cgtaatcgcc gttcatcacg cctacgaaca   24060
ccgcggtgtc gctacccgcc cactgcttgc gggtgtagcc cgcgtccagc atggaacggt   24120
aggtctgctc cagcattatc cgctcttgcg gatccattct ggcggcttcg ttgggcgtca   24180
gattgaagaa cacatggtcg aaggcgtcca cgtcgtcaat gaacgcgccg cgattggtgt   24240
agctgccgcg gccgttaaga ggagcttcgc tgaggaatcc ctcctgcttc cagcgctccg   24300
ccggaatcac atcggtgcag tcgcggccat tgcgcagatt ttcccaaaaa cgcgccacgt   24360
```

```
cctgcgcctt cggtaaccgc gccgccatgc cgacaatggc gatatcgccg gggcgccaca   24420 gcgattttc tggcgcatca gaggatggct gcgcatcctg tgcgcgctca tctgtaccac    24480
tattgcctgc acattcccct gtctcagaag cccgggctgg agagctgtca ggcgtggtct   24540
cgcctgaagg tgaagtcgcc accgtggtcg ccagataggc cgccagctgg cgcaggctgg   24600
ggtattcaaa cagcaccgtc gcaggcaggt agccgaatat ctccttcaac ggacgaatca   24660
gttccaggga aataatggaa tcgacgccgt actcctgaaa cggcgtatcc gcctcgacat   24720
cttcgggctc catcatcatg gtgtctgcaa tcacggcgcg gacttggttc atgatttccg   24780
tcaggctatc ccggccgggc ggcgtgaccg ccgtttcttc gacagtcaga gccgcagccg   24840
tcgcttggtt cgtggcccct tcatcccagg ccagtccgga ggccactata tgctccgcca   24900
actggcggat ggtgggatac tcaaacagaa tggtcgcggg cagatatccc gttttttcct   24960
tgatcggctt caacagctcc atggagatca acagtccac gcccatttca ctgaagggca    25020
tatcgcgctc gatttcactg ggtcgaatt gcagcacctc ggcgatcgcc tgctgcaaga    25080
acgcttcaat ggacgcctga ctggcgactc cggcttgaga cgcgctttgc tccgccgcac   25140
tgtcaggcga cggctggatg ggggaagctt ccgtctgagg cgccgtgttt tgtgacacag   25200
cgccttgctg cgcatcggct ccggcgaagc cgaccatcac ctgctgatct cgccgccgt    25260 gggcgtccac gccctggaat cccgcctgca acatcagacg tcgccaactg tcgccggaca   25320
gcagtgggct gttggggatg cgataagggt cctggctcag ccaccagccg tccgtcaggc   25380
cgaaggtcaa cgtggcgtaa tcctgacagg aagtgatttc attgagcacg aacacgccgt   25440
cgtccgccaa caaccgacgc acctgacgca gggtttccgg caggtccgag gtagcgtgaa   25500
tgacgttggt ggcgatcacc acgtcgaagg gctgttcaaa cgcaggggc ttctcaatat    25560 tacagatttt gtattccaca aagggatagt cagcgaagcg gcgtctggct ttgttcaaaa   25620
acgcgaaaga caggtcggtg aaggtgtagc tgacgttgtc cggcgtcagt tcaggcagca   25680
caaactgagt ggtgctgccg gtgccggcgc cgatttcgat aatgcgtaga ggacgtcccg   25740
cccgcgcctt ttgcaagttg gcgacgatcc tggcgaccac ctgattgaag tagtccgcga   25800
tgggattgtc ccggtacacc ggctccacca gctcaaagcc gccatcgggg aaaatcacgc   25860
tcagcgggtt ggtctcccca cgcagaatgg cgggcagatt gtcgatgcac tgatccagca   25920
gccgaatatg accttcagc tctggataga ggtctatgac ttgctcgcgg ccgggtgaat    25980
gccccgcgtg aatacttctg agcgccgccg ccagcttgcc gaacttgggc gcaatggttt   26040
ccggcatagg cgtttggctc aagcgccagc gcgcgtattc ctgcaaggcg gcggacatgg   26100
cttcattgcg ggcgaccaac gggtcctgtg tgcgatacgc cgggatcagg tcagcgccgg   26160
ttgcaggtgc ggcgggttcc tgggccttga gttggggaga ggtttgagcc attacgtttt   26220
gaggcattag tttttgaact gcggtatgag gagcgatatg caggcgtttt aacgccagat   26280
cagacgcttt caccacggtg atttgtcggc gctccgtcac cagaaaacgt tcaatgacgg   26340
cgagtccttc gtccacttca atagagccga tttgcagctt cttcatgcgc tcccggtagg   26400
tctcggaggc caccacgccc accgagcccc aatagcccca gttgatgacc ttgctgttga   26460
tcatcagtcc gttgtgcagc aaatccgcga aggcgtcttt cgccacgcag gcggcggtgt   26520
aattgccctg cccggggtta gcgatataag actgaatgga agagaaaaac aggcagaaat   26580
ccagggtccg ccctttcaac gcccgcgcca gattgtaggc gccatgcacc ttcggccgca   26640
gcacattgaa cagcgtctgc tcggacatcg ccgccagcga cgcatcctcc agcaccgagg   26700
cggaatgcac tacgccatga atcacggcgt attggtccag caccgtctgc aatgcggcgc   26760
```

```
ggtcgctgag atcgacggag tgataatgcg cctcggcggc gcccagatcg cgcagtcgca    26820
tcagcaggtc gtgcgcctca gatcgacgtc cgagaatcac cagccgcgcc tgatagcgag    26880
cggccagata ttccgccagt ttgccgccca acccgccggc gccgccgaga atcacatagg    26940
ttccctgctg gcgaaaagcg gattgcgccg gccatgggtt caaggtcgtc ggctgcatgt    27000
cggcgacgcc atagcgtccg tctgcgatac agaccggcgt tccggggtgt gtcggaagcg    27060
atatgcgcaa caggtcttgc agcacgtccg ccgtcagctt ttgcagcgag aagctgcgca    27120
cggtccattc cggccgctct ttggccaggg tctgcgccag ccccacatag acgccgtcca    27180
caggatgggt gacgctctcg aacagcgggc tggcgacagc tttgtccgtg aacacgtcca    27240
gtttgaccgc gggtttgtca cgcagcgctt tgagcagatg gaaaaaggcg ctgacgtcct    27300
cgtccggcac ggcggcgcgc cagggagtac gggtgacgaa acacaggcgc agcgcggggt    27360
ttttatccac cgcccgcgcc agatcgtcaa tggtttgagg gtccagcagg cgcacttccg    27420
cctggggcgt ataatcggcg atttcctcgc gcagcgctgc ctgcgatggc ggaacaataa    27480
tgacccaggg cgcctccgcc ccggacgccg ccgccaaagg caggattttc cattcgggag    27540
aaaacaccag cgaatcgata gccgtttgag aaattccggc aaactccata tccctcatac    27600
tcctttattg taaatgtgat ggtttgacgc ccaggtcaaa aacagacagc aagggggtgt    27660
aggcttcgtc aaaaacagtg aggttggtgc gaaacggaga cagtttctcc gtcagcacga    27720
aggcgctgcc caaagcctgt tcaggcagcg cttgatgtaa ggtcagccgg cccagggaat    27780
atggcatcag actctccctg cgctcgccga tggaaatcgc cataccagcc tgaaacgcgc    27840
agtccagcag gccggcccat cccagaaaaa cgccgtcgta attgctcagc caggacagcg    27900
ccttgttgga caggcgctgc acgtagctga tgcgttgaaa gtaagggccg tagacgatcc    27960
ccatatcggc gaaggcggcg tagacctcgc ttcgcggaaa gtggtcccgg gtctccgcgc    28020
cgacctgact gcgtacgcat aaaggcgtcg ccaatgcctc cgtgcgcccg gatacggttt    28080
gtgcgttcag gacgccgccg ccgcacacct cgccgccgtg tgcaatgcga aactcaatgc    28140
gcgtcgggct gatcggcgcc agttgcacgt cgatctccgt ctccggcgta ttggcgagaa    28200
ccgggcgcag ccagaccact tcatcgacaa aacaggtatt aaaatccggc cgcgccctgg    28260
cgacggcgct caaggccagc tccagataca ccacgccagg caggaccttc cagccgcgca    28320
cgcgatggtg tgaaaaatac ggatgatcgt ctcgcagggc gacgcgatag ccatcgccgg    28380
caggcagcct gcgccaacgt ccttgcgtgt cgaaaaatga atctccggct ctaacgcttg    28440
tgctcatcat cggtctcgcc atccttagct gtggttttca tttgcgccaa tcccgtctgg    28500
ttcttggcgt acccccctgt caggctcttg gtataccaat agtcgcgttc gtcgaattga    28560
taagtcggca gcctcatttt gactgcgtcg gcgccctcat acagacgcgt ccagtcaacc    28620
tgaagcccct tcagatatcg cgctcgcgca tgggccaata tcgccggatc gttcagcccg    28680
ccgggatcca tcgtctcgtg cagggcctga ccttccgcag tttgttcatt tgcggacgga    28740
ctgtgtcgtg gcgcgtgcac gccggcgtgg ccggaacgca gttgcatcaa taactcatcc    28800
accccgctta ccaaccaggc gtgtcgatat tcgaaatgtt cgcggccgca gctcaggctg    28860
aaggccagat cagtcaagcc gcgcatcgtc agctcagcgc ggcgttccgc cacaaaacgc    28920
gccagggtcg ccatattttt ctgcagcgcg ctttcgctgc gggcggaaat gggaattaga    28980
taagtgtcat agtgattcgc agcaggccgc tcctggcgcg gcggcgcgga cagaaccacg    29040
tgggcgttgg cgccgccaaa accaaaggag ctgactcccg ccgtcagcgg ttgctcgctg    29100
```

```
cgccagggaa tgctgtccgc caacacctga aacggcgacg aggacaggtc gatctccggg   29160
ttcagttgct ggaagtgcac attggcgggc agccgttggt gctcgaacgc tttgatgact   29220
ttcaccactg acgccacgcc agccgccggc tccagatggc cgatgttgga tttcaccgcg   29280
ccgagccaga ccgtttgtgc ggcattgccg ccggtcaatt cctgtaaggc ccgcttcagc   29340
gccgccactt cgatgggatc gcccaggcga gtgccggtgc cgtgggtttc gatatagctg   29400
agccgctgcg ccagttccgg cgtataagcg tccagcaaca gccgatactg ggcgttggga   29460
ttaggcgccg tcagggaatt ggccttgccg ccatggtttt ccgccacgct ttcaatcacc   29520
gcgagaataa ggtccccgtc cgcctgcgcg tcctgcaagc gtttcaccag aaagcagccc   29580
acgccttccc ctcttacgta gccattggcg ctggcgtcga aagtagcgca acggctgtcc   29640
ggggacataa agcgccccgc ttccagtcct tcgttgatct gcgcatccag gatcagattg   29700
acgcctccca ccatggcggc gtcgcagacc tgggcttgca gatcccgaca ggccttcacc   29760
aatgcggtca gcgccccgga gcaggccgtg tccaaagtaa acgatggacc gttccaatca   29820
aaaaaactgg aaatacggtt ggccaggatg ctcagggaat gtcccgacag agagtacggc   29880
gtctgttttt caccgtcgcg ggcctgcagt aacgcatagt cgctaccggt ggccgccata   29940
taacatccga tgcggccgcc ggataaatgg gacggcgcat agcccgcatc ctccagcgct   30000
ttccaggcgg cctgcagcaa caggcgctga cgcgggtcca tcctggtggc ctcaaggggg   30060
gaaatggaga agaagcgcgc atcgaatcct ctgaccgagg aaataaatcc cgcgcgatag   30120
cccggcaaag accggtccgc aggcgcggcg gcgatacagt ccttgcggtc cagcaacgcg   30180
cgccaaaagg tttccgcgtc gtccccgccc ggtaaggtgg ccgccatgcc gacgatagcc   30240
agtctgtcat ccccgttgcg ctcctggcga cgatccatcc cggacgtttg cggcctggcg   30300
ccctgctgcg gcgactgacg ctgacggatc gccccggcca cctcgttgat ggtgttgaac   30360
tgataaaact catagctgcg aaacgtaata tcgaaacgtt gttgtatcgc cgccgccagc   30420
aggttgtaac tgatggaatt cagccccagc catcccaggg gttgatcaag gtcaggcgcg   30480
gcgacatcca gttttttccag cagtatgttc tgtatcgcct gctgaatcac ctgctcttgc   30540
gcagccgttg gtcgcggcgt cgcgacgacg gacgagggct gcgtcataag cggcagctcc   30600
gtcatcggcg cttcgctcag gaatttgacg tccgctttgc cgttggcggt cagaggaata   30660
cggctcaaac gatgtagcgc tttcggcgtc atgtaataag gcaaggtgcg tcgacaccaa   30720
tgcagcgcca cgtcgacatc gaacccacta ttctccggag cccagacaaa gcaacacagg   30780
tgagcttccg gcttatgtct gaccacggtg aaaaaggccg cgtccggggc gaactctttta   30840 aggcggtgac tcacttcgcc agtgtcgacc cgatagccgt tcactttgta ctgactatcc   30900
cgacgaccga cgtattcgat gtcctgatgg gacaggtaat gcacgatatc gccggtttta   30960
taggcgcgga cgccattggg cagagtgata aaagcctgct ctgagggcgc gttcaaatag   31020
cctttgccga cgcactcccc cgcgatggtc aattcaccct gcatccctgg cgtcacggaa   31080
tcgcccttgg catccagaat atagtattcg ctgttgagca ccgggcgccc caaaggaatt   31140
cgccccgcct ccgtcaccct gcggcaactg gcccagatcg tcgcctcggt ggggccatac   31200
atgttgtaga gccgcccggt ctgttgcagc aggtattgcg ccagttcttt atccaaggct   31260
tcgccgccgc acagaatggt taactcccct gtcgcgcgcc aacccgcttg ctgcagcatt   31320
cgccaggtcg acggcgtcgc ctgggccacg tctaccttgt gctgattcag cgcctctccc   31380
agcaattcgg cgctcagccg ggtttggtcg gacacaatat gcacttcgcc gccgcacatg   31440
agcggcaata gcaactccag aatggagata tcgaagctga tgggggttag cgccagcata   31500
```

```
cgttcaccgg gctgaaagcc aggaacgccc tgcatcgcca cgagaaaatt cgccagattg   31560
cgcgcgctga tcgccacgcc cttgggtcgg cccgtggacc ccgaggtgaa catcacatag   31620
gcggtctcat ccaggtgcgc gtccgccgcc agagcgtgct ccagctcgtc ttccgcgccc   31680
gccgacgctg tcgtcgccat atggatagac gactcgacat cgataagcgg cgcgccggga   31740
aacagcgccg ccgctctggc gcgcgtgccg ccatccacca atatgacgcc gacattggac   31800
acgtccatca tgtagccgag ccgttcatcc ggcagcaacg ggtccatggg cgtaaacgcg   31860
cgttgggacg ccaaggcgcc gagataagcc accggcgccg ccgccgtacg ctccacaaat   31920
acgcctatgg cggaggacgc agcagcgcta gctgaactat ctgaatgcgc cgcgatgtcg   31980
cgatacaagc gtccgatggc ggcataggtt tgacggtagg tcagacttgt ccgctcatca   32040
ctgacagcag gcgcattggc ctgtagcctg gcggcgttcg ccacccttc cagaatacgt   32100 acttggggcg ccgcctcgtt gcgttcgccg cagataaccg gcgtcaaagg ctggctgaga   32160
ctgcattcat gcagcggtcg ctctggcgat gcggcgatat aggccgcgac tttgacaaag   32220
ttatccgcca gcgacgtcaa ggtttccctg acacaaagc gggatgacga atcgaaggac   32280
agcaacaatt gctcgccatc gcaactgtag ttgatggcga gatcattcgg acctcctgta   32340
tgcgggggct cggtcagctc cactttgcac cccgccattt ccggcgccgc ataaggcacg   32400
agtccgtcag aggcgttcac caccagatta aacaaacggc cagcgtgatt ggcgcgcggg   32460
tccgcccact caatcaattg ctgcgtaggc gtgtgttgat gctcacgcac agcttcgcgc   32520
gcctgtttga cgccggcaag cagtccggcc cctgattggg cgggatcagc cttgatgaat   32580
agcggaatca gattggtgta acagccgtag gcctggcgct cgccgcggca attgaccgta   32640
tgggcgatag tgacagcttc ttcgtcatgt tcttgggtcg ctgagtacaa cctgatgact   32700
gcggcggtaa ccgcgacgac atactggaac aaagtaacgc cgcatccttc cagcatggcg   32760
ctaatggaag cgaagcgatc tccatccaga gcaggttcga cggcctgcgt tcgcttattt   32820
atccccagcg ttcgtttaac agctaacgtt cgtttaacag aaagatacac gccttttcc   32880 ttcggcgttt tgtagcaaaa cggcagcggt tgaaacaaac gcgcgccatg caaagcttcc   32940
ttccaaaagt cgacagacga cggtgcaacc ggagcgtcgc cgatggggag aaacgatatg   33000
cccccctcat ccctggcttc gccatgcccg ccttcgcgac gatgccaata gtccgcaaat   33060
gtatttaaaa atggctgata acactcaccg tcaaacacaa ggtgactgaa ctcaaatttc   33120
aagcctgtga tactttcatt ttcaataaaa caagcaaacc tgaacagttt gtcgcccgct   33180
ggatcaatcg gctctaagtt actccattcg gctttatcgg taatgatatc caccacttta   33240
tccggcaatg gattacatcc gactaaaagg ctgccgcctc tatctaaaaa ataacttaac   33300
aggccattaa atccatttaa aagcacggct ttcaaagctc tgtttaatgc ctggaattca   33360
atgtttccag tgattttaaa ttggtagctt aatgtcagac ctgggtcgtc agggttacgt   33420
cgatagcgca gccactgaaa ctgttcataa tgggttgctt tacgtaattt catgaaattt   33480
tctcaagcat taaaatccct aatttcactt gatacgatgc ctacgcaaag ttgcagggaa   33540
caactagcga caaaacaaca gccgaaggaa acagcacgca atcgccgttc ctctcagaag   33600
cgttggaaat atttgaatgg cctacgccat ccgcgtaaaa caagcctacc agcgcccaga   33660
tagattctaa gcacctgttt ttattggctt atttcactga gattaaattg caggcggacg   33720
agtgcgcctt ggcgaaaatg ggaagcgtac atccatcact tactctactc ctcgcggggg   33780
aaccccagct tgatacccet caagtcacaa tattgatatg agactgtgtg caaaaaaga   33840
```

```
aagtatactt tcctttaagt acataacacc tgaaaacatc ctaattctgc tatgttttca    33900
gtgaaaattt tatgaattta acattacaaa atattaggaa ctggatgcat caatgcactc    33960
tcttagcgcg acaaccaccg tgtgtaatgc atgtcacatc agtcaatata cagccaactt    34020
ctacagacca tttttagcca attgttcaca aatggccagc tcacgttagc gcattattta    34080
aaacagttca accggtaaag aacaaggtta ttaatacttg ggaacgttta cttaaattga    34140
tctgatatta atttgatttc acgcactctt ttaaatttta tatttgtcaa ccgtaaaaaa    34200
taacgttgcg cagcatgaat tggctaccaa tagcggatta tctataaaca tagtagctct    34260
atttataatc aatattaaaa attagttaac aaatacacgc cattcaagtc acaacatcac    34320
ctcaactttt caacgctcca gcgccacggc gcccactctc taacagagac gcaacctcac    34380
cggcccgtac acgcaggatc gccagcaagc ccaaccaggc gaagtacgaa agaagcggca    34440
aagcgccata tgcatgtcgt tgtgaagtat tggcggccgt agtcgtgtta attggcccgg    34500
gttctggtgg gctttcgaga cagccccagg cttacgcttt tttgctagct ccgaattacg    34560
aagacgtctg gtatgatccg aaggtgttaa acgcctctta ggcgagcatc ctaacaacaa    34620
aaatcacgga gtctggcgag atgcatatcg ggccgaagtt tttacttgcc gccatcagaa    34680
gaagaatcaa agacgagggg ctgagttacg gttatttgtc agagaagacc ggcatcccgc    34740
tctcaagtat caaacgtcac ctgcataatc cgtccctggg gctggacaag attctcatgt    34800
acgtcagctt tctcaatacc gatctggtgg agctgaccaa gctcgccaac aaactgcagc    34860
acgagaacga gctgtttatt tctgacaaac agagcgagct gtttctggag cacccctatc    34920
tgctcgactt catcaatatg gtgacctccc ataaatgac gccggatgcg gtggcggaga    34980
aatacggcct cagcgagacc agtctgcgct tctatctgcg catcgctgaa atccttggct    35040
atatcgatga ctttggcgac ggctcttttt atcagtccgg acgccgctat ctactggaag    35100
aaggctccgc cttggacagc ctgtttcgtc gccgctttca ggaagaatcc ctctcccacc    35160
ccatccaccc cggcgtctgc gttggccgca tcagaatgac ggaagcgcag agaatccagc    35220
tcgaagacga cctttacgac aaactgatcg aactcaacgc agtcaactcc tccaacgacg    35280
aaggcgaacc caccaacgta ctcatgcgct gcaccccagg caaactgacc cagttttccg    35340
atggcctgcc ggatatcgac gggcaactgc tgaagtatgt gtcggagttg tttgctaagg    35400
cttagtgggg atgatttggc gtgatcgtgc agggagggcg tggttattgg aatgctgcct    35460
ggcttgacct tcttgcaacc ttcgtagcag ggccttcaaa gaggggcaga acgggttaat    35520
ccgacattgc gttgagtggc gaaaacaaga agagttggct cactaataac actgattatt    35580
ttaatccaat aaacctaaag gccttatcag attcagtgta gtcgccaatt gattgagcgg    35640
catgaattcg acttcctacg gatataaagt tatagccgag tgcttcggac gctctccaat    35700
cccaaggccc atcgccaaag tatgttttag agtcgtaact ccctgtgctt gcgcgcattt    35760
cagccaccct catgatctcc gtcctgctat agtggtctga ggatgaagcc atcgctatcc    35820
ctggaaggct gatgccgacc gcgtccagct tcatcctggc ggtttcggcc caaccacctg    35880
tcgcaaaagc tatcgccaca tcctgacgtt ttacgagccg tgacaaaaat tcaaccgccc    35940
cacaaattgg agacagttca tggcgcgaaa tatattcttc tacacgtcta acgaattgtg    36000
cttttacatc gaaaaaaata cgctcccgtt ctctctgaag accgacttct tcaattatct    36060
ctgagagaat tccagcgtcc gttacatgcc gaaaccgacc ccagtcaggg ccaaccgaaa    36120
taccaaccac atctttgacg gcagcctgaa aacactccgt gtcgaagtcg taggattcga    36180
ccaacgttcc gtctatgtca aacatgacta gatgcacgtc ctctcccccta actatcaaat    36240
```

```
tgctgtctga tcacctgcca ctgctcccat gccttctcgg gatcgatatc tgaatacccc   36300
ctcgattcct caagcgctct tacctgatga atcgtaccca tctggcatgt ggcgctatct   36360
cttatttcga taacttcatc ttctgtaaga ggttcgcctt tttcacgctc tttattgagg   36420
agcaccgcca ccaatgccgg aatcggtatt ggaattagat catccgccat ctgtcaccta   36480
ccatttttag ctatttagcc ctataaacca gatcatccac tcgctaaata cgaattcaat   36540
gaaatactct gtagcagaga atccccggaa accttggcat aagcgagcaa agtagcgaat   36600
ttgagatatt gagcgccatt ttcacctctc atggcggaaa atatgcacaa ttattaacca   36660
catagtgcga cttgcctgga ttacgcccct ttcctcaaac cctttttag taaacatttc    36720 gtcgatttct ttcgcagtca tatctttgaa agggttaccg aggcctttac tccttgtaac   36780
ctcaaattat tgagtaaatg taatagcact gcacttttcc gcaatatctc gctgcttgat   36840
ttctgaaccg agagcaacca gttgtactat tactgagcga gattcagtac ttttcgcaaa   36900
ttcaagctga attccatcaa agtagccttg ctgattatga agcacccaag accatagcag   36960
cgggcttcca attgctaatg accaaggccg tcttttcata aacgatatgg atttccattt   37020
aggggcaccg caccaatcgt ttggatacag cacaaaactg tcatcctctt ggaccacaat   37080
gtaaaatttt gacttctcga aaatgaattc catcgcgcat aaaacacact cgagactgct   37140
ctcttcacaa ttctcaaaat acccaacaac atctactaac ttttgctcag aatttgcgta   37200
gcttgataat atttgttgat ttacgctcat gcctaatatt tccgcccttt cattcccgcc   37260
tgcatgataa tcttgagagt agtctccgcg taaagcttcc atatgcttcc tgccaatttt   37320
gttgacatgc tgcggcacta cctgggtgat atggatctgc ttttaaagcc tgggaacaac   37380
cgctaagtgt cttcgtcttt gcaacatcaa aattggtcta tatacgcaaa aactccctcg   37440
tgatgaaaag cccataccga tttgttttt agacttacta ttgcaacatc accattaaag    37500
aaacactcac catactagct caggtggttc ttcacaaagg cttccaattc ttcggctttc   37560
agttgaaatg ggccgttatt atcatcatac gaagcttccg taatcacaaa aacctcacca   37620
tcaataacat gcagctttaa catttcatgc aatatatcca gatcttcaag atcttcccaa   37680
tttgacaagc tatgccagta tatttttatg ttggctgatt caagtgcagc gacaatatcc   37740
tctaacgatc tataatcgaa tccaaaaacag cttttgaaga gagcatgaaa gctctcccaa   37800
aggacaacat tattctcaac atttgtcatc gaaatttctc cggaagtgag agctgtaaga   37860
atatggagag cgataagtta caagctaatg ccgctagctg aatcgggtta ctttgccttt   37920
ttagcactca gatcataggc gaaaccgagg gctaatgctt agcctcatca tctaaatcca   37980
gttctaacgc cgcgaagatg agcccaaagt aagggcgcgc tagtccgtgg ccttggcgcc   38040
caattctcca agccatattt tctctatata tccgggctcc ctaatcgctt tgagctgctg   38100
aactaaacct gaaacaccaa gacttgaaag tgattctggc aggtcgctta caagaaaatc   38160
gaagaccttt gaccaatcgc cttcggtatc cattcttgag tgctcgaagt gcaaaagctg   38220
tgactggtat tttaactttt cgccaaagct attcagcgtt aacttaaatg gatactccat   38280
agggtcgcag tggaacttcc ccttcggcct ttccatatag tcaaagctga ttggtcttgc   38340
gcaaattaca aaagcctttg tccctgcttg ctgaaaccgt ccacttagcc ctatgagccc   38400
tatcacccac tcaccagcgt tcccaaaagc acttgctgtc cctagctgtt caaatcccga   38460
cttttcgagc ttttctatta attcggcatg attcatatct gagtgtgaaa gtctccaaca   38520
ctgtacaagt agtcattgat gcagcgaaag ttgacccgcg cgatttcgta atttacgtgg   38580
```

```
actcactggt ctgcccaaaa tactagcctg acttcgctgt ctggcaaggc gtctgggaac    38640
agggttaagt cgatagccgg gcaacggcca tttgcatctt cttgtaaatg ctttagttcc    38700
gacaccaaca accacgacgg ccggtttgca tcctgccagt actcttttat gaagctcaac    38760
atttcagcgc cgaggtcagc agggaagccc ctttcacccg ataattcgta aatgtctgcg    38820
tatgcgctct tgccccacca atacggagcg acgttcttcg gaactggttt accttcatag    38880
tcctcatctt caacaaggtc atccgcgatg atccactcat cgttgtgatt aatttcaatg    38940
aaggcgaata cgcatgcgcc cataaatccc cgtatatcca acgtttactg aactgaagct    39000
aaccccgaaa tttaacgcca gctgcagaca gcatgaaaaa caaagttca  ctttaaaggc    39060 cttgtcatac gcccaggcct gtaaacagca aaataccaaa acacaacggc tgacacgccg    39120
ccaacaaaac tacagaaaag cgcctggatc aataaggaag ctcagcatc  ctgaccgaaa    39180 ggctttagcc agtatacaaa cacaaaacca ggaagaagcg cgggcgcgat ataccaaatc    39240
agcttatctt tcttcagttt gtttagaagt aaatggccag gaatcgccca gataaccaga    39300
accactagcg ccaccaatgt ggccacgcca gcgattacgg cggatattcg gaaatcgag    39360 aagtcattat taatggagtc aatcactgct gtgagaaata ccagcaaaaa taccgtgagc    39420
agcatggcta agctggctat tagtgtgttc ttcataatat gtacactgat acttacaact    39480
gtaaccctaa cgagctattc aaccacacca atcccaactc cccaaccggt ttttcacccg    39540
acttcaacac cctgcaacga cacaaaatcc agaatgagcc gatgacaggg cgctgtttct    39600
ttagacgaaa ctcaagcttc taatgtttca aaaatcgact cgtcatccac ccaccagtct    39660
cactttctga gaccgccaag ctctgattct gatccttcat attgacgtct tcaaagggtg    39720
ttgagaacga attgtataca atatacattt cgtcgttgca taacgaaaat aatacgacga    39780
ggtagtcatg aagataagca aactactgat gctgggcgct atttctctga taagcagcgt    39840
gtttacggta agcgcagtgg cgaagcccta ccctccagga actcaactcg cagcccgaca    39900
ggaaatcaca ttgaacaacg gtggcgaggt cacgtctgtc gatcccgcca agtatgcggc    39960
ggagcccgct tttaatttgg gtcgcgatct gttcgaaggg ctcgccattc aggacaagac    40020
cggtaaaacc attcccgggg tggcggagag ctggtcggtc aatgacgaca acaccgtcta    40080
taccttcaag ttgcgtcgct cccagtggtc aaacggcgat ccggtgaccg ctcatgactt    40140
tgtttatagc tggcgtcgcc tgctcgatcc taaaaccgcc tcaccctacg cctggttcgc    40200
cgccatgccg aaaatcagga attccgcgaa gatcatgaaa ggtgaagcgg accctgccac    40260
cctcggcgtg cgcgcagtgg atgattacac ctttgaagtc accctggagc aatccgttcc    40320
tttcttcctc aagctcatca gccatccggt attggtccct ttgcatgagg ccaccgtgga    40380
aaaacacggc gccgcgtgga cgcagccggc gaatatcgtc accaatggcg cctttattgt    40440
gtccgagtgg aaagtgaatg aaaaaatggt gctgaagaag aatcctcatt actgggatgc    40500
ggataatgtt gtgctggaaa aaatcacctg gctgcccatc ggcgacgcca atgtggcctt    40560
gaaccgctat ctggccggag agatcgatca ggcgctgtcc attccttccg cgcagaaaaa    40620
gcaactgctc aagaagttcc ctgaagaagt ggccaacacc agcgcctccc tgggctccgt    40680
ctattactac atgaacaccg tcgccggggcc caccaaggat gtgcgcgtgc gcaccgcgct    40740
gtcctacgct gttgatcgcg acatcatgac caaggcgatt ctgaataatg gcggcgtgcc    40800
catgtatacc ctggtgccgc cgcaaactga cggctacaaa ccttacacgc cagagtacgc    40860
cacctggacg cagaagcaac gtaacgaaaa ggccaaacaa ctgctgacgg aagcgggcta    40920
tagcaaggac aagccgctga aactgacctt caccgtgccc acctttttcca ccgacgtgaa    40980
```

```
gatcgccacc gccatggcgg gcatgtggaa gagcgtgctg ggcgtacagg tggagatcaa   41040
acagctggag ccgaaggtgt tctacgccct gaaagagacc ggcgatattc accggggcgg   41100
ctgggtcgcc gactacaacg aagcctcctc ctggctggac gtcttcgtgt cctccggcga   41160
gttcaacgac tccaagtaca gcaacccgcg ctacgaccaa ctcatgcaag cctccaaagt   41220
gctgagcgat ccctccaagg aataccgtga ggcggagacc ctgttgatca cgacatggc   41280 gatcatcccg gtgtatcgct acggcaatga tcaatacctg atcaagccct atatcggcgg   41340
ctatgaacgc accaatccgg aagcctccta ctaccgcaag aacgtgtatg tgaaagccca   41400
ttaattgggc gatctcttgg cctggatgtc ggaagtacag agccggcgcg tccaggcctt   41460
ttttaacgga ttcctgagag cgtcattatg ttgctataca ttttgcgtcg cctgttgatc   41520
gccattccga cgctgctgtt catcgccctg gtgtcgttct ggctgatgca cgtcgctccc   41580
ggcggcccat tcgacatgga gcgtcccatg ccggaaatcg tgcgcgccaa tattgaagcc   41640
aaataccatc tgaacgagcc gttttttcacc cagttttttca tctatattcg cgacttcgta   41700
caaggcgatc tcggaccgag tttcgtgtac caggatttca ccgtgacgca gctggtgggg   41760
caatcctggc ccgtgtcggc gaccctgggc gtgttgtcct tctgcatctc cgtgccggtg   41820
ggcttgctgc tgggaaccct ggcggcgttc aatcgcaaca gcaagctcga ctactttctg   41880
atgtcattgt ccatgaccgg ggtggtgatt cccgccttcg tgctggcgcc ggtgctggtc   41940
gcgatcttcg ccatacgcct ggattggttg cccgccggcg gctgggaggg cggcaaagcg   42000
gcctttctga ttctgcccgt cctgagtctc gccatcggct ccgtgccag catcgcccgg   42060 gtcatgcgcg cgccatgat cgagacgtta aaccagcctt atatccgcac cgccatcgcc   42120
aaaggtctct ccacgcccta tctgctgttt catcatgccc tgcggccgtc gttgatccct   42180
gtggtggcga tgttaggccc ggcgtttgtc gcggtggtca ccggatcagt gattatcgat   42240
attttcttcg gcaccggcgg catggggcag cacttcgtct ccggcgcgct gaaccgggac   42300 tatgactgg tgatgggcat caccctgatc gtggcttcgc tgaccatctt tttcaatctg   42360
gtggtggacc tgctgtacac cgtcatcgac ccgcgcattc gcatttagga ggccgtcgtg   42420
ctgacaacca gaaaactcga cccgcagtgg ctttccgctc aagtgacgga tcatgttgaa   42480
gccgtggcgg gacgcagcct gtggcaggac gcctggatgc gctttcgcaa aaaccgcgcc   42540
gccatgacct cggtttacgt cttgctgttt attgtggtct gcattgtagt tgggccgcat   42600
gtcgcccctt tcagccacga tgaaatcgac tggagcgtcg tggcggatcc ctacgaactg   42660
ggcaagccct ccctggaaac cgggcattat ttcggcaccg acgacctggg ccaggacctg   42720
ttcgcccgca ccatgcaagg cggtcgcctg tctatcatgg tgggttttat gggcgccctg   42780
gtggcggtgc tgatcggcac ggtctggggc gctatttccg gctatgtggg cgggctggtg   42840
gacagcgtca tgatgcgggt catcgaagtg ctggactccg tgcccttcat gttcatggtg   42900
atcctgttcg tcaccctgtt cggcaacaat atctatctca tatttatcgt catcggcatg   42960
gtgtcctggc tcaacatcgc ccgcgtggtg cgcggcgtca cgtttagcat caagcggcgt   43020
gaattcatcg aagcgcgcca ttccatcggc gtgtccaagc tgaccattgt gcgtcgtcat   43080
gtattgccca acgtactggg cattgtgatg gtgtattcct cgctgatggt gcccggcttc   43140
atcatgtttg aatccttttct gagttttctg ggcctgggcg tgcagccgcc ggacaccagt   43200
tggggaattc ttatcgctga aggggcgaaa accattgatg tggcgctctg gctgctgatg   43260
tttccgtctc tgtttttggt cgccactctg ttctgtttca acttcatcgg cgacggcctg   43320
```

```
cgcgacgccc tcgacccgaa ggaccgctaa ctctcatgcg ccccggacct ctcatgcatc    43380
caataaaaaa gcaatcatcc agcaagcgcc aggagctctc atgactatat tgtccatcga    43440
aaacatgaat gttcgcttcg aaacgccgga cggactggtg caggcggtca gcgatctttc    43500
cttcaccgtg cgcgccggcg aaaccctcgg catcgtcggc gagtccggct ccggcaaaag    43560
ccagtcagtg ttcgccctga tggggctcac cgccgataac ggccgggtgt ccggcgtcgc    43620
caattttcat ggcgaaaacc tgctggccat gagcaagcgg caactgaacc gcattcgcgc    43680
agagaaaatc ggcatgatct ttcaggatcc gatgacctct ctgcatccat tcctgaagat    43740
cgacaagcag ctcaccgaag tgctgatgat tcataaaggc atgagcaagg cggcggcgcg    43800
ggcggaatcc atccgcatgc tggacgcggt gcgcattccc tcgccgcagg cgcgcatggg    43860
gcagtatcct cacgagctgt ccggcggcat gcgccagcgc atcatgatcg ccatggcgtt    43920
gctgtgtcgc ccggagttat tgatcgccga cgaacccacc accgccctgg acgtcacggt    43980
gcaggcgcag attctgtcgt tgttgtggga gctacaggga gaattcaata ccgccattct    44040
actgatcacc cacgacatgg gcgtggtcgc ggaaatgtgc gaccgggtgc tggtgatgta    44100
tggcgggcgc aagatggaag aggcggatac ggaaaccctg tttgagcgtc cggcccaccc    44160
ttacacccag ggcctgctga aggcgatccc gtcgattact gaagatatgc gcgcttgcc    44220 gaccatcccc ggcaatccgc ccaacgcgtt gatcaacaac aaaggctgcc cgttccggga    44280
gcgctgcagc ctgcagcagc cctcctgtga agccgccatt ccgccgctga cgcgacttgg    44340
cgccacgcaa ctggccgcct gccacggcct ggcgcagaac aaaaccacgc cgctggcgcg    44400
caccgcctga cgccatcgac acaggatcta caggatgaat gctaaagaag tcttactctc    44460
cgcccgcaac ctggaagtgc acttccctat cggcaagcac attctgccca gccggcgccc    44520
gcgcctgaaa gcggtcaacg gcattgacgt ggatgtgtat cgcggtgaaa ccctgggcat    44580
tgtgggtgaa tccggctgcg gcaaatcgac tctggcgcgc gccctgttgc ggctgatcga    44640
gcccacccgg ggcgaattgc gctggaaagg cgaagacctg cgcgggttcg acaaaaccac    44700
cctggtgcgt cgtcgccggg agttccagat ggtgtttcag daccccaccg ccagcctcaa    44760
tccccggttg acggtctcgg aatgcatcgc cgagcctctg ttgactcatg agccgggtct    44820
caagcgcaaa gacatcgagc gccgggtgat cgccatgatg dacaaggtcg gcctgtcggc    44880
gagtcagcgt aaccgctatc cccacgaatt ttccggcggc cagtgtcagc gcgtcggcat    44940
tgcccgcgcc ctgattctca acccggatct ggtggtgtgc gacgaaccgg tcagcgccct    45000
ggacgtctcc atccaggcgc aggtgatcaa tctgcttgac gacctcaaac aggagatggg    45060
gctgacgctg gtgatgatcg cccacgacct gagcgtggtg cgccacatca gcgatagagt    45120
catggtgatg tacctgggca gcccatgga agtcggcctg tatgaccggg ttttcgatca    45180
ggcgcagcat ccctacacca aagcgctgtt gtccgcggtc ccgatcgcca accccaaact    45240
ggcgcggcaa cgggaggtgc agcttttgcc cggccgatctg ccctcgccgc tcaacccgcc    45300
cagcggctgc gtctttcgca cccgatgccc ggaggccacc gatctctgtg ggagccagcc    45360
tcccactcag agcggctccg acgagcatcg tatttttgc tccaacacct tgttattggc    45420
gggtcaatga gattgcccgt caacacacca gcgccgggat gcgcttatcg tgggagacag    45480
gaccaggcat ccgcaaggtc tgtcgttttc agtttgtctg tcgaattaat cgtctgtcat    45540
taggaagttt ttagccatga acacgccctc agtcacgcaa cgactcgaac accttcgcaa    45600
ggcgatggac aagcaggcgt tcgccgccta catcgtcacc aacaacgacc cgcattccag    45660
tgagtattcc gctgatcatt ggctggcgcg aacctggatt tccggtttca acggttcggc    45720
```

-continued

```
gggcaatgtg gtcgtcaccg gcgatggcgg cggcctgtgg acggacggtc gttactttat  45780
tcaggcggag gagcaactgg cggggtccgg cctcaaactg ttcaaggcca ggctgccgga  45840
gacgccgacc attcctcaat ggctggccgc caccctgcca gaaaacgccc gcgtcggtgt  45900
ggacggccgc tcgatcagtc gcgcatttta tcaggagctg ttggacgcct cgcgcccaa  45960 gtcgattcag ctgattctgg accaggatct gatcacgccg ctctggtatg accgtcctgc  46020
tcgtcccaaa gcgccggtgt tcaaccatga attacgttac gctggcgtgg acgcgcagga  46080
aaaaatgcag cgcatccgcg actggatgac ggagcagcag gtggacggtc tgctggtctc  46140
cacgctggat gatgtgatgt gggcgctgaa tattcgcggc ggcgatacgc cctattgccc  46200
gatttccgag tcctatctgc tggtcaccgc gcagcaaagt caggtcttca tggatcgcga  46260
caagttgccg gaagcggtgg agtgcactct ggcggaatat ggcgtgacgg cccatggcta  46320
tgagcttgtc gtcgaggccg tgaatcagct accggaaggc tgcaggctgg ctatcaatcc  46380
cgccagcgcc aacagcctgt tggtcaacca gatcaagcca gagatcacgc tggtggaaac  46440
gccctgcccg gtcaccgaca tgaaggcgca gaagaacccc acggaaatgg agaacttcga  46500
gcaggcgctg cgtctggacg gcgtagccat ggtgaatttc atgtactggc tgcaaaccca  46560
ggttcccggc ggcaaggtga cggagttgtc cgcagaggcg cagctgcgcg cttatcgccg  46620
cgccacgtcc agctatatca gcgacagttt ccgcaccatc gccgggtttg ccctcacgc  46680 cgcgaagatg cattattccg ccagcactga cagcaacgcc actgtggatg aaagcaactt  46740
cttcctggtg gattccggcg gccagtaccc aggcggcacc accgacatca cccgcacctt  46800
tcattttggg acgcccaccg cgcagcagcg caaggactac accctggtgc tcaaggcggt  46860
gatacggctg acgcagaccg tgtttctgaa aggggccacc ggcgccaatc tggatatcat  46920
ggcgcggggc atgttatggc gtcatcgcat cgattacaaa tgcggcaccg gccatggcgt  46980
cggtctgtgt ctgaacgtgc atgaaggccc gcagaatttc tcgcagaacc ctaaagaagt  47040
cgctctcaag cccggcatgg tcatcaccaa tgaacccggc gtctaccgcg aaggcgagta  47100
cggcgtgcgc atcgagaaca tcatgaaagt ggtggagctg aagaaaacg agtttggcgt  47160 cttctatggc ttcgaaacca tcaccctggc gcccatcgcc atcaacgctc tggacctgtc  47220
catgctcagc actgaagaaa ctgattggct caacgcttat cactggcgcg tttacgaagc  47280
gctcagccct tatctggaag cctcacagac cgcgtggttg agaaacgcca ccaaaccggt  47340
ttaacggcct cactccacag ataccaagac ccggcggaca gtcgcttttt ccggctattt  47400
gtccgccatc ggctgggcct gtttcatgtt cgggcccagt cacccgcggc ttgacgccgc  47460
ccagacgcat tcatgcgtcc ggttaccagc atggcgcctt ctcgtcatgt tggtaaacaa  47520
gtagtacagg tagtacaggt agtagaagta caagaaggtc catccatgta ttgcccggcg  47580
ttcgccgggc ttttttttgcg catttgcccc cattcctgac cgtccctcac cgtctctgtt  47640
caccccgaaa gcgcaaactg tcagcgaaca atatcgggcg cttactgccc gcgcacaaat  47700
tcggtccgcc agttttggat atgggtgaga taacgctcac aggcgatatc cagttccgca  47760
tccatcaggt agtcggcctg atacaccaca aacggatcgc cccagggcag acggcagcga  47820
ttggcggtcg cctgcagcgg cgtcagcagg gtttccatgg tgaaacgatt ccgcccgcga  47880
ggctgataag ccgcctctgt attgccggcg gtggcggcga ccatgatagg cgcgccttcg  47940
aagcggcgcc cagtgttttc gtaatccagg taatacatgt gggtcagcac gagatcctgc  48000
cagcgctgca acaagggcgg cgtggagtac cactgaatag gaaattgcag aatcaggcgc  48060
```

```
tcgctttgca gcagtcgttc aatctccgtg gcgacgtcaa tgcgctcatc cggatacagc   48120
cgattcatat ccaccacatc cagattgtcg agggtttgcg ccgccgccat cagtgcagcg   48180
ttgatgcgtg aaggacgata acgggagtgg aacataagca gtgtggtttt catgtcgggc   48240
ggtccttttc agttcggttt tcagtgcgtt gtagcgcgtt gtttcaatag gacctagctt   48300
gcgttaccgg cttatattaa tctaatcgat agtttatata tttgattatt cgttttatga   48360
atttacgcgg cgtcgattta aatctgttag tgattctgga tgcgttaatg gacgagcgtc   48420
atgtcacgcg cgccgcgaag cgcctgcact tgtcgcaacc ggccacctcc agcgccctgg   48480
aacgctgtcg ccacctgttt ggcgaccctc ttttgattcg cggtcgcggt gaaatgcgcc   48540
tcagcgctaa agcggagtcc ctgcgtgaac ctgtcaaggc gttgttggcc caggcggagc   48600
gtgtgattaa tcaggcggat acgccctgg cggagctgcg ccagaccta cgcatcctga   48660 tggcggactt tcctgtttcc gcgctgttgg ggccgctaca tcaacgcctg atgaccagcg   48720
cccccaacct ggatttgatc atacagacct ggcatggcgc caagtccgcg ctggaacagc   48780
tcgccaaagg agaagccgat ctggccgtat ccgtgttccc caatgtcggc gcctcattcc   48840
gctgcgttga actgttgtat gaagactatt gcgtgctgat gcgcaaagac catcccgccg   48900
cccaggactt caacctgcaa caatggctcg cctatcccca tgtcctggtc tccggccgcg   48960
gcgacaccga cagccccgtc gaccaaaccc tgcaagccca cggactacgc cgccgcgtcg   49020
gtctcgtcgt cccctacttc caaatggccc ccgacctcgt cgcccaatcc gactacatcg   49080
ccctcctccc catccactgc gtcccccaag acaccacaaa attcaccgtc ttcccacccc   49140
ccataccagt agaaggcttc ccactacacc tggcgtggca cgtgagacgc caggggatc   49200 aggcggtgag ccatgtggtt gaggtgattc gggaggttac tgggttttaa atgaataacg   49260
tccaggaact aataattaag cggcaaaatg ccagaaaaac atctaataat tcaagctagt   49320
tacggaccaa gaatgctcga gccatgttga aattccaact taaggttttc taacatatga   49380
aactgctctg acacttactg ataggcttat cttgtactac agtttaacaa aggtactggg   49440
tcagctcttg tagtgagata agcggagttc gagaaagaaa tattcaagtg cgcttctgac   49500
accagcatga aaaatgcttt attttttcata tggaggatat catgaaaaag gaattgaggc   49560
accgagaagt agcattgtat aagtataata aaatacggta ttcatttgtc ccactaagcg   49620
taggtgaact gccaattctt actagtgatc cttggtcttt tttaagttca aaattacaaa   49680
tactcctccc caaaaagcgc ggcaacaata gattaaaaat agaacgagca atctattatt   49740
caggtttggc cgaggacttt tatagagcag cgaatagcgt gcctttacct gcaaaaagcg   49800
cactattata ttatggaatg ttggatttag ttaaatgcta tctaagcctg catgacgtgc   49860
cattggagtc gagccacgaa catcacggcc ttatcttacc tattaaaaat gaacaagttg   49920
tggaagttaa aggaaaaatg aaaggtgttg taaacatttt tcttgaattt tcatgtcttc   49980 tgggaaaaa catagataga gttcacagaa tcaaattcaa tcaagcactc tctcacgtac   50040
cagaaataca tagtatatac acaagccttg ggcatataaa taaacgaaag ctattaccag   50100
ttgacataga atttttgata acacaaaaaa aggacaaatt atacactgag ataagctata   50160
aaaaggaaca ggaggaaaaa gtaaatattg aaaaattcct tactggagaa agaagaaaat   50220
atttcaaaaa aatcaaggct gacaatgaaa aaataatcta tcactccagg cagaaaaaaa   50280
tcacacgaga aaacattcat atcatttaca aaaatacact aaatgaatat aaaaaactgg   50340
aaattgtccc catcttaaca agacaaggct atcgatatta tgtggattta attcctggtt   50400
acttaccaca ccttcgtac acattgcttg caatgttcta cctaggaggt gcagcaagat   50460
```

-continued

```
atcgtccatt agaaattaag tctctactca tgggggaact tagacctcta gtaagtgagt    50520
ttgttagtct atctcccaaa caattttat atcaaatggt ttcattaata acaagtaagg     50580
agtgcctaat tccatttgct tcaatttgag agccagtata atccaacctc tataaaagt    50640 ctcaatggca acaacacttg atccaatacg ccctagaaa ggccatgaaa attcattttt    50700
aaattaacgc tttcgttaaa cagagctata actttcagat gcaatgcata gagtggctta    50760 ggaaaacat tccccctccc cttgatattt aattgatatc tccttgattt ttgcttggtc     50820
cctgcttttc tacaattcct tagaaggctt ataaaaaaag gcggtttggc tatacgaggg    50880
gattggaggc ggtcggatgt gggtgttgtt tcgttatctt aatcgtcaga ttctgacgtc    50940 gcttttgga ttgacgtttc tgctgctgtt tgtgttcacc agtacgcgtt tcgctcagta    51000
tctgactgag gcggcgacgg ggcagatttc tgcggatgtg ctggcgccaa tcatggctta    51060
tcgtcttccc ggttttctgc agttgatatt gccgttggcg cttttcctgt cgattttgct    51120
tagctacggg cgcatgtatc tggatgcgga gatgaccgcc atattcgcca gcggggtgag    51180
caagtccaga cttgtcgccg tgaccatggg gtcggggttt gcaatcgcct tggtagtggg    51240
gtcgatgagt ctttatctga acccgttcgg ccggcagcag acggaacgga ttttactgga    51300
gcaagccaag cgctcccgct ttgaactcgt tactcccgga cgttttcaac gtttctccga    51360
gggagaggat ggccgggtgt cttatgtgga gtcgctcagc aacgatgacc gcgagatgcg    51420
caacgtttt                                                           51429
```

<210> SEQ ID NO 2
<211> LENGTH: 254
<212> TYPE: PRT
<213> ORGANISM: Hahella chejuensis

<400> SEQUENCE: 2

```
Met Thr Leu Arg Lys Leu Leu Ala Gly Ile Phe Leu Arg Ser Leu Val
  1               5                  10                  15

Val Leu Leu Val Gly Ile Trp Pro Pro Lys Gly Gly Ala His Ala Glu
                 20                  25                  30

Glu Phe Arg Val Leu Ala His Asn Thr Glu Phe Pro Pro Tyr Tyr Phe
             35                  40                  45

Tyr Gln Asp Gly Val Pro Thr Gly Phe Tyr Lys Asp Phe Phe Asp Ala
         50                  55                  60

Ile Ser Arg Ile Thr Gly Asp Thr Phe Ile Asn Gln Ala His Pro Leu
 65                  70                  75                  80

Ala Arg Gly Leu Met Met Phe Asn Glu Asn Leu Val Asp Ile Glu Ser
                 85                  90                  95

Gly Val Asn Pro Ala Trp Arg Ala Gly Glu Lys Thr Leu Gly Leu Phe
            100                 105                 110

Thr Ile Pro Tyr Ala Gln Ser Val Asp Ile Leu Leu Phe Gly Arg Asn
        115                 120                 125

Lys Ser Leu Pro Val Glu Ala Pro Ser Asp Leu Ile Gly Lys Arg Ile
    130                 135                 140

Gly Val Val Arg Gly Tyr Gln Tyr Pro Ser Phe Thr Lys Leu Phe Gln
145                 150                 155                 160

Asn Gly Asp Ile Glu Arg Tyr Asp Val Asn Gly Glu Ser Gln Leu Leu
                165                 170                 175

Thr Met Leu Val Ala Gly Arg Leu Asp Gln Val Ile Ile Asn Lys Asp
            180                 185                 190
```

```
Leu Ala Leu Tyr Arg Met Arg Glu Asn Pro Val Tyr Arg Gly Leu Glu
            195                 200                 205

Pro Gly Phe Glu Val Gly Gly Val Asp Val Met Leu Arg Ile His Pro
        210                 215                 220

Asn Lys Ala Ala Ala Leu Glu Arg Leu Asn Ala Ala Ile Lys Ala Leu
225                 230                 235                 240

Ile Asp Ser Gly Glu Ile Glu Gly Ile Trp Asp Lys Tyr Arg
                245                 250
```

<210> SEQ ID NO 3
<211> LENGTH: 251
<212> TYPE: PRT
<213> ORGANISM: Hahella chejuensis

<400> SEQUENCE: 3

```
Met Ile Tyr Leu Lys Gln Arg Gly Ile Ser Met Lys Ala Leu Ser Thr
  1               5                  10                  15

Leu Ile Leu Thr Met Phe Val Ala Phe Ser Ala Gln Ala Glu Thr Val
            20                  25                  30

Thr Ala Ala Gln Asp Pro Trp Pro Pro Phe Ile Gln Glu Gly Ser Asp
        35                  40                  45

Pro Gly Ile Ser Ile Ala Leu Leu Lys Ala Ala Met Glu Lys Glu Gly
    50                  55                  60

Tyr Thr Val Asp Phe Lys Ile Leu Pro Trp Lys Arg Ala Leu Asn Asp
65                  70                  75                  80

Val Ile Asn Gly Asn Ile Asp Ile Leu Pro Gly Ala Trp Phe Thr Glu
                85                  90                  95

Glu Arg Ala Lys Val Leu Asn Tyr Ser Asn Tyr Tyr Ala Gln Asn Ser
            100                 105                 110

Ile Lys Phe Ile Lys Arg Lys Gly Asp Pro Phe Glu Phe Asn Gly Leu
        115                 120                 125

Asp Ser Leu Thr Gly Lys Lys Val Gly Ile Val Ser Gly Tyr Gly Tyr
    130                 135                 140

Gly Asp Glu Phe Thr His Ala Thr Asn Phe Ser Arg Pro Glu Ala Gly
145                 150                 155                 160

Thr Ile Glu Ala Asn Val Lys Lys Leu Leu Ser Asp Arg Val Asp Leu
                165                 170                 175

Thr Leu Glu Asp Glu Ile Val Ala Lys Ser Val Met Lys Glu Ala Gly
            180                 185                 190

Ile Asp Leu Gly Ser Val Glu Phe Thr Asn Asn Ala Leu Ser Val Asn
        195                 200                 205

Asp Leu His Val Ala Thr Gly Lys Ala Asn Ala Gln Gly Gln Lys Leu
    210                 215                 220

Ile Glu Ala Tyr Asn Arg Gly Leu Ala Ala Ile Lys Ala Asp Gly Thr
225                 230                 235                 240

Tyr Asp Lys Ile Leu Ala Asp Tyr Gly Val Lys
                245                 250
```

<210> SEQ ID NO 4
<211> LENGTH: 1289
<212> TYPE: PRT
<213> ORGANISM: Hahella chejuensis

<400> SEQUENCE: 4

```
Met Asn Leu Gly Glu Thr Asn Ile His Thr Asp Gly Pro Ala Arg Gly
  1               5                  10                  15
```

```
Ser Val Leu Lys Arg Lys Gly Ala Leu Ser Val Leu Thr Val Ala
             20                  25                  30

Ala Leu Thr Phe Cys Gln Ser Ala Met Ala Val Thr Ala Val Ser Glu
         35                  40                  45

Gly Val Met Thr Pro Ile Gly Glu Ser Gly Phe Glu Thr Pro Asp Val
     50                  55                  60

Pro Ser Gly Gly Tyr Gln Tyr Leu Pro Arg Gly Gly Glu Trp Ala Phe
 65                  70                  75                  80

Ala Asp Gly Ala Gly Ile Thr Glu Asn Gly Ser Ala Phe Thr Ser Cys
                 85                  90                  95

Asn Pro Ala Thr Pro Gln Gly Gln Gln Ala Leu Phe Ile Gln Gln Thr
             100                 105                 110

Gly Gln Val Gln Lys Thr Ile Thr Ile Pro Asn Ala Gly Val Tyr Arg
         115                 120                 125

Val Asn Leu Arg Gly Ala Gln Arg Gly Cys Ile Asn Ser Pro Gln Gly
     130                 135                 140

Gln Thr Leu Arg Val Ser Leu Ala Gly Ser Gln Ile Gly Arg Ile Arg
145                 150                 155                 160

Pro Gln Asp Ser Asn Tyr Arg Leu Tyr His Ser Thr Ala Met Trp Leu
             165                 170                 175

Glu Pro Gly Lys Tyr Gln Leu Leu Leu Ser Gly Leu Asn Ala Ser Gly
         180                 185                 190

Asp Asn Thr Ala Phe Val Asp Val Gln Leu Glu Lys Leu Pro Val
             195                 200                 205

Trp Ser Glu Ala Ser Ser Trp Leu Glu Asn Ser Val Pro Gly Pro Gly
210                 215                 220

Glu Glu Val Tyr Ile Pro Ala Gly Ala Thr Met Val Leu Asp Asn Leu
225                 230                 235                 240

Asn Ala Ala Asn Val Ile Ile Asn Glu Gly Ile Leu Thr Ala Pro Val
             245                 250                 255

Asn Arg Asp Phe Thr Leu Asp Val Ala Glu Ile His Val Met Ala Gly
             260                 265                 270

Gly Val Leu Glu Leu Gly Arg Glu Glu Ala Pro Phe Asn Gly Gln Gly
         275                 280                 285

Val Ile Thr Leu Leu Gly Asp Asn Pro Ala Ala Glu Ser Lys Leu Ile
     290                 295                 300

His Ala Met Asn Gly Gly Arg Ile Glu Met His Gly Gln Pro Gln Arg
305                 310                 315                 320

Ser Trp Thr Gln Leu Gly Ala Ser Ala Ala Ile Gly Asp Asn Ser Ile
             325                 330                 335

Thr Leu Lys Glu Ser Val Asn Trp Arg Ala Gly Asp Arg Ile Val Ile
             340                 345                 350

Ala Ser Ser Asp Phe Asp Met Asn His Ala Glu Glu Phe Thr Ile Val
         355                 360                 365

Ser Ile Ser Gly Asp Arg Lys Thr Leu Thr Leu Asn Ala Arg Leu Ala
     370                 375                 380

Tyr Asn His Phe Gly Lys Leu Gln Gln Tyr Ser Asp Asn Gly Gln Ser
385                 390                 395                 400

Trp Thr Leu Asp Glu Arg Ala Glu Val Gly Leu Leu Ser Arg Asn Leu
             405                 410                 415

Arg Ile Gln Gly Asp Ala Asp Ser Asp Arg Thr Ala Tyr Gly Gly Asn
             420                 425                 430

Ile Met Val Met Arg Gly Ala Phe Gly Arg Leu Ser Asn Val Glu Leu
```

```
                435                 440                 445
Thr Arg Met Gly Gln Arg Arg Lys Leu Gly Arg Tyr Pro Phe His Trp
450                 455                 460

His Leu Ala Gly Asn Ala Ala Gly Gln Tyr Ile Arg Ser Ser Ser Ile
465                 470                 475                 480

His His Thr Tyr Asn Arg Ala Ile Thr Ile His Gly Thr Asn Asn Ala
                485                 490                 495

Ser Val Glu Asn Asn Val Cys Tyr Asp Asn Leu Gly His Ala Val Phe
            500                 505                 510

Met Glu Asp Gly Asn Glu Thr Gly Asn Arg Ile Val Gly Asn Leu Gly
        515                 520                 525

Met Val Thr Arg Lys Pro Ala Pro Glu Tyr Ala Leu Leu Pro Ser Asp
530                 535                 540

Phe Thr Asn Gly Arg Leu Arg Asn Ala Ser Gly Pro Ser Thr Phe Trp
545                 550                 555                 560

Ile Thr Asn Pro Asn Asn Ile Val Gln Asn Asn His Ala Ala Gly Ser
                565                 570                 575

Asp Gly Ser Gly Phe Trp Phe Ala Phe His Gln Asn Pro Asn Ser Pro
            580                 585                 590

Val Phe Gln Gln Gly Leu Asn Pro Asn Val Gln Asn Leu Pro Ala Gly
        595                 600                 605

Ala Ile Asp Asn Asn Thr Ala His Ser Ser Phe His Gly Trp Leu Leu
610                 615                 620

Gly Met Ala Pro Thr Pro Asn Asp Ala Ser Gln Thr Pro Asn Leu Asn
625                 630                 635                 640

Asn Asp Tyr Met Pro Gln Gln Glu Pro Val Ile Asn Gly Leu Thr Val
                645                 650                 655

Tyr Lys Asn Tyr Leu Gly Met Tyr Ser Arg Val Gly Gly Asn Arg Gly
            660                 665                 670

Lys Ser Thr Tyr Asn Asp Leu Ile Val Ala Asp Asn Tyr Glu Gly Glu
        675                 680                 685

Ala Ser Thr Trp Val Thr Asp Tyr Asn Arg Val Leu Trp Val Gly Ala
        690                 695                 700

Ser Glu Asn Tyr Glu Pro Val Ala Pro Leu Gly Leu Ser Ala Ser Ser
705                 710                 715                 720

Gly Val Ile Gly Met Ala Ile Gly His Ile Leu Tyr Asp Gly Pro Val
                725                 730                 735

Arg Ile Arg Asp Ser His Phe Thr Gly Phe Glu Arg Asp Asn Phe Thr
            740                 745                 750

Leu Phe Asp Gln Trp Gly Ala Asn Ile Lys Tyr Ser Gly His Ser Leu
        755                 760                 765

His Asn Thr Thr Val Ser Pro Gly Ser Tyr Gln Val Arg Tyr Arg Asn
        770                 775                 780

Asp Tyr Ile Gly Pro Val Trp Phe Asn Gly Ala Ile Tyr Asp Val Asp
785                 790                 795                 800

Gly Thr Leu Thr Gly Gln Pro Met Thr Ala Ile Thr Gln Asp His Pro
                805                 810                 815

Met Leu Val Asp Gly Asn Ser Ser Arg Ile Arg Asp Gly Leu Ser Gly
            820                 825                 830

Met Glu Ser Arg Arg Arg Phe Ala Tyr Val Glu Val Arg Pro Ser Asp
        835                 840                 845

Glu Ile Trp Leu Pro Pro Ala Pro Leu Val Ser Arg Arg Gln Asp
850                 855                 860
```

```
Ser Thr Phe Phe Arg Ser Asp Gly Ala Arg Tyr Thr Glu Ser Arg Lys
865                 870                 875                 880

Glu Ile Glu Gly Val Ser Leu Leu Pro Met Val Asp Gly Ala Tyr Asn
            885                 890                 895

Tyr Ala Tyr Ile Tyr His Asp Gln Ile Pro Ser Ile Thr Arg Phe Asp
        900                 905                 910

Tyr His Ser Met Ser Ser Gly Glu Tyr Val Thr Leu Glu Leu Pro Gly
    915                 920                 925

Val Ala Pro Asn Val Tyr Val Tyr Leu Gly Thr Pro Ala Gly Gln Tyr
930                 935                 940

Gly Phe Ser Gly Pro Leu Ile Gln Leu Gly Ser Val Gly Ala Trp Ala
945                 950                 955                 960

Ala Leu Arg Ala Phe Asp Gly Asn Ala Trp Ala Tyr Glu Asn Gly Ser
            965                 970                 975

Leu Phe Val Arg Phe Lys Ala Pro Ala Gly Ala Asp Phe Arg Asn Pro
        980                 985                 990

Gly Glu Leu Gly Ser Ile Phe Val Cys Leu Asn Ser Gly Cys Ala Gln
    995                 1000                1005

Gly Ala Asn Arg Pro Leu Ala Pro Asn Val Tyr Val Leu Asn Lys Gln
   1010                1015                1020

Gly Gly Ala Arg Thr Ser Phe Gln Lys Leu Leu Arg Ser Lys Ser Phe
1025                1030                1035                1040

Ile Ser Thr Ala Ala Gln Asn Ser Ala Leu Glu Ala Thr Asn Glu Ala
                1045                1050                1055

Trp Gln Phe Asp Met Thr Asp Trp Asp Arg Asp Gly Tyr Met Asp Ile
            1060                1065                1070

Ala Gly Phe Lys Lys Arg Asn Thr Gly Thr Gly Thr Thr Glu Val His
        1075                1080                1085

Ile Met Asp Gly Lys Ser Gly Leu Gln Arg Phe Ile Phe Gln Ser Gly
    1090                1095                1100

Thr Ala Leu Gly Tyr Met Asn Val Asn Asp His Met Ala Ile Arg Asp
1105                1110                1115                1120

Tyr Asn Gly Asp Gly Gln Pro Asp Ile Trp Ala Ile Met His Asn Thr
                1125                1130                1135

Thr Gly Ser Gly Arg Thr Glu Val His Val Leu Asp Gly Arg Asn Pro
            1140                1145                1150

Gln Asn Phe Leu Leu His Asp Ala Thr Gly Leu Gly Leu Arg Pro Asn
        1155                1160                1165

Ser Ser Asp Glu Phe Leu Val Ser Asp Tyr Asp Arg Asp Gly Arg Pro
    1170                1175                1180

Asp Leu Trp Tyr Ile Ala Lys Arg Gly Gly Ser Asn Arg Thr Glu Val
1185                1190                1195                1200

His Ile Leu Ser Ala Gln Ser Gly Tyr Asp Asn Phe Ile Val His Ser
                1205                1210                1215

Ala Thr Ala Leu His Val Thr Asp Asp Asn Trp Ser Phe Arg Val Ala
            1220                1225                1230

Asp Phe Asn Gly Asp Gly Ala Pro Asp Leu Ile Gly Phe Lys Arg Asn
        1235                1240                1245

Gly Val Asn Ser Thr Glu Ile His Val Leu Asn Gly Ala Asn Asn Phe
    1250                1255                1260

Gln Asn Phe Leu Phe Gln Ser Ala Thr Glu Leu Pro Lys Gly Ser Ala
1265                1270                1275                1280
```

```
Asn Asn Val Tyr Leu Ile Ser Asp Arg
            1285

<210> SEQ ID NO 5
<211> LENGTH: 431
<212> TYPE: PRT
<213> ORGANISM: Hahella chejuensis

<400> SEQUENCE: 5

Met Glu Lys Ile Lys Gly Val Leu Val Gly Arg Ser Ser Thr Arg Gly
  1               5                  10                  15

Phe Met Thr Asn Ile Arg Met Leu Ser Leu Ile Gly Ile Tyr Leu Val
                 20                  25                  30

Ile Phe Ile Asp Asn Leu Gly Ala Ser Leu Ile Ile Pro Met Leu Thr
             35                  40                  45

Pro Ile Ala His Asp Pro Ala Ala Gly Leu Ile Ser Glu Gly Ser Glu
         50                  55                  60

Ser Phe Arg Asn Gly Val Tyr Gly Val Ala Leu Gly Ala Phe Ser Ile
 65                  70                  75                  80

Ala Met Phe Phe Gly Ala Pro Leu Leu Gly Ala Leu Ser Asp Gly Leu
                 85                  90                  95

Gly Arg Lys Lys Thr Leu Leu Leu Cys Leu Gly Gly Leu Ala Met Ser
                100                 105                 110

Tyr Val Phe Leu Ala Leu Ala Leu Ala Phe Lys Ser Leu Trp Leu Phe
            115                 120                 125

Met Ala Gly Arg Leu Ile Gly Gly Phe Phe Ser Gly Ser Leu Pro Val
        130                 135                 140

Ala Gln Ala Ser Ile Ile Asp Val Thr Glu Glu Lys Leu Arg Ala Lys
145                 150                 155                 160

Tyr Ile Gly Tyr Ile Met Phe Phe Val Ser Leu Gly Tyr Val Val Gly
                165                 170                 175

Pro Leu Ile Gly Gly Tyr Leu Ser Asp Pro Ala Leu Val Pro Trp Phe
            180                 185                 190

Asn Leu Gln Thr Pro Phe Val Phe Val Ala Ala Leu Ser Val Val Asn
        195                 200                 205

Leu Leu Ile Leu Leu Val Phe Gln Asp Gln Gln Ala Asp Ala Asp
    210                 215                 220

Gly Arg Gly Met Thr Leu Pro Asn Pro Ile Ala Asn Leu Leu Asp Ala
225                 230                 235                 240

Val Arg Ile Lys Asp Ile Arg Thr Tyr Ala Leu Leu Leu Leu Leu Met
                245                 250                 255

Leu Val Gly Trp Asn Thr Phe Phe Gln Phe Ile Gly Leu Tyr Leu Thr
            260                 265                 270

Gly Glu Leu Gly Leu Gly Gln Gln Glu Val Ser Ser Phe Val Ser Trp
        275                 280                 285

Val Gly Phe Gly Leu Ala Ser Ala Phe Leu Phe Leu Val Gly Val Ala
    290                 295                 300

Met Lys Met Leu Lys Pro Leu Gly Met Val Gly Val Ala Leu Ala Leu
305                 310                 315                 320

Met Ala Leu Cys Ile Gly Gly Thr Leu Ile Ser Thr Asn Val Tyr Ala
                325                 330                 335

Leu Tyr Leu Leu Ala Ala Leu Gly Ala Val Gly Phe Gly Leu Ser Tyr
            340                 345                 350

Ser Gly Leu Met Ala Gln Leu Ser Met Ser Val Asp Ala Ser Arg Gln
        355                 360                 365
```

```
Gly Ser Ile Met Gly Met Ala Ala Ile Ala Ala Phe Ser Ala Gly
        370                 375                 380

Phe Ser Gly Phe Ala Phe Gly Phe Val Ala Asn Ile Ser Val Ser Ala
385                 390                 395                 400

Pro Ile Leu Ser Ala Leu Leu Cys Val Cys Leu Ala Ile Leu Val Cys
                405                 410                 415

Cys Lys Glu Gln Met Ser Leu Ala Arg Gln Val Lys Tyr Ala Asp
            420                 425                 430

<210> SEQ ID NO 6
<211> LENGTH: 1066
<212> TYPE: PRT
<213> ORGANISM: Hahella chejuensis

<400> SEQUENCE: 6

Met Glu Val Lys Glu Arg Leu Val Ala Leu Phe Ala Glu Ala Leu Leu
1               5                   10                  15

Ala Asp Pro Gly Asp Ile Glu Thr Gly Ala Glu Val Ala Thr Leu Gly
            20                  25                  30

Val Asp Ser Ile Leu Ala Ala Gln Leu Ser Lys Leu Ile Asn Arg His
        35                  40                  45

Phe Asp Cys Gly Ile Thr Pro Thr Asp Ile Tyr Glu Cys Ile Ser Ile
    50                  55                  60

Asp Gly Leu Thr Val His Ile Ser Lys Val Leu Ala Asp Thr Pro Gln
65                  70                  75                  80

Thr Gly Ala Ala Glu Gln Ser Ser Glu Pro Thr Gln Ala Ser Arg Gly
                85                  90                  95

Glu Asp Pro Gln Asp Asp Leu Ile Gln Asp Ala Ile Val Val Val
            100                 105                 110

Gly Met Ala Ala Gln Phe Ala Gly Cys Asp Gly Val Asp Ala Tyr Trp
        115                 120                 125

Asp Ala Ile Met Gln Gly Thr Ser Gln Leu Thr Thr Thr Asp Arg Trp
    130                 135                 140

Arg Arg Gln Gly Thr Arg Glu Phe Val Gly Gly Phe Leu Pro Asp Tyr
145                 150                 155                 160

Asp His Phe Asp Ala Gly Phe Phe Lys Ile Ser Pro Asn Glu Ala Lys
                165                 170                 175

Cys Met Asp Pro Gln Gln Arg Leu Leu Met Gln Ser Ala Gln His Ala
            180                 185                 190

Ile Asp Asp Ser Tyr Leu Gly Leu Asp Glu Leu Arg Glu Leu Gln Cys
        195                 200                 205

Gly Val Phe Ala Val Ser Leu Pro Gly Asp Tyr Lys Phe Val Val Ala
    210                 215                 220

Arg His Pro Glu Gln Ala Phe Ser Thr His Ser Phe Leu Gly Asn Ala
225                 230                 235                 240

Thr Ser Thr Leu Ser Gly Arg Ile Ser Tyr Phe Tyr Asp Phe Asn Gly
                245                 250                 255

Pro Ser Leu Thr Leu Asp Thr Ala Cys Ser Ser Ser Leu Ser Ala Leu
            260                 265                 270

His Glu Ala Cys Leu Asn Ile Gln Ala Gly His Cys Gly Ala Ala Ile
        275                 280                 285

Val Ala Ala Ala Ser Val Phe Ser Thr Pro Glu Leu Phe Glu Phe Ala
    290                 295                 300

Gln Arg Ser Asn Met Ser Ser Pro Ser Gly Arg Cys Ala Ala Phe Ser
```

```
              305                 310                 315                 320
Asp Asp Ala Asp Gly Phe Thr Pro Ala Glu Gly Cys Ala Ser Val Ile
                325                 330                 335

Leu Met Arg Tyr Gly Glu Ala Lys Ala Arg Gly Leu Arg Val Tyr Gly
                340                 345                 350

Ala Ile Val Ala Thr Gly Leu Asn His Asp Gly Arg Ser Asn Gly Leu
                355                 360                 365

Met Ala Pro Asn Ala Gln Ser Gln Ser Arg Leu Ile Arg Asn Leu Tyr
                370                 375                 380

Arg Arg His Glu Val Asp Val Ala Arg Leu Ala Tyr Val Glu Thr His
385                 390                 395                 400

Gly Thr Gly Thr His Leu Gly Asp Pro Ile Glu Met Arg Gly Leu Thr
                    405                 410                 415

Glu Ala Phe Lys Asp His Gly Glu Asp Tyr Ala Cys Leu Leu Gly Ala
                420                 425                 430

Val Lys Pro Ile Ile Gly His Ser Leu Val Cys Ser Gly Leu Ala Gly
                435                 440                 445

Ile Ile Lys Val Leu Leu Ser Phe Lys His Glu Thr Ile Pro Pro Phe
                450                 455                 460

Pro Ala Leu Arg Lys Thr Asn Ala Leu Ile Asp Phe Ala Gly Phe Arg
465                 470                 475                 480

Met Asn Phe Glu Pro Leu Pro Trp Pro Gln Asp Lys Pro Leu Cys Ala
                    485                 490                 495

Val Ser Ala Phe Gly Phe Thr Gly Ser Asn Gly His Ala Leu Leu Arg
                500                 505                 510

Lys Met Pro Ser Thr Thr Arg Asn Leu Ala Ala Arg Thr Gly Glu
                515                 520                 525

Ala Leu Pro Phe Cys Leu Ser Ala Gln Ser Arg Asn Ser Leu Ile Ala
                530                 535                 540

Ser Val Gly Arg Val Arg Gln Leu Val Gly Lys Leu Asp Glu Asp Ala
545                 550                 555                 560

Leu Tyr Asp Leu Ser Gln Leu Leu Arg Arg Pro Arg Tyr Gly Leu
                    565                 570                 575

His Cys Ala Ile Ile Ala Ala Asn Lys Ser Asp Leu Leu Ser Ala Leu
                580                 585                 590

Glu Gln Leu Ala His Glu Leu Asp Ala Gly Asp Ala Leu Arg Asn Ala
                595                 600                 605

Pro Leu Ala Val Arg Glu Leu Thr Leu Ser Thr Asp Lys Leu Ala Leu
                610                 615                 620

Met Thr Leu Trp Arg Ala Gly Glu Gln Gly Glu Val Arg Arg Arg Leu
625                 630                 635                 640

Asp Ala Val Ala Ser Leu Asn Pro Asp Val Asn Ala Pro Ala Tyr Pro
                    645                 650                 655

Phe Asp Gly Lys Arg Tyr Trp Ile Asp Asp Arg Glu Asp Glu Gln Val
                660                 665                 670

Ala Asp Ala Ser Pro Ser Thr Gln Ala Asp Ser Thr Leu Ser Thr Glu
                675                 680                 685

Ala Ile Val Glu Glu Leu Arg Ala Ala Val Ser Asp Leu Leu Gly Phe
                690                 695                 700

Ala Pro Asp Glu Leu Pro Arg Asp Ala Leu Ile Glu Asp Leu Gly Leu
705                 710                 715                 720

Asp Ser Leu Ser Ala Leu Lys Leu Leu Ala Pro Tyr Gln Gln Arg Gly
                    725                 730                 735
```

```
Pro Gly Leu Gln Ala His Asp Leu Phe Arg Tyr Arg Thr Leu Ala Asp
                740                 745                 750

Leu Ala Ala Ala Ile Ala Ala Gly Val Glu Ser Ala Thr Val Ala
            755                 760                 765

Glu Glu Lys Gly Ile Val Glu Gln Lys Val Ile Ala Glu Arg Gly
770                 775                 780

Ile Ala Glu Glu Arg Gly Ile Ala Glu Arg Gly Ile Ala Glu Glu
785                 790                 795                 800

Arg Gly Ile Ala Glu Glu Lys Val Lys Ala Glu Ala Pro Arg Glu Ser
                805                 810                 815

Ala Ser Ala Thr Ala Ser Gly Pro Met Ala Gln Trp Leu Ser Tyr Gly
                820                 825                 830

Glu Gly Arg Pro Ile Ile Leu Ala Pro Pro Leu Asn Thr Ser Ala Glu
                835                 840                 845

Ala Trp Thr Gln Gln Ile Asn Ala Leu Thr Gln Ser Gly Arg Arg Val
                850                 855                 860

Leu Ile Pro Ile Tyr Pro Gly His Lys Asp Cys Pro Phe Asp Ala Ala
865                 870                 875                 880

Ala Phe Ser Leu Glu Ala Leu Ala Glu Asp Met Ala Ile Phe Ile Arg
                885                 890                 895

Gln Glu Leu Ser Ser Asn Ala Val Asp Leu Val Gly Trp Ser Leu Gly
                900                 905                 910

Gly Cys Leu Ser Cys Leu Ile Ala Ile His His Pro Asp Leu Val Arg
                915                 920                 925

Ser Leu Thr Leu Ile Ser Thr Ala Pro Ser Phe Gly Glu Asp Val Phe
                930                 935                 940

Gly Asn Thr Leu Asp Leu His Asp Glu Leu Lys Ala His Arg Asp Met
945                 950                 955                 960

Leu Glu Ile Val Phe Asp Gly Ala Glu Asp Ile Val Ala Ser Leu Gly
                965                 970                 975

Ala Gly Ala Pro Met Ser Val Leu Arg Tyr Tyr Tyr Asp Ala Leu Met
                980                 985                 990

Arg Phe Asp Val Asn Ala Arg Leu Gly Gly Ile Ala Met Pro Val Leu
                995                 1000                1005

Leu Thr His Gly Gln Asn Asp Cys Val Ile Asp Glu Ala Thr Phe Asp
        1010                1015                1020

Gln Leu Arg Arg Ile Pro Gln Ala Ala Glu Leu Val Val Lys Gly His
1025                1030                1035                1040

Gly His Phe Ile Pro Leu Thr Ala Ser Arg Phe Phe Asn Thr Gln Leu
                1045                1050                1055

Leu Arg Phe Leu Asn Gly Glu Gly Ile Gly
        1060                1065

<210> SEQ ID NO 7
<211> LENGTH: 2345
<212> TYPE: PRT
<213> ORGANISM: Hahella chejuensis

<400> SEQUENCE: 7

Met Glu Ile Leu Arg Arg Gln Leu Thr Glu Val Ala Ala Pro Pro His
  1               5                  10                  15

Gly Glu Ile Gln Ala Glu Arg Val Leu Val Ala Thr Asp Cys Ala Glu
                 20                  25                  30

Ala Ala Thr Ala Ala Arg His Met Gly Ala Ala Val Leu Arg Leu Asp
```

```
            35                  40                  45
Gln Val Pro Asp Glu Ala Gly Met Gln Ala Arg Leu Thr Glu Ile Gly
             50                  55                  60

Gly Gly Arg Asp Val Val Ala Val Ile Ala Gly Arg Asp Arg Pro Leu
 65                  70                  75                  80

Ala Ser Leu Thr Glu Gly Ser Trp Met Ser Cys Ser Arg Arg Ser Leu
                 85                  90                  95

Glu Leu Leu Arg Trp Leu Phe Ala Gln Lys Arg Gln Ile His Leu Leu
            100                 105                 110

Ser Leu His Ser Gln Gln Asp Ala Leu Ala Ala Leu Phe Asp Gly Leu
        115                 120                 125

Ala Arg Ser Ala Ser Leu Glu Thr Ser Arg Cys Gln Phe Thr Ser Ala
    130                 135                 140

Arg Ile Pro Ala Gly Pro Ile Gly Ala Ala Leu Pro Ala Tyr Ile Ala
145                 150                 155                 160

Ala Gly Leu Ala Trp Pro Gly Arg Arg Leu Arg Phe Asp Gly Thr Gly
                165                 170                 175

Leu Arg Val Glu Ser Trp Val Ala Ala Gly Gln Gly Ala Pro Thr Leu
            180                 185                 190

Thr Pro Phe Arg Asp Gly Glu Asn Ile Val Leu Ile Gly Gly Ala Gly
        195                 200                 205

Gly Val Gly Gln Glu Leu Ile Arg Val Leu Gln Ser Thr Arg Arg Leu
    210                 215                 220

Asn Leu Phe Val Leu Gly Arg Lys Ala Pro Asp Ala Gly Leu Thr Gln
225                 230                 235                 240

Thr Leu Lys Ala Tyr Gly Val Lys Ser Tyr Leu Arg Val Asp Ala Thr
                245                 250                 255

Asp Tyr Gly Val Leu Lys Ala Ala Phe Thr His Ile Glu Gln Gly Phe
            260                 265                 270

Gly Ala Ile Lys Ala Val Phe Asn Leu Ala Gly Thr Leu Asp Asp Cys
        275                 280                 285

Leu Phe His Asn Leu Thr Ala Glu Arg Leu His Arg Thr Leu Arg Ala
    290                 295                 300

Lys Val Gly Val Val Leu Asn Leu Ala Ala Leu Gln Gln Asp Tyr Gln
305                 310                 315                 320

Pro Gln Tyr Val Val Asn Phe Ser Ser Leu Thr Ala Thr Leu Gly Asn
                325                 330                 335

Val Gly Gln Ser Ala Tyr Gly Ala Ala Asn Glu Phe Val Glu Leu Ala
            340                 345                 350

Ser Glu Leu Leu Pro Asn Trp Cys Ser Phe Ala Trp Gly Leu Trp Arg
        355                 360                 365

Ser Gln Gly Met Gln Met Ala Gln Asp Asp Ser Gly Leu Arg Pro Met
    370                 375                 380

Glu Pro Gln Pro Ala Cys Glu Arg Met Leu Ser Ala Leu Ala Ala Gly
385                 390                 395                 400

Glu Arg His Leu Val Ile Tyr Glu Gly Ala Ala Gly Met Asn Ala
                405                 410                 415

Leu Arg Gly Asp Met Asp Ala Pro Gln Ser Ala Ser Glu Pro Glu Val
            420                 425                 430

Val Glu Gln Ser Pro Leu Ala Gln Gly Asp Ser Val Glu Leu Glu Ala
        435                 440                 445

Gln Thr Arg Arg Trp Leu Arg Asp Ile Val Arg Arg His Ser Gly Leu
    450                 455                 460
```

```
Lys Ala Val Lys Asp Asp Asn Leu Leu Asp Lys Gly Leu Asp Ser
465                 470                 475                 480

Val Ala Ser Ile Gln Ile Ser Thr Asp Ile Ala Ala Gln Leu Ser Pro
                485                 490                 495

Gln Gly Asp Phe Lys Leu Ser Arg Ala Ile Leu Phe Glu Cys Ser Thr
                500                 505                 510

Ile Arg Gln Leu Ala Glu His Leu Met Glu Arg Ala Gln Pro Leu Leu
                515                 520                 525

Cys Ala Cys Leu Ala Asp Thr Glu Gly Ala Ala Ser Arg Gln Val
530                 535                 540

Glu Thr Ala Pro Ala Glu Gln Ala Gln Ile Asp Ala Thr Asp Asn Thr
545                 550                 555                 560

Pro Asp Ala Lys Glu Ala Asn Ser Glu His Val Lys Pro His Gly Gly
                565                 570                 575

Gly Ala Thr Pro Thr Leu Thr Asn Glu Pro Lys Leu Ser Thr Asp Ala
                580                 585                 590

Tyr Arg Asp Asp Asp Ile Ala Ile Ile Gly Met Ala Gly Glu Phe Pro
                595                 600                 605

Asn Gly Ala Thr Pro Glu Ala Phe Trp Arg Ser Leu Ala Ala Gly Glu
                610                 615                 620

Asp Ala Val Arg Val Ile Pro Gln Ser Arg Trp Asp Trp Arg Arg Asp
625                 630                 635                 640

Tyr Ser Ala Ser Thr Ala Gln Gly Glu Ala Thr Tyr Gly Arg His Gly
                645                 650                 655

Gly Phe Met Glu Gly Val Ala Glu Phe Asp Pro Ala Phe Phe Asn Ile
                660                 665                 670

Ala Pro Val Asp Ala Ala Leu Leu Asp Pro Gln Glu Arg Arg Phe Leu
                675                 680                 685

Gln Val Ser Tyr His Ala Leu Glu Asp Ala Gly Tyr Phe Val Ser Pro
                690                 695                 700

Ser Lys Asp Val Gly Val Phe Ala Ala Ala Met Phe Gly His Tyr Gln
705                 710                 715                 720

Asp Leu Asp Ala Ser Arg Val Val Ser Ser Phe Ala Ala Ile Ala
                725                 730                 735

Asn Arg Val Ser Tyr Ala Phe Asp Leu Gln Gly Pro Ser Leu Thr Val
                740                 745                 750

Asp Thr Met Cys Ser Gly Ser Leu Thr Ala Leu His Met Ala Cys Asn
                755                 760                 765

Ser Leu Arg Leu Gly Glu Cys Arg Met Ala Leu Ser Gly Gly Val Asn
                770                 775                 780

Ile Met Ala His Pro Gly Lys Tyr Arg Leu Leu Ser Gln Gly Lys Phe
785                 790                 795                 800

Leu Ser Ala Ser Gly His Cys His Ala Phe Gly Val Glu Ala Asp Gly
                805                 810                 815

Tyr Val Pro Gly Glu Gly Ala Ala Val Val Leu Lys Ser Val Ala
                820                 825                 830

Asp Ala Leu Arg Asp Gln Asp Val Ile Tyr Ala Ile Val Arg Ala Thr
                835                 840                 845

Ala Ile Asn Ser Gly Gly Lys Thr Ser Ser Phe Thr Val Pro Ser Ala
                850                 855                 860

Arg Ala Gln Gln Arg Val Ile Gln Asp Ala Leu Arg Lys Ser Gly Val
865                 870                 875                 880
```

-continued

```
Asn Pro Ala Gln Val Asn Tyr Ile Glu Ala His Gly Thr Gly Thr Gly
                885                 890                 895

Leu Gly Asp Pro Ile Glu Leu Gln Ala Leu Gln Ser Ala Tyr Gly Ala
            900                 905                 910

Asn Leu Glu Gly Ala Asp Thr Pro Cys Tyr Leu Gly Ser Val Lys Ser
        915                 920                 925

Asn Ile Gly His Leu Glu Ser Ala Ala Met Ala Gly Leu Phe Lys
    930                 935                 940

Val Val Gln Gln Phe Ala His Glu Gln Leu Ala Pro Thr Leu His Cys
945                 950                 955                 960

Ala Ile Glu Asn Pro Tyr Leu Asn Ile Glu Gln Thr Arg Phe Gln Leu
                965                 970                 975

Val Arg Glu Lys Gln Pro Trp Pro Leu Ala Gly Ala Ala Thr Arg Phe
            980                 985                 990

Ala Gly Leu Ser Ser Phe Gly Ala Gly Gly Ala Asn Gly His Val Ile
        995                 1000                1005

Leu Gln Gln Tyr Leu Pro Lys Asp Pro Ala Gly Thr Val Pro Ala Gln
    1010                1015                1020

Ala Glu Tyr Leu Ile Ala Leu Ser Ala Pro Asn Arg Ser Gly Leu Arg
1025                1030                1035                1040

Arg Val Arg Gln Gln Leu Ala Ala Tyr Leu Arg Ala Gln Pro Gln Thr
                1045                1050                1055

Cys Leu Tyr Ser Leu Ser Tyr Thr Leu Cys Cys Ala Arg Gln His His
            1060                1065                1070

Ala Glu Arg Ala Cys Phe Val Val Gly Ser Ala Ala Ala Leu Ile Asp
        1075                1080                1085

Arg Leu Glu Ser Ala Gly Glu Ala Asn Ala Asp Ser Pro Ala Asn Gln
    1090                1095                1100

Pro Phe Ala Ser Leu Met Arg Ala Tyr Leu Gln Gly Asp Ser Val Asp
1105                1110                1115                1120

Phe Ala Gly Ser Phe Pro Val Lys Ser Leu Leu Arg Ser Ala Pro Lys
                1125                1130                1135

Tyr Pro Phe Ala Arg Asp Val Tyr Trp Ala Pro Thr Leu Gln Ala Gln
            1140                1145                1150

Ala Val Ser Ala Ala Thr Asn Pro Val Lys Pro Val Ala Pro Ser Ser
        1155                1160                1165

Ala Gln Thr Leu Asp Ser Thr Pro Ala Val Leu Leu Thr Pro Val Trp
    1170                1175                1180

Arg His Thr Glu Ser Pro Thr Leu Ser Lys Pro Ile Pro Leu Val Ala
1185                1190                1195                1200

Val Met Ala Pro Ser Glu Gln Val Leu Pro Pro Met Ile Asp Gly Ala
                1205                1210                1215

Arg Val Leu Arg Val Ser Pro Gly Thr Ala Leu Ser Phe Gln His Asp
            1220                1225                1230

Ala Leu Thr Leu Arg Pro Asp His Leu Asp Asp Phe Thr Gln Ala Leu
        1235                1240                1245

Asp Tyr Ile Ala His Glu Leu Gln Gln Glu Glu Ile Arg Trp Ile Asn
    1250                1255                1260

Cys Asn Val Pro Trp Ser Asp Ala Met Ala Leu Asn Leu Ala Lys Ala
1265                1270                1275                1280

Met Gln Ala Cys Ala Arg Pro Cys Ala Leu Leu Asn Val Ser Asp Ser
                1285                1290                1295

Arg Gln Pro Pro Glu Gln Ile Ala Met Gly Gly Val Phe Arg Val Leu
```

```
                1300              1305              1310
Ala Leu Glu Asn Thr Asp Val His Tyr Arg Gln Ala Gln Ile Ala Lys
        1315              1320              1325

Pro Ala Gly Ser Trp Glu Leu Glu Asp Trp Arg Trp Leu Leu Ala Glu
    1330              1335              1340

Gln Ala Asp Thr Thr Asp Glu Phe Lys Glu Val Glu Arg Arg Gln Glu
1345              1350              1355              1360

Glu Arg Trp Glu Arg Ser Leu Thr Ser Ile Glu Pro Ala Pro Gly Ala
            1365              1370              1375

Arg Leu Arg Glu Gly Gly Val Tyr Leu Ile Ser Gly Gly Met Gly Met
        1380              1385              1390

Ile Gly Arg Glu Ile Ala Arg Arg Leu His Ala Asp Tyr Asn Ala Lys
    1395              1400              1405

Val Ile Leu Val Gly Arg Ser Ala Leu Ser Pro Glu Arg Glu Ala Trp
1410              1415              1420

Leu Gln Gln Trp Pro Gln Gly Glu Ile Ser Tyr Leu Arg Ala Asp Ile
1425              1430              1435              1440

Ala Asp Pro Val Gln Ala Glu Arg Leu Ile Ala Asp Val Leu Gln Lys
            1445              1450              1455

His Gly Arg Leu His Gly Val Ile Gln Ser Ala Gly Val Leu Arg Asp
        1460              1465              1470

Ala Gln Val Gln Asn Lys Ser Leu Ala Asp Phe Ser Ala Val Met Ala
    1475              1480              1485

Ala Lys Val Ala Gly Thr Arg Gln Leu Asp Arg Cys Thr Ala His Leu
1490              1495              1500

Glu Leu Asp Phe Phe Cys Leu Phe Ser Ser Met Ser Ser Ile Met Gly
1505              1510              1515              1520

Asn Val Gly Gln Cys Asp Tyr Val Ala Ala Asn Arg Phe Leu Asp Glu
            1525              1530              1535

Phe Ala Ala Glu Arg Asn Gly Arg Val Arg Gln Gly Ala Arg Lys Gly
        1540              1545              1550

His Thr Leu Ser Ile Asn Trp Pro Leu Trp Ile Asp Asp Gln Asp Ser
    1555              1560              1565

Glu Asn Leu Met Asp Gln Tyr Arg Ser Leu Ala Asp Tyr Leu Lys Arg
1570              1575              1580

His Tyr Gly Phe Val Pro Leu Thr Leu Ala Gln Gly Ala Gly Leu Phe
1585              1590              1595              1600

Ile Thr Trp Ile Asn Gly Val Ala Asp Gln Tyr Asp Gln Val Met Gly
            1605              1610              1615

Leu Val Gly Asp Leu Glu Lys Ile Arg Ala Arg Phe Thr Ser Ser Thr
        1620              1625              1630

Val Gln Asn Ser Gln Gln Gln Ala Lys Asn Gly Asn Gln Asn Ala Ser
    1635              1640              1645

Gln Val Val Ala Ser Glu Ala Gln Ile Arg Ala Gly Leu Thr Arg Leu
1650              1655              1660

Val Glu Ala Leu Thr Lys Leu Ala Glu Glu Asp Ile Ser Thr Asp Lys
1665              1670              1675              1680

Ser Trp Gly Asp Leu Gly Leu Asn Ser Val Met Met Gln Thr Leu Ala
            1685              1690              1695

Gln Asp Ile Gly Lys Thr Phe Gly Ala Gln Val Pro Pro Asn Ala Leu
        1700              1705              1710

Phe Ser Tyr Asn Asn Ile Gln Arg Leu Ala Glu Tyr Leu Gln Gln Gln
    1715              1720              1725
```

```
Gly Ala Thr Leu Ala Gly Ala Ala Ser Ala Asp Asp Ala Val Ser Gln
        1730                1735                1740

Thr Gly Glu Ala Ser Ser Ala Ala Ser Ser Leu Ala Gly Val Ala Ser
1745                1750                1755                1760

Val Glu Gln Pro Leu Ala Glu Lys Arg Ser Glu Glu Leu Ser Glu Gln
            1765                1770                1775

Arg Phe Ala Ile Ile Gly Met Ser Gly Val Met Pro Gly Ala Ala Asp
        1780                1785                1790

Leu Glu Ala Phe Trp Thr Leu Leu Thr Glu Asn Arg Ser Ala Ile Arg
        1795                1800                1805

Pro Val Ala Arg Trp Gly Asp Lys Ser Tyr Tyr Ala Gly Thr Ile Asp
        1810                1815                1820

Asp Ile Glu Arg Phe Asp Ala Arg Phe Phe Gly Leu Ser Ala Arg Glu
1825                1830                1835                1840

Ala Met Leu Met Asp Pro Gln His Arg Leu Phe Leu Gln Thr Ser Tyr
            1845                1850                1855

Asn Ala Leu Thr Asp Ala Gly Tyr Ala Pro Ala Leu Leu Ser Ser Val
            1860                1865                1870

Gly Val Phe Ala Gly Val Gln Phe Asn Asp Tyr Gln Thr Leu Leu Gln
        1875                1880                1885

Thr Trp Gly Gln Ser Ser His Pro Tyr Ala Ala Thr Gly Asn Ala His
        1890                1895                1900

Ala Met Leu Ala Asn Arg Val Ser Tyr Leu Phe Asn Phe Asn Gly Pro
1905                1910                1915                1920

Ser Gln Thr Ile Asp Thr Ala Cys Ser Ser Ala Leu Val Ala Val Asn
            1925                1930                1935

Arg Gly Val Met Ser Leu Gln Arg Asn Glu Cys Asp Met Ala Leu Val
            1940                1945                1950

Gly Ala Val Ser Leu Leu Ile Asp Pro Ala Ile Ser Asp Ala Ala Gln
        1955                1960                1965

Ser Met Gly Val Leu Ser Pro Asp Tyr Arg Cys Ala Thr Phe Asp Ala
    1970                1975                1980

Asp Ala Asn Gly Tyr Val Arg Ala Glu Gly Val Gly Cys Val Val Ile
1985                1990                1995                2000

Lys Arg Leu Ala Asp Ala Gln Arg Asp Gly Asp Ser Ile Tyr Gly Val
            2005                2010                2015

Ile Glu Ala Ser Ala Glu Asn His Gly Gly Arg Ala Asn Ser Leu Thr
            2020                2025                2030

Ala Pro Asn Pro Gln Ala Gln Ser Ala Leu Leu Gln Lys Ala Tyr Thr
        2035                2040                2045

Pro Glu Leu Ala Glu Arg Val Ser Tyr Ile Glu Thr His Gly Thr Gly
    2050                2055                2060

Thr Gln Leu Gly Asp Pro Ile Glu Ile Asp Ala Leu His Gln Ala Phe
2065                2070                2075                2080

His Ala Leu Ala Pro His Lys Ser Lys Gly Ser Ile Ala Leu Gly Ala
            2085                2090                2095

Val Lys Ser Asn Val Gly His Leu Glu Pro Ala Ala Gly Ile Ala Ser
            2100                2105                2110

Leu Leu Lys Val Leu Leu Cys Leu Gln His Arg Arg Leu Pro Ala Asn
        2115                2120                2125

Ile His Phe Asn Arg Leu Asn Pro Met Ile His Leu Asn Asp Gly Pro
    2130                2135                2140
```

Phe Arg Leu Leu Thr Glu Asn Arg Asp Trp Glu Ala Thr Gly Pro Arg
2145                2150                2155                2160

Val Ala Gly Ile Ser Ser Phe Gly Phe Gly Gly Ser Asn Ala His Val
            2165                2170                2175

Val Leu Ser Glu Gly Arg Gln Ser Ala Val Val Glu Arg Ala Pro Lys
        2180                2185                2190

Pro Cys Trp Leu Val Thr Leu Ser Ala Lys Thr Pro Tyr Ser Leu Ala
    2195                2200                2205

Ala Met Lys Ala Arg Leu Leu Glu Arg Leu Gln Thr Ala Asp His Glu
2210                2215                2220

Leu Ala Asp Ile Ala Phe Thr Leu Asn Thr Gly Arg Glu Ala Phe Ala
2225                2230                2235                2240

Tyr Arg Leu Ser Trp Ile Ala Thr Ser Val Ala Asp Leu Thr Ala Gln
            2245                2250                2255

Ile Arg Ala Thr Asp Ala Thr Gly Gln Glu Lys Cys Ala Gly Lys Thr
        2260                2265                2270

Ser His Trp Thr Pro Asp Leu Ser Gln Ser Asp Trp Thr Ala Leu Met
    2275                2280                2285

Gln Thr Ala Gln Ala Gln Tyr Gln Gln Gly Ala Leu Ile Asp Trp Thr
2290                2295                2300

Pro Val Phe Ala Glu Gly Ala Tyr Arg Arg Leu His Leu Pro Gly Tyr
2305                2310                2315                2320

Val Phe Asp Thr Lys Pro Tyr Trp Phe Glu Gln Ala Ala Asp Ser Ala
            2325                2330                2335

Ala Met Lys Glu Val Asn His Gly Ser
        2340                2345

<210> SEQ ID NO 8
<211> LENGTH: 184
<212> TYPE: PRT
<213> ORGANISM: Hahella chejuensis

<400> SEQUENCE: 8

Met Leu Leu Gln Lys Glu Lys Ala Ser Val Val Ile Phe Asn Met Gln
1               5                   10                  15

Leu Glu Leu Ile Pro Leu Leu Gln Asn Gly Thr Gln Leu Leu Asn Asp
            20                  25                  30

Cys Arg Trp Leu Ala Asp Met Cys Cys Asp Leu Gln Val Pro Thr Gln
        35                  40                  45

Ile Ile Glu His Lys Lys Leu Gly Lys Leu Ser Gln Ser Leu Thr Glu
    50                  55                  60

Val Ala Arg Asp Ala Glu Phe Leu Glu Lys Thr His Phe Asp Phe Met
65                  70                  75                  80

Gln Glu Gln Ala Val Ala His Ser Val Glu Ala Ala Arg Arg Asp His
                85                  90                  95

Tyr Val Leu Ala Gly Ala Glu Thr His Val Cys Leu Leu Gln Ser Ala
            100                 105                 110

Leu Arg Leu Lys Ala Gln Gly Lys Glu Val Phe Leu Leu Ala Asp Thr
        115                 120                 125

Cys Ser Ala Arg Ser Arg Thr Asp His Glu Ala Ala Leu Arg Arg Leu
    130                 135                 140

Glu Gln Asn Gly Val Gln Leu Ile Thr Arg Glu Met Phe Phe Phe Glu
145                 150                 155                 160

Leu Ile Arg His Ser Glu Tyr Pro Asn Tyr Leu Asp Leu Ala Met Lys
                165                 170                 175

Tyr Leu Asp Gly Arg Tyr Ile Arg
            180

<210> SEQ ID NO 9
<211> LENGTH: 472
<212> TYPE: PRT
<213> ORGANISM: Hahella chejuensis

<400> SEQUENCE: 9

Met Lys Gly Ser Asn Ile Ala Val Ile Gly Gly Gly Ala Gly Ala
 1               5                  10                  15

Met Ala Ala Trp Leu Leu Ser Lys Asn Asn Gln Val Thr Leu Phe Glu
            20                  25                  30

Ala Ser Asp Tyr Leu Gly Gly His Ala Tyr Ser His Pro Val Glu Thr
            35                  40                  45

Glu Thr Gly Thr Gln Tyr Ile Asp Met Gly Val Glu Tyr Phe Asn Glu
    50                  55                  60

Arg Leu Ser Pro Asn Leu Cys Ala Leu Leu Thr His Phe Gly Val Asp
 65                 70                  75                  80

Ser Tyr Val Ala Pro Leu Thr Met His Val Asp Phe Pro Gly Glu Gly
                85                  90                  95

Arg Phe Trp Asn Asn Leu Thr Gly Lys Gly Glu Leu Gly Glu Glu Leu
            100                 105                 110

Arg Glu Glu Phe Asp Arg Phe His Leu Asp Met Ala Thr Val Leu Ser
            115                 120                 125

Ser Gly Asp Glu Arg Tyr Lys Lys Met Ser Ile Gly Gln Tyr Leu Asp
130                 135                 140

Glu Gln Gly Tyr Ser Asp Ala Phe Lys His Gln Ala Leu Ser Pro Leu
145                 150                 155                 160

Met Thr Val Tyr Ser Gly Cys Asn Ala Pro Ser Leu Asp Tyr Thr Leu
                165                 170                 175

Met Tyr Val Ala Ile Ser Phe Asn Met Asn Leu Leu Ser Phe Phe Ser
            180                 185                 190

Pro Gly Tyr Trp Arg Lys Ala Lys Gly Gly Val Asn Gly Tyr Leu Lys
            195                 200                 205

Arg Ile Ala Glu Glu Leu Gly Glu Arg Val Gln Leu Asn Thr Pro Val
    210                 215                 220

Gln Arg Val Thr Pro Ser Ala Ser Gly Val Thr Val Glu Phe Asn Gly
225                 230                 235                 240

Lys Ser Gln Arg Phe Asp Gln Val Ile Phe Ala Thr His Ala Asp Val
                245                 250                 255

Thr Leu Ser Ile Leu Ala Thr Thr Glu Ser Leu Tyr Gln Asp Ile Leu
            260                 265                 270

Gly Gly Phe Glu His Val Pro Val Lys Ser Phe Leu His His Asp Glu
            275                 280                 285

Arg Trp Ile Ser Pro Gln Gly Glu Gly His Tyr Cys Gln Phe Lys Met
    290                 295                 300

Pro Asp Ser Phe Asn Ile Ala Ala Pro Glu Ala Gln Phe Gly Thr Leu
305                 310                 315                 320

Thr Arg Val Asn Asn Val Leu Pro Pro Tyr Arg Asn Leu Asp Lys Pro
                325                 330                 335

Leu Leu Val Thr Phe Asp Pro Lys Asp Ser Ile Arg Pro Glu Arg Ile
            340                 345                 350

Ala Cys Glu Arg Ser Trp Lys Leu Pro Lys Leu Arg Pro Val Asp Phe

```
                    355                 360                 365
Tyr Arg Lys Thr Arg Ile Lys Glu Ile Gln Gly Val Asn Asn Leu Trp
    370                 375                 380

Phe Cys Gly Thr Asp Thr Ser Leu Thr Gly His Glu Gly Ala Ile Val
385                 390                 395                 400

Ser Ala Met Val Ile Ala Asp Arg Leu Gly Ala Ala Tyr Pro Tyr Arg
                405                 410                 415

Asp Asn Thr Leu Ala Tyr Val Gln Phe Lys Val Ile Lys Asp Ile Met
            420                 425                 430

Gly Val Asn Lys Pro Gly Glu Lys Val Ala Ser Trp Ile Gly Asp Ala
        435                 440                 445

Ile Phe Arg Val Ala Lys Ala Leu Ser Leu His Lys Glu Gln Ser His
    450                 455                 460

Lys Phe Ile Lys Asp Leu Met Val
465                 470

<210> SEQ ID NO 10
<211> LENGTH: 293
<212> TYPE: PRT
<213> ORGANISM: Hahella chejuensis

<400> SEQUENCE: 10

Met Glu Ile Leu Met Phe Pro Gly Gln Gly Ser Gln His Pro Gly Met
1               5                   10                  15

Gly Lys Asp Leu Phe Glu Arg Tyr Pro Thr Gln Cys Arg Asp Ala Glu
            20                  25                  30

Glu Ile Leu Gly Tyr Asp Leu Val Asp Leu Cys Leu Gln Asp Arg Glu
        35                  40                  45

Gly Arg Leu Asn Gln Thr Ala Tyr Thr Gln Pro Ala Leu Tyr Phe Val
    50                  55                  60

Cys Cys Leu Thr Tyr Leu Asp Tyr Leu Arg Gln Ala Gly Arg Arg Phe
65                  70                  75                  80

His Asp Ser Phe Asp Gly Arg Leu Leu Gly His Ser Leu Gly Leu Phe
                85                  90                  95

Pro Ala Leu Phe Ala Ala Gly Val Phe Asp Leu Met Thr Gly Leu Arg
            100                 105                 110

Ile Val Ala Lys Arg Gly Glu Leu Met Gln Ala Ile His Gly Gly Gly
        115                 120                 125

Met Leu Ala Val Leu Gly Val Ser Ala Asp Arg Leu Arg Glu Lys Leu
    130                 135                 140

Ile Gln Leu Asp Cys Phe Asp Val Asp Val Ala Asn Asp Asn Ala Pro
145                 150                 155                 160

Gly Gln Val Val Leu Ser Gly Gln Glu Ala Arg Met Arg Gln Leu Ser
                165                 170                 175

Pro Arg Leu Glu Lys Asp Gly Leu Arg Cys Val Ser Leu Pro Val Ser
            180                 185                 190

Gly Ala Phe His Ser Arg Tyr Met Glu Pro Cys Arg Val Glu Phe Thr
        195                 200                 205

Glu Phe Leu Leu Gly Leu Asp Leu His Ala Pro Gln Lys Thr Val Ile
    210                 215                 220

Ser Ser Ala Ser Gly Asp Ala Ile Ser Gly Glu His Leu Ile Glu Glu
225                 230                 235                 240

Met Ala Phe Gln Leu Val Lys Pro Val Arg Trp Ser Leu Thr Ile Gln
                245                 250                 255
```

```
Ser Leu Leu Arg Arg Tyr Pro Gln Ala Arg Phe Val Glu Leu Gly Pro
            260                 265                 270

Gly Arg Val Leu Thr Asn Leu Gln Gly Lys Ile Gln His Ala Val Ala
        275                 280                 285

Thr His Ala Gln Ala
    290

<210> SEQ ID NO 11
<211> LENGTH: 1911
<212> TYPE: PRT
<213> ORGANISM: Hahella chejuensis

<400> SEQUENCE: 11

Met Arg Asp Met Glu Phe Ala Gly Ile Ser Gln Thr Ala Ile Asp Ser
1               5                   10                  15

Leu Val Phe Ser Pro Glu Trp Lys Ile Leu Pro Leu Ala Ala Ala Ser
            20                  25                  30

Gly Ala Glu Ala Pro Trp Val Ile Ile Val Pro Ser Gln Ala Ala
        35                  40                  45

Leu Arg Glu Glu Ile Ala Asp Tyr Thr Pro Gln Ala Glu Val Arg Leu
    50                  55                  60

Leu Asp Pro Gln Thr Ile Asp Asp Leu Ala Arg Ala Val Asp Lys Asn
65                  70                  75                  80

Pro Ala Leu Arg Leu Cys Phe Val Thr Arg Thr Pro Trp Arg Ala Ala
                85                  90                  95

Val Pro Asp Glu Asp Val Ser Ala Phe Phe His Leu Leu Lys Ala Leu
            100                 105                 110

Arg Asp Lys Pro Ala Val Lys Leu Asp Val Phe Thr Asp Lys Ala Val
        115                 120                 125

Ala Ser Pro Leu Phe Glu Ser Val Thr His Pro Val Asp Gly Val Tyr
    130                 135                 140

Val Gly Leu Ala Gln Thr Leu Ala Lys Glu Arg Pro Glu Trp Thr Val
145                 150                 155                 160

Arg Ser Phe Ser Leu Gln Lys Leu Thr Ala Asp Val Leu Gln Asp Leu
                165                 170                 175

Leu Arg Ile Ser Leu Pro Thr His Pro Gly Thr Pro Val Cys Ile Ala
            180                 185                 190

Asp Gly Arg Tyr Gly Val Ala Asp Met Gln Pro Thr Thr Leu Asn Pro
        195                 200                 205

Trp Pro Ala Gln Ser Ala Phe Arg Gln Gln Gly Thr Tyr Val Ile Leu
    210                 215                 220

Gly Gly Ala Gly Gly Leu Gly Gly Lys Leu Ala Glu Tyr Leu Ala Ala
225                 230                 235                 240

Arg Tyr Gln Ala Arg Leu Val Ile Leu Gly Arg Ser Glu Ala His
                245                 250                 255

Asp Leu Leu Met Arg Leu Arg Asp Leu Gly Ala Ala Glu Ala His Tyr
            260                 265                 270

His Ser Val Asp Leu Ser Asp Arg Ala Ala Leu Gln Thr Val Leu Asp
        275                 280                 285

Gln Tyr Ala Val Ile His Gly Val Val His Ser Ala Leu Val Leu Glu
    290                 295                 300

Asp Ala Ser Leu Ala Ala Met Ser Glu Gln Thr Leu Phe Asn Val Leu
305                 310                 315                 320

Arg Pro Lys Val His Gly Ala Tyr Asn Leu Ala Arg Ala Leu Lys Gly
                325                 330                 335
```

```
Arg Thr Leu Asp Phe Cys Leu Phe Phe Ser Ser Ile Gln Ser Tyr Ile
            340                 345                 350

Ala Asn Pro Gly Gln Gly Asn Tyr Thr Ala Ala Cys Val Ala Lys Asp
            355                 360                 365

Ala Phe Ala Asp Leu Leu His Asn Gly Leu Met Ile Asn Ser Lys Val
            370                 375                 380

Ile Asn Trp Gly Tyr Trp Gly Ser Val Gly Val Ala Ser Glu Thr
385                 390                 395                 400

Tyr Arg Glu Arg Met Lys Lys Leu Gln Ile Gly Ser Ile Glu Val Asp
                405                 410                 415

Glu Gly Leu Ala Val Ile Glu Arg Phe Leu Val Thr Glu Arg Arg Gln
            420                 425                 430

Ile Thr Val Val Lys Ala Ser Asp Leu Ala Leu Lys Arg Leu His Ile
            435                 440                 445

Ala Pro His Thr Ala Val Gln Lys Leu Met Pro Gln Asn Val Met Ala
            450                 455                 460

Gln Thr Ser Pro Gln Leu Lys Ala Gln Glu Pro Ala Ala Pro Ala Thr
465                 470                 475                 480

Gly Ala Asp Leu Ile Pro Ala Tyr Arg Thr Gln Asp Pro Leu Val Ala
                485                 490                 495

Arg Asn Glu Ala Met Ser Ala Ala Leu Gln Glu Tyr Ala Arg Trp Arg
            500                 505                 510

Leu Ser Gln Thr Pro Met Pro Glu Thr Ile Ala Pro Lys Phe Gly Lys
            515                 520                 525

Leu Ala Ala Leu Arg Ser Ile His Ala Gly Ser Pro Gly Arg
            530                 535                 540

Glu Gln Val Ile Asp Leu Tyr Pro Glu Leu Lys Gly His Ile Arg Leu
545                 550                 555                 560

Leu Asp Gln Cys Ile Asp Asn Leu Pro Ala Ile Leu Arg Gly Glu Thr
                565                 570                 575

Asn Pro Leu Ser Val Ile Phe Pro Asp Gly Gly Phe Glu Leu Val Glu
            580                 585                 590

Pro Val Tyr Arg Asp Asn Pro Ile Ala Asp Tyr Phe Asn Gln Val Val
            595                 600                 605

Ala Arg Ile Val Ala Asn Leu Gln Lys Ala Arg Ala Gly Arg Pro Leu
            610                 615                 620

Arg Ile Ile Glu Ile Gly Ala Gly Thr Gly Ser Thr Thr Gln Phe Val
625                 630                 635                 640

Leu Pro Glu Leu Thr Pro Asp Asn Val Ser Tyr Thr Phe Thr Asp Leu
                645                 650                 655

Ser Phe Ala Phe Leu Asn Lys Ala Arg Arg Phe Ala Asp Tyr Pro
            660                 665                 670

Phe Val Glu Tyr Lys Ile Cys Asn Ile Glu Lys Pro Pro Ala Phe Glu
            675                 680                 685

Gln Pro Phe Asp Val Val Ile Ala Thr Asn Val Ile His Ala Thr Ser
            690                 695                 700

Asp Leu Pro Glu Thr Leu Arg Gln Val Arg Arg Leu Leu Ala Asp Asp
705                 710                 715                 720

Gly Val Phe Val Leu Asn Glu Ile Thr Ser Cys Gln Asp Tyr Ala Thr
                725                 730                 735

Leu Thr Phe Gly Leu Thr Asp Gly Trp Trp Leu Ser Gln Asp Pro Tyr
            740                 745                 750
```

```
Arg Ile Pro Asn Ser Pro Leu Leu Ser Gly Asp Ser Trp Arg Arg Leu
        755                 760                 765
Met Leu Gln Ala Gly Phe Gln Gly Val Asp Ala His Gly Gly Glu Asp
    770                 775                 780
Gln Gln Val Met Val Gly Phe Ala Gly Ala Asp Ala Gln Gln Gly Ala
785                 790                 795                 800
Val Ser Gln Asn Thr Ala Pro Gln Thr Glu Ala Ser Pro Ile Gln Pro
                805                 810                 815
Ser Pro Asp Ser Ala Ala Glu Gln Ser Ala Ser Gln Ala Gly Val Ala
            820                 825                 830
Ser Gln Ala Ser Ile Glu Ala Phe Leu Gln Gln Ala Ile Ala Glu Val
        835                 840                 845
Leu Gln Phe Asp Pro Ser Glu Ile Glu Arg Asp Met Pro Phe Ser Glu
    850                 855                 860
Met Gly Val Asp Ser Leu Ile Ser Met Glu Leu Leu Lys Pro Ile Lys
865                 870                 875                 880
Glu Lys Thr Gly Tyr Leu Pro Ala Thr Ile Leu Phe Glu Tyr Pro Thr
                885                 890                 895
Ile Arg Gln Leu Ala Glu His Ile Val Ala Ser Gly Leu Ala Trp Asp
            900                 905                 910
Glu Gly Ala Thr Asn Gln Ala Thr Ala Ala Leu Thr Val Glu Glu
        915                 920                 925
Thr Ala Val Thr Pro Pro Gly Arg Asp Ser Leu Thr Glu Ile Met Asn
    930                 935                 940
Gln Val Arg Ala Val Ile Ala Asp Thr Met Met Met Glu Pro Glu Asp
945                 950                 955                 960
Val Glu Ala Asp Thr Pro Phe Gln Glu Tyr Gly Val Asp Ser Ile Ile
                965                 970                 975
Ser Leu Glu Leu Ile Arg Pro Leu Lys Glu Ile Phe Gly Tyr Leu Pro
            980                 985                 990
Ala Thr Val Leu Phe Glu Tyr Pro Ser Leu Arg Gln Leu Ala Ala Tyr
        995                 1000                1005
Leu Ala Thr Thr Val Ala Thr Ser Pro Ser Gly Glu Thr Thr Pro Asp
    1010                1015                1020
Ser Ser Pro Ala Arg Ala Ser Glu Thr Gly Glu Cys Ala Gly Asn Ser
1025                1030                1035                1040
Gly Thr Asp Glu Arg Ala Gln Asp Ala Gln Pro Ser Ser Asp Ala Pro
                1045                1050                1055
Glu Lys Ser Leu Trp Arg Pro Gly Asp Ile Ala Ile Val Gly Met Ala
            1060                1065                1070
Ala Arg Leu Pro Lys Ala Gln Asp Val Ala Arg Phe Trp Glu Asn Leu
        1075                1080                1085
Arg Asn Gly Arg Asp Cys Thr Asp Val Ile Pro Ala Glu Arg Trp Lys
    1090                1095                1100
Gln Glu Gly Phe Leu Ser Glu Ala Pro Leu Asn Gly Arg Gly Ser Tyr
1105                1110                1115                1120
Thr Asn Arg Gly Ala Phe Ile Asp Asp Val Asp Ala Phe Asp His Val
                1125                1130                1135
Phe Phe Asn Leu Thr Pro Asn Glu Ala Ala Arg Met Asp Pro Gln Glu
            1140                1145                1150
Arg Ile Met Leu Glu Gln Thr Tyr Arg Ser Met Leu Asp Ala Gly Tyr
        1155                1160                1165
Thr Arg Lys Gln Trp Ala Gly Ser Asp Thr Ala Val Phe Val Gly Val
```

```
                    1170            1175            1180
Met Asn Gly Asp Tyr Ala Trp His Thr Pro Ala Gln Thr Thr Thr Ala
1185            1190            1195            1200

Pro Ala Thr Ser Leu Phe Trp Ser Met Ala Asn Arg Ala Ser Tyr Phe
            1205            1210            1215

Phe Asp Trp Arg Gly Pro Ser Met Ala Val Asp Thr Ala Cys Ser Ala
        1220            1225            1230

Ser Leu Thr Ala Leu His Leu Ala Cys Gln Ala Leu Lys Asn Gly Asp
        1235            1240            1245

Cys Glu Gln Ala Val Val Gly Gly Val Asn Leu Ile Thr His Pro Arg
    1250            1255            1260

His Tyr Glu Leu Leu Cys Gly Leu His Met Leu Ser Arg Ser Glu Gln
1265            1270            1275            1280

Cys Lys Pro Phe Gly Ala Asn Ala Asp Gly Phe Val Asp Gly Glu Gly
            1285            1290            1295

Val Val Cys Leu Val Val Lys Arg Ala Glu Asp Ala Ile Arg Asp Lys
        1300            1305            1310

Asp Arg Val Tyr Ala Phe Ile Lys Gly Ser Ala Ile Asn Ala Gly Gly
        1315            1320            1325

Arg Ser Asn Gly Tyr Thr Ala Pro Asn Pro Glu Ala Gln Ala Ala Leu
    1330            1335            1340

Ile Gly Lys Ala Leu Arg Ala Ala Gly Val Ser Pro Gln Glu Val Gly
1345            1350            1355            1360

Tyr Val Glu Ala His Gly Thr Gly Thr Glu Leu Gly Asp Pro Ile Glu
            1365            1370            1375

Leu Arg Ala Leu Ser Lys Ser Tyr Gly Asp Ala Ala Pro Gln Ser Ile
        1380            1385            1390

Arg Leu Gly Ser Val Lys Ser Asn Leu Gly His Leu Glu Ser Ala Ala
        1395            1400            1405

Gly Leu Cys Gly Val Leu Lys Ala Val Leu Gln Met His His Gly Glu
    1410            1415            1420

Trp Val Pro Ser Leu His Ala Glu Gln Leu Asn Pro His Leu Asp Phe
1425            1430            1435            1440

Thr Gln Thr Pro Phe Leu Leu Asn Arg Glu Arg Arg Val Trp Asp Ala
            1445            1450            1455

Thr Ala Pro Arg Val Ser Ala Val Ser Ser Phe Gly Ala Gly Gly Gly
        1460            1465            1470

Asn Ala His Val Val Ile Gln Gly Val Ala Gln Ala Ser Val Asp Ala
        1475            1480            1485

Ala Pro Arg Ala Ala Arg Asp Ser Tyr Val Ile Pro Leu Ser His His
    1490            1495            1500

Cys Asn Ala Gly Leu Gln Gln Thr Met Asp Ser Leu Arg Glu Trp Leu
1505            1510            1515            1520

Gln Gly Arg Gln Val Asp Met Asp Ala Leu Ala Tyr Thr Leu Ala Cys
            1525            1530            1535

Ala Arg Asp His Asp Arg Phe Arg Arg Ala Leu Val Cys Arg Asp Gln
        1540            1545            1550

Ala Asp Leu Ile Glu Gln Leu Gly Gln Asp Leu Gln Val Val Thr Ala
        1555            1560            1565

Ala Ser Arg Lys Glu Ala Ser Gly Pro Leu Gln Glu Gln Pro Pro Gln
    1570            1575            1580

Arg Leu Thr Arg Asp Asn Ala Glu Arg Val Ala Ala Leu Tyr Glu Ala
1585            1590            1595            1600
```

-continued

```
Gly Gly Asp Leu Pro Trp Arg Asp Phe Tyr Pro Gln Arg Arg Leu Ala
            1605                1610                1615

Ala Val Pro Pro Tyr Val Phe Ile Arg His Arg His Trp Ile Asp Ser
        1620                1625                1630

Val Glu Ser Asn Phe Lys Gly Phe Thr Ser Leu Thr Gln Ala His Arg
    1635                1640                1645

Ile Asn Gly Arg Ala Met Ala Pro Ala Ala Trp Thr Leu Ser Thr Leu
 1650               1655                 1660

Cys Glu Ser Ala Asp Asp Gly Gly Phe Ala Asn Ile Met Trp Lys Asp
1665                1670                1675                1680

Lys Ile Thr Asp Pro Gln Trp Val Asp Val Ile Glu Glu Gly Glu Arg
            1685                1690                1695

Thr Leu Phe Val Gly Arg Gly Gly Tyr Thr Gln Tyr Cys Ser Ala Glu
        1700                1705                1710

Arg Thr Pro Asp Ala Ser Ala Pro Ala Asn Ile Ala Ala Val Leu Ala
    1715                1720                1725

Arg Leu Gly Met Glu Asn Pro Pro Asn Pro Leu Gln Glu Met Gly Ala
 1730               1735                1740

Ile Pro Arg Leu Ser Gln Ala Gln Ile Tyr Ala Asp Phe Lys Gln Arg
1745                1750                1755                1760

Gly Tyr Asp Tyr Gly Ala Pro Leu Gln Gly Ile Arg Trp Ala Gln Val
            1765                1770                1775

Lys Pro Gly Leu Val Arg Ala Leu Leu Gln Val Asp His Asp Trp Gly
        1780                1785                1790

Arg Leu Val Ser Pro Ala Leu Leu Asp Ser Gly Leu Gln Leu Ala Ile
    1795                1800                1805

Leu Ala Ala Gly Ser Gly Ala Glu Ser Ser Gly Glu Gly Thr Val Phe
 1810               1815                1820

Met Pro Tyr His Leu Gly Arg Leu Val Val Lys Arg Leu Pro Asp Asn
1825                1830                1835                1840

Glu Ala Val Tyr Gly Tyr Cys Leu Glu Arg Thr Ser Gly Gln Ala Ser
            1845                1850                1855

Lys Ala Arg Arg Phe Asp Phe Tyr Phe Thr Arg Gln Gly Glu Val
        1860                1865                1870

Leu Ile Leu Leu Glu Asp Met Val Ser Val Val Arg Pro Asp Ala
    1875                1880                1885

Glu Asp Asp Val Asp Thr Arg Pro Arg Gln Val Arg Pro Glu Pro Arg
 1890               1895                1900

Phe Glu Val Phe Asp Leu Ser
1905                1910

<210> SEQ ID NO 12
<211> LENGTH: 285
<212> TYPE: PRT
<213> ORGANISM: Hahella chejuensis

<400> SEQUENCE: 12

Met Ala Arg Pro Met Met Ser Thr Ser Val Arg Ala Gly Asp Ser Phe
  1               5                   10                  15

Phe Asp Thr Gln Gly Arg Trp Arg Arg Leu Pro Ala Gly Asp Gly Tyr
             20                  25                  30

Arg Val Ala Leu Arg Asp Asp His Pro Tyr Phe Ser His His Arg Val
         35                  40                  45

Arg Gly Trp Lys Val Leu Pro Gly Val Val Tyr Leu Glu Leu Ala Leu
```

```
                    50                  55                  60
Ser Ala Val Ala Arg Ala Arg Pro Asp Phe Asn Thr Cys Phe Val Asp
 65                  70                  75                  80

Glu Val Val Trp Leu Arg Pro Val Leu Ala Asn Thr Pro Glu Thr Glu
                 85                  90                  95

Ile Asp Val Gln Leu Ala Pro Ile Ser Pro Thr Arg Ile Glu Phe Arg
                100                 105                 110

Ile Ala His Gly Gly Glu Val Cys Gly Gly Val Leu Asn Ala Gln
            115                 120                 125

Thr Val Ser Gly Arg Thr Glu Ala Leu Ala Thr Pro Leu Cys Val Arg
130                 135                 140

Ser Gln Val Gly Ala Glu Thr Arg Asp His Phe Pro Arg Ser Glu Val
145                 150                 155                 160

Tyr Ala Ala Phe Ala Asp Met Gly Ile Val Tyr Gly Pro Tyr Phe Gln
                165                 170                 175

Arg Ile Ser Tyr Val Gln Arg Leu Ser Asn Lys Ala Leu Ser Trp Leu
                180                 185                 190

Ser Asn Tyr Asp Gly Val Phe Leu Gly Trp Ala Gly Leu Leu Asp Cys
            195                 200                 205

Ala Phe Gln Ala Gly Met Ala Ile Ser Ile Gly Glu Arg Arg Glu Ser
            210                 215                 220

Leu Met Pro Tyr Ser Leu Gly Arg Leu Thr Leu His Gln Ala Leu Pro
225                 230                 235                 240

Glu Gln Ala Leu Gly Ser Ala Phe Val Leu Thr Glu Lys Leu Ser Pro
                245                 250                 255

Phe Arg Thr Asn Leu Thr Val Phe Asp Glu Ala Tyr Thr Pro Leu Leu
                260                 265                 270

Ser Val Phe Asp Leu Gly Val Lys Pro Ser His Leu Gln
            275                 280                 285

<210> SEQ ID NO 13
<211> LENGTH: 1680
<212> TYPE: PRT
<213> ORGANISM: Hahella chejuensis

<400> SEQUENCE: 13

Met Lys Leu Arg Lys Ala Thr His Tyr Glu Gln Phe Gln Trp Leu Arg
  1               5                  10                  15

Tyr Arg Arg Asn Pro Asp Asp Pro Gly Leu Thr Leu Ser Tyr Gln Phe
                 20                  25                  30

Lys Ile Thr Gly Asn Ile Glu Phe Gln Ala Leu Asn Arg Ala Leu Lys
             35                  40                  45

Ala Val Leu Leu Asn Gly Phe Asn Gly Leu Leu Ser Tyr Phe Leu Asp
 50                  55                  60

Arg Gly Gly Ser Leu Leu Val Gly Cys Asn Pro Leu Pro Asp Lys Val
 65                  70                  75                  80

Val Asp Ile Ile Thr Asp Lys Ala Glu Trp Ser Asn Leu Glu Pro Ile
                 85                  90                  95

Asp Pro Ala Gly Asp Lys Leu Phe Arg Phe Ala Cys Phe Ile Glu Asn
                100                 105                 110

Glu Ser Ile Thr Gly Leu Lys Phe Glu Phe Ser His Leu Val Phe Asp
            115                 120                 125

Gly Glu Cys Tyr Gln Pro Phe Leu Asn Thr Phe Ala Asp Tyr Trp His
            130                 135                 140
```

```
Arg Arg Glu Gly Gly His Gly Glu Ala Arg Asp Gly Gly Ile Ser
145                 150                 155                 160

Phe Leu Pro Ile Gly Asp Ala Pro Val Ala Pro Ser Ser Val Asp Phe
                165                 170                 175

Trp Lys Glu Ala Leu His Gly Ala Arg Leu Phe Gln Pro Leu Pro Phe
            180                 185                 190

Cys Tyr Lys Thr Pro Lys Glu Lys Gly Val Tyr Leu Ser Val Lys Arg
        195                 200                 205

Thr Leu Ala Val Lys Arg Thr Leu Gly Ile Asn Lys Arg Thr Gln Ala
210                 215                 220

Val Glu Pro Ala Leu Asp Gly Asp Arg Phe Ala Ser Ile Ser Ala Met
225                 230                 235                 240

Leu Glu Gly Cys Gly Val Thr Leu Phe Gln Tyr Val Ala Val Thr
                245                 250                 255

Ala Ala Val Ile Arg Leu Tyr Ser Ala Thr Gln Glu His Asp Glu Glu
                260                 265                 270

Ala Val Thr Ile Ala His Thr Val Asn Cys Arg Gly Glu Arg Gln Ala
            275                 280                 285

Tyr Gly Cys Tyr Thr Asn Leu Ile Pro Leu Phe Ile Lys Ala Asp Pro
    290                 295                 300

Ala Gln Ser Gly Ala Gly Leu Leu Ala Gly Val Lys Gln Ala Arg Glu
305                 310                 315                 320

Ala Val Arg Glu His Gln His Thr Pro Thr Gln Gln Leu Ile Glu Trp
                325                 330                 335

Ala Asp Pro Arg Ala Asn His Ala Gly Arg Leu Phe Asn Leu Val Val
            340                 345                 350

Asn Ala Ser Asp Gly Leu Val Pro Tyr Ala Ala Pro Glu Met Ala Gly
        355                 360                 365

Cys Lys Val Glu Leu Thr Glu Pro Pro His Thr Gly Gly Pro Asn Asp
370                 375                 380

Leu Ala Ile Asn Tyr Ser Cys Asp Gly Glu Gln Leu Leu Leu Ser Phe
385                 390                 395                 400

Asp Ser Ser Ser Arg Phe Val Ser Arg Glu Thr Leu Thr Ser Leu Ala
                405                 410                 415

Asp Asn Phe Val Lys Val Ala Ala Tyr Ile Ala Ala Ser Pro Glu Arg
            420                 425                 430

Pro Leu His Glu Cys Ser Leu Ser Gln Pro Leu Thr Pro Val Ile Cys
        435                 440                 445

Gly Glu Arg Asn Glu Ala Ala Pro Gln Val Arg Ile Leu Glu Arg Val
450                 455                 460

Ala Asn Ala Ala Arg Leu Gln Ala Asn Ala Pro Ala Val Ser Asp Glu
465                 470                 475                 480

Arg Thr Ser Leu Thr Tyr Arg Gln Thr Tyr Ala Ala Ile Gly Arg Leu
                485                 490                 495

Tyr Arg Asp Ile Ala Ala His Ser Asp Ser Ser Ala Ser Ala Ala Ala
            500                 505                 510

Ser Ser Ala Ile Gly Val Phe Val Glu Arg Thr Ala Ala Ala Pro Val
        515                 520                 525

Ala Tyr Leu Gly Ala Leu Ala Ser Gln Arg Ala Phe Thr Pro Met Asp
        530                 535                 540

Pro Leu Leu Pro Asp Glu Arg Leu Gly Tyr Met Met Asp Val Ser Asn
545                 550                 555                 560

Val Gly Val Ile Leu Val Asp Gly Gly Thr Arg Ala Arg Ala Ala Ala
```

-continued

```
                565                 570                 575

Leu Phe Pro Gly Ala Pro Leu Ile Asp Val Glu Ser Ile His Met
            580                 585                 590

Ala Thr Thr Ala Ser Ala Gly Ala Glu Asp Glu Leu Glu His Ala Leu
                595                 600                 605

Ala Ala Asp Ala His Leu Asp Glu Thr Ala Tyr Val Met Phe Thr Ser
610                 615                 620

Gly Ser Thr Gly Arg Pro Lys Gly Val Ala Ile Ser Ala Arg Asn Leu
625                 630                 635                 640

Ala Asn Phe Leu Val Ala Met Gln Gly Val Pro Gly Phe Gln Pro Gly
            645                 650                 655

Glu Arg Met Leu Ala Leu Thr Pro Ile Ser Phe Asp Ile Ser Ile Leu
            660                 665                 670

Glu Leu Leu Leu Pro Leu Met Cys Gly Gly Glu Val His Ile Val Ser
            675                 680                 685

Asp Gln Thr Arg Leu Ser Ala Glu Leu Leu Gly Glu Ala Leu Asn Gln
            690                 695                 700

His Lys Val Asp Val Ala Gln Ala Thr Pro Ser Thr Trp Arg Met Leu
705                 710                 715                 720

Gln Gln Ala Gly Trp Arg Ala Thr Gly Glu Leu Thr Ile Leu Cys Gly
            725                 730                 735

Gly Glu Ala Leu Asp Lys Glu Leu Ala Gln Tyr Leu Leu Gln Gln Thr
            740                 745                 750

Gly Arg Leu Tyr Asn Met Tyr Gly Pro Thr Glu Ala Thr Ile Trp Ala
            755                 760                 765

Ser Cys Arg Arg Val Thr Glu Ala Gly Arg Ile Pro Leu Gly Arg Pro
770                 775                 780

Val Leu Asn Ser Glu Tyr Tyr Ile Leu Asp Ala Lys Gly Asp Ser Val
785                 790                 795                 800

Thr Pro Gly Met Gln Gly Glu Leu Thr Ile Ala Gly Glu Cys Val Gly
            805                 810                 815

Lys Gly Tyr Leu Asn Ala Pro Ser Glu Gln Ala Phe Ile Thr Leu Pro
            820                 825                 830

Asn Gly Val Arg Ala Tyr Lys Thr Gly Asp Ile Val His Tyr Leu Ser
            835                 840                 845

His Gln Asp Ile Glu Tyr Val Gly Arg Arg Asp Ser Gln Tyr Lys Val
850                 855                 860

Asn Gly Tyr Arg Val Asp Thr Gly Glu Val Ser His Arg Leu Lys Glu
865                 870                 875                 880

Phe Ala Pro Asp Ala Ala Phe Phe Thr Val Val Arg His Lys Pro Glu
            885                 890                 895

Ala His Leu Cys Cys Phe Val Trp Ala Pro Glu Asn Ser Gly Phe Asp
            900                 905                 910

Val Asp Val Ala Leu His Trp Cys Arg Arg Thr Leu Pro Tyr Tyr Met
            915                 920                 925

Thr Pro Lys Ala Leu His Arg Leu Ser Arg Ile Pro Leu Thr Ala Asn
            930                 935                 940

Gly Lys Ala Asp Val Lys Phe Leu Ser Glu Ala Pro Met Thr Glu Leu
945                 950                 955                 960

Pro Leu Met Thr Gln Pro Ser Ser Val Val Ala Thr Pro Arg Pro Thr
            965                 970                 975

Ala Ala Gln Glu Gln Val Ile Gln Gln Ala Ile Gln Asn Ile Leu Leu
            980                 985                 990
```

```
Glu Lys Leu Asp Val Ala Ala Pro Asp Leu Asp Gln Pro Leu Gly Trp
    995                 1000                1005

Leu Gly Leu Asn Ser Ile Ser Tyr Asn Leu Leu Ala Ala Ala Ile Gln
1010                1015                1020

Gln Arg Phe Asp Ile Thr Phe Arg Ser Tyr Glu Phe Tyr Gln Phe Asn
1025                1030                1035                1040

Thr Ile Asn Glu Val Ala Gly Ala Ile Arg Gln Arg Gln Ser Pro Gln
                1045                1050                1055

Gln Gly Ala Arg Pro Gln Thr Ser Gly Met Asp Arg Arg Gln Glu Arg
                1060                1065                1070

Asn Gly Asp Asp Arg Leu Ala Ile Val Gly Met Ala Ala Thr Leu Pro
            1075                1080                1085

Gly Gly Asp Asp Ala Glu Thr Phe Trp Arg Ala Leu Leu Asp Arg Lys
            1090                1095                1100

Asp Cys Ile Ala Ala Ala Pro Ala Asp Arg Ser Leu Pro Gly Tyr Arg
1105                1110                1115                1120

Ala Gly Phe Ile Ser Ser Val Arg Gly Phe Asp Ala Arg Phe Phe Ser
                1125                1130                1135

Ile Ser Pro Leu Glu Ala Thr Arg Met Asp Pro Arg Gln Arg Leu Leu
            1140                1145                1150

Leu Gln Ala Ala Trp Lys Ala Leu Glu Asp Ala Gly Tyr Ala Pro Ser
        1155                1160                1165

His Leu Ser Gly Gly Arg Ile Gly Cys Tyr Met Ala Ala Thr Gly Ser
        1170                1175                1180

Asp Tyr Ala Leu Leu Gln Ala Arg Asp Gly Glu Lys Gln Thr Pro Tyr
1185                1190                1195                1200

Ser Leu Ser Gly His Ser Leu Ser Ile Leu Ala Asn Arg Ile Ser Ser
            1205                1210                1215

Phe Phe Asp Trp Asn Gly Pro Ser Phe Thr Leu Asp Thr Ala Cys Ser
            1220                1225                1230

Gly Ala Leu Thr Ala Leu Val Lys Ala Cys Arg Asp Leu Gln Ala Gln
        1235                1240                1245

Val Cys Asp Ala Ala Met Val Gly Gly Val Asn Leu Ile Leu Asp Ala
    1250                1255                1260

Gln Ile Asn Glu Gly Leu Glu Ala Gly Arg Phe Met Ser Pro Asp Ser
1265                1270                1275                1280

Arg Cys Ala Thr Phe Asp Ala Ser Ala Asn Gly Tyr Val Arg Gly Glu
            1285                1290                1295

Gly Val Gly Cys Phe Leu Val Lys Arg Leu Gln Asp Ala Gln Ala Asp
        1300                1305                1310

Gly Asp Leu Ile Leu Ala Val Ile Glu Ser Val Ala Glu Asn His Gly
        1315                1320                1325

Gly Lys Ala Asn Ser Leu Thr Ala Pro Asn Pro Asn Ala Gln Tyr Arg
    1330                1335                1340

Leu Leu Leu Asp Ala Tyr Thr Pro Glu Leu Ala Gln Arg Leu Ser Tyr
1345                1350                1355                1360

Ile Glu Thr His Gly Thr Gly Thr Arg Leu Gly Asp Pro Ile Glu Val
            1365                1370                1375

Ala Ala Leu Lys Arg Ala Leu Gln Glu Leu Thr Gly Gly Asn Ala Ala
            1380                1385                1390

Gln Thr Val Trp Leu Gly Ala Val Lys Ser Asn Ile Gly His Leu Glu
        1395                1400                1405
```

```
Pro Ala Ala Gly Val Ala Ser Val Val Lys Val Ile Lys Ala Phe Glu
    1410                1415                1420

His Gln Arg Leu Pro Ala Asn Val His Phe Gln Gln Leu Asn Pro Glu
1425                1430                1435                1440

Ile Asp Leu Ser Ser Ser Pro Phe Gln Val Leu Ala Asp Ser Ile Pro
                1445                1450                1455

Trp Arg Ser Glu Gln Pro Leu Thr Ala Gly Val Ser Ser Phe Gly Phe
            1460                1465                1470

Gly Gly Ala Asn Ala His Val Leu Ser Ala Pro Pro Arg Gln Glu
    1475                1480                1485

Arg Pro Ala Ala Asn His Tyr Asp Thr Tyr Leu Ile Pro Ile Ser Ala
    1490                1495                1500

Arg Ser Glu Ser Ala Leu Gln Lys Asn Met Ala Thr Leu Ala Arg Phe
1505                1510                1515                1520

Val Ala Glu Arg Arg Ala Glu Leu Thr Met Arg Gly Leu Thr Asp Leu
                1525                1530                1535

Ala Phe Ser Leu Ser Cys Gly Arg Glu His Phe Glu Tyr Arg His Ala
                1540                1545                1550

Trp Leu Val Ser Gly Val Asp Glu Leu Leu Met Gln Leu Arg Ser Gly
    1555                1560                1565

His Ala Gly Val His Ala Pro Arg His Ser Pro Ser Ala Asn Glu Gln
    1570                1575                1580

Thr Ala Glu Gly Gln Ala Leu His Glu Thr Met Asp Pro Gly Gly Leu
1585                1590                1595                1600

Asn Asp Pro Ala Ile Leu Ala His Ala Arg Ala Arg Tyr Leu Lys Gly
                1605                1610                1615

Leu Gln Val Asp Trp Thr Arg Leu Tyr Glu Gly Ala Asp Ala Val Lys
                1620                1625                1630

Met Arg Leu Pro Thr Tyr Gln Phe Asp Glu Arg Asp Tyr Trp Tyr Thr
                1635                1640                1645

Lys Ser Leu Thr Gly Gly Tyr Ala Lys Asn Gln Thr Gly Leu Ala Gln
    1650                1655                1660

Met Lys Thr Thr Ala Lys Asp Gly Glu Thr Asp Asp Glu His Lys Arg
1665                1670                1675                1680

<210> SEQ ID NO 14
<211> LENGTH: 254
<212> TYPE: PRT
<213> ORGANISM: Hahella chejuensis

<400> SEQUENCE: 14

Met His Ile Gly Pro Lys Phe Leu Leu Ala Ala Ile Arg Arg Arg Ile
1               5                   10                  15

Lys Asp Glu Gly Leu Ser Tyr Gly Tyr Leu Ser Glu Lys Thr Gly Ile
            20                  25                  30

Pro Leu Ser Ser Ile Lys Arg His Leu His Asn Pro Ser Leu Gly Leu
        35                  40                  45

Asp Lys Ile Leu Met Tyr Val Ser Phe Leu Asn Thr Asp Leu Val Glu
    50                  55                  60

Leu Thr Lys Leu Ala Asn Lys Leu Gln His Glu Asn Glu Leu Phe Ile
65                  70                  75                  80

Ser Asp Lys Gln Ser Glu Leu Phe Leu Glu His Pro Tyr Leu Leu Asp
                85                  90                  95

Phe Ile Asn Met Val Thr Ser His Asn Met Thr Pro Asp Ala Val Ala
                100                 105                 110
```

```
Glu Lys Tyr Gly Leu Ser Glu Thr Ser Leu Arg Phe Tyr Leu Arg Ile
            115                 120                 125

Ala Glu Ile Leu Gly Tyr Ile Asp Asp Phe Gly Asp Gly Ser Phe Tyr
    130                 135                 140

Gln Ser Gly Arg Arg Tyr Leu Leu Glu Glu Gly Ser Ala Leu Asp Ser
145                 150                 155                 160

Leu Phe Arg Arg Arg Phe Gln Glu Glu Ser Leu Ser His Pro Ile His
                165                 170                 175

Pro Gly Val Cys Val Gly Arg Ile Arg Met Thr Glu Ala Gln Arg Ile
                180                 185                 190

Gln Leu Glu Asp Asp Leu Tyr Asp Lys Leu Ile Glu Leu Asn Ala Val
            195                 200                 205

Asn Ser Ser Asn Asp Glu Gly Glu Pro Thr Asn Val Leu Met Arg Cys
210                 215                 220

Thr Pro Gly Lys Leu Thr Gln Phe Ser Asp Gly Leu Pro Asp Ile Asp
225                 230                 235                 240

Gly Gln Leu Leu Lys Tyr Val Ser Glu Leu Phe Ala Lys Ala
                245                 250

<210> SEQ ID NO 15
<211> LENGTH: 209
<212> TYPE: PRT
<213> ORGANISM: Hahella chejuensis

<400> SEQUENCE: 15

Met Phe Asp Ile Asp Gly Thr Leu Val Glu Ser Tyr Asp Phe Asp Thr
1               5                   10                  15

Glu Cys Phe Gln Ala Ala Val Lys Asp Val Val Gly Ile Ser Val Gly
            20                  25                  30

Pro Asp Trp Gly Arg Phe Arg His Val Thr Asp Ala Gly Ile Leu Ser
        35                  40                  45

Glu Ile Ile Glu Glu Val Gly Leu Gln Arg Glu Arg Glu Arg Ile Phe
    50                  55                  60

Phe Asp Val Lys Ala Gln Phe Val Arg Arg Val Glu Glu Tyr Ile Ser
65                  70                  75                  80

Arg His Glu Leu Ser Pro Ile Cys Gly Ala Val Glu Phe Leu Ser Arg
                85                  90                  95

Leu Val Lys Arg Gln Asp Val Ala Ile Ala Phe Ala Thr Gly Gly Trp
            100                 105                 110

Ala Glu Thr Ala Arg Met Lys Leu Asp Ala Val Gly Ile Ser Leu Pro
        115                 120                 125

Gly Ile Ala Met Ala Ser Ser Ser Asp His Tyr Ser Arg Thr Glu Ile
    130                 135                 140

Met Arg Val Ala Glu Met Arg Ala Ser Thr Gly Ser Tyr Asp Ser Lys
145                 150                 155                 160

Thr Tyr Phe Gly Asp Gly Pro Trp Asp Trp Arg Ala Ser Glu Ala Leu
                165                 170                 175

Gly Tyr Asn Phe Ile Ser Val Gly Ser Arg Ile His Ala Ala Gln Ser
            180                 185                 190

Ile Gly Asp Tyr Thr Glu Ser Asp Lys Ala Phe Arg Phe Ile Gly Leu
        195                 200                 205

Lys

<210> SEQ ID NO 16
```

```
<211> LENGTH: 147
<212> TYPE: PRT
<213> ORGANISM: Hahella chejuensis

<400> SEQUENCE: 16

Met Ser Val Asn Gln Gln Ile Leu Ser Ser Tyr Ala Asn Ser Glu Gln
 1               5                  10                  15

Lys Leu Val Asp Val Val Gly Tyr Phe Glu Asn Cys Glu Glu Ser Ser
                20                  25                  30

Leu Glu Cys Val Leu Cys Ala Met Glu Phe Ile Phe Glu Lys Ser Lys
             35                  40                  45

Phe Tyr Ile Val Val Gln Glu Asp Asp Ser Phe Val Leu Tyr Pro Asn
 50                  55                  60

Asp Trp Cys Gly Ala Pro Lys Trp Lys Ser Ile Ser Phe Met Lys Arg
 65                  70                  75                  80

Arg Pro Trp Ser Leu Ala Ile Gly Ser Pro Leu Leu Trp Ser Trp Val
                 85                  90                  95

Leu His Asn Gln Gln Gly Tyr Phe Asp Gly Ile Gln Leu Glu Phe Ala
            100                 105                 110

Lys Ser Thr Glu Ser Arg Ser Val Ile Val Gln Leu Val Ala Leu Gly
            115                 120                 125

Ser Glu Ile Lys Gln Arg Asp Ile Ala Glu Lys Cys Ser Ala Ile Thr
130                 135                 140

Phe Thr Gln
145

<210> SEQ ID NO 17
<211> LENGTH: 158
<212> TYPE: PRT
<213> ORGANISM: Hahella chejuensis

<400> SEQUENCE: 17

Met Asn His Ala Glu Leu Ile Glu Lys Leu Glu Lys Ser Gly Phe Glu
 1               5                  10                  15

Gln Leu Gly Thr Ala Ser Ala Phe Gly Asn Ala Gly Glu Trp Val Ile
                20                  25                  30

Gly Leu Ile Gly Leu Ser Gly Arg Phe Gln Gln Ala Gly Thr Lys Ala
             35                  40                  45

Phe Val Ile Cys Ala Arg Pro Ile Ser Phe Asp Tyr Met Glu Arg Pro
 50                  55                  60

Lys Gly Lys Phe His Cys Asp Pro Met Glu Tyr Pro Phe Lys Leu Thr
 65                  70                  75                  80

Leu Asn Ser Phe Gly Glu Lys Leu Lys Tyr Gln Ser Gln Leu Leu His
                 85                  90                  95

Phe Glu His Ser Arg Met Asp Thr Glu Gly Asp Trp Ser Lys Val Phe
            100                 105                 110

Asp Phe Leu Val Ser Asp Leu Pro Glu Ser Leu Ser Ser Leu Gly Val
            115                 120                 125

Ser Gly Leu Val Gln Gln Leu Lys Ala Ile Arg Glu Pro Gly Tyr Ile
130                 135                 140

Glu Lys Ile Trp Leu Gly Glu Leu Gly Ala Lys Ala Thr Asp
145                 150                 155

<210> SEQ ID NO 18
<211> LENGTH: 126
<212> TYPE: PRT
<213> ORGANISM: Hahella chejuensis
```

<400> SEQUENCE: 18

| | | | | | | | | | | | | | | |
|---|---|---|---|---|---|---|---|---|---|---|---|---|---|---|
|Met|Gly|Ala|Cys|Val|Phe|Ala|Phe|Ile|Glu|Ile|Asn|His|Asn|Asp|Glu
|1| | | |5| | | | |10| | | | |15

Trp Ile Ile Ala Asp Asp Leu Val Glu Asp Glu Asp Tyr Glu Gly Lys
                20                25                30

Pro Val Pro Lys Asn Val Ala Pro Tyr Trp Trp Gly Lys Ser Ala Tyr
        35                40                45

Ala Asp Ile Tyr Glu Leu Ser Gly Glu Arg Gly Phe Pro Ala Asp Leu
    50                55                60

Gly Ala Glu Met Leu Ser Phe Ile Lys Glu Tyr Trp Gln Asp Ala Asn
65                70                75              80

Arg Pro Ser Trp Leu Leu Val Ser Glu Leu Lys His Leu Gln Glu Asp
                85                90              95

Ala Asn Gly Arg Cys Pro Ala Ile Asp Leu Thr Leu Phe Pro Asp Ala
           100              105             110

Leu Pro Asp Ser Glu Val Arg Leu Val Phe Trp Ala Asp Gln
          115              120            125

<210> SEQ ID NO 19
<211> LENGTH: 538
<212> TYPE: PRT
<213> ORGANISM: Hahella chejuensis

<400> SEQUENCE: 19

Met Lys Ile Ser Lys Leu Leu Met Leu Gly Ala Ile Ser Leu Ile Ser
1                5                10              15

Ser Val Phe Thr Val Ser Ala Val Ala Lys Pro Tyr Pro Pro Gly Thr
                20                25              30

Gln Leu Ala Ala Arg Gln Glu Ile Thr Leu Asn Asn Gly Gly Glu Val
        35                40                45

Thr Ser Val Asp Pro Ala Lys Tyr Ala Ala Glu Pro Ala Phe Asn Leu
    50                55                60

Gly Arg Asp Leu Phe Glu Gly Leu Ala Ile Gln Asp Lys Thr Gly Lys
65                70                75              80

Thr Ile Pro Gly Val Ala Glu Ser Trp Ser Val Asn Asp Asn Thr
                85                90              95

Val Tyr Thr Phe Lys Leu Arg Arg Ser Gln Trp Ser Asn Gly Asp Pro
           100              105             110

Val Thr Ala His Asp Phe Val Tyr Ser Trp Arg Arg Leu Leu Asp Pro
           115             120             125

Lys Thr Ala Ser Pro Tyr Ala Trp Phe Ala Ala Met Pro Lys Ile Arg
        130              135             140

Asn Ser Ala Lys Ile Met Lys Gly Glu Ala Asp Pro Ala Thr Leu Gly
145              150              155            160

Val Arg Ala Val Asp Asp Tyr Thr Phe Glu Val Thr Leu Glu Gln Ser
           165             170             175

Val Pro Phe Phe Leu Lys Leu Ile Ser His Pro Val Leu Val Pro Leu
        180              185             190

His Glu Ala Thr Val Glu Lys His Gly Ala Ala Trp Thr Gln Pro Ala
           195             200             205

Asn Ile Val Thr Asn Gly Ala Phe Ile Val Ser Glu Trp Lys Val Asn
        210              215             220

Glu Lys Met Val Leu Lys Lys Asn Pro His Tyr Trp Asp Ala Asp Asn
225              230              235            240

```
Val Val Leu Glu Lys Ile Thr Trp Leu Pro Ile Gly Asp Ala Asn Val
                245                 250                 255

Ala Leu Asn Arg Tyr Leu Ala Gly Glu Ile Asp Gln Ala Leu Ser Ile
                260                 265                 270

Pro Ser Ala Gln Lys Lys Gln Leu Leu Lys Lys Phe Pro Glu Glu Val
                275                 280                 285

Ala Asn Thr Ser Ala Ser Leu Gly Ser Val Tyr Tyr Tyr Met Asn Thr
            290                 295                 300

Val Ala Gly Pro Thr Lys Asp Val Arg Val Arg Thr Ala Leu Ser Tyr
305                 310                 315                 320

Ala Val Asp Arg Asp Ile Met Thr Lys Ala Ile Leu Asn Asn Gly Gly
                325                 330                 335

Val Pro Met Tyr Thr Leu Val Pro Pro Gln Thr Asp Gly Tyr Lys Pro
                340                 345                 350

Tyr Thr Pro Glu Tyr Ala Thr Trp Thr Gln Lys Gln Arg Asn Glu Lys
                355                 360                 365

Ala Lys Gln Leu Leu Thr Glu Ala Gly Tyr Ser Lys Asp Lys Pro Leu
                370                 375                 380

Lys Leu Thr Phe Thr Val Pro Thr Phe Ser Thr Asp Val Lys Ile Ala
385                 390                 395                 400

Thr Ala Met Ala Gly Met Trp Lys Ser Val Leu Gly Val Gln Val Glu
                405                 410                 415

Ile Lys Gln Leu Glu Pro Lys Val Phe Tyr Ala Leu Lys Glu Thr Gly
                420                 425                 430

Asp Ile His Arg Gly Gly Trp Val Ala Asp Tyr Asn Glu Ala Ser Ser
                435                 440                 445

Trp Leu Asp Val Phe Val Ser Ser Gly Glu Phe Asn Asp Ser Lys Tyr
                450                 455                 460

Ser Asn Pro Arg Tyr Asp Gln Leu Met Gln Ala Ser Lys Val Leu Ser
465                 470                 475                 480

Asp Pro Ser Lys Glu Tyr Arg Glu Ala Glu Thr Leu Leu Ile Asn Asp
                485                 490                 495

Met Ala Ile Ile Pro Val Tyr Arg Tyr Gly Asn Asp Gln Tyr Leu Ile
                500                 505                 510

Lys Pro Tyr Ile Gly Gly Tyr Glu Arg Thr Asn Pro Glu Ala Ser Tyr
                515                 520                 525

Tyr Arg Lys Asn Val Tyr Val Lys Ala His
            530                 535

<210> SEQ ID NO 20
<211> LENGTH: 306
<212> TYPE: PRT
<213> ORGANISM: Hahella chejuensis

<400> SEQUENCE: 20

Met Leu Leu Tyr Ile Leu Arg Arg Leu Leu Ile Ala Ile Pro Thr Leu
 1               5                  10                  15

Leu Phe Ile Ala Leu Val Ser Phe Trp Leu Met His Val Ala Pro Gly
                20                  25                  30

Gly Pro Phe Asp Met Glu Arg Pro Met Pro Glu Ile Val Arg Ala Asn
                35                  40                  45

Ile Glu Ala Lys Tyr His Leu Asn Glu Pro Phe Phe Thr Gln Phe Phe
            50                  55                  60

Ile Tyr Ile Arg Asp Phe Val Gln Gly Asp Leu Gly Pro Ser Phe Val
```

```
                65                  70                  75                  80
Tyr Gln Asp Phe Thr Val Thr Gln Leu Val Gly Gln Ser Trp Pro Val
                    85                  90                  95

Ser Ala Thr Leu Gly Val Leu Ser Phe Cys Ile Ser Val Pro Val Gly
                    100                 105                 110

Leu Leu Leu Gly Thr Leu Ala Ala Phe Asn Arg Asn Ser Lys Leu Asp
                    115                 120                 125

Tyr Phe Leu Met Ser Leu Ser Met Thr Gly Val Val Ile Pro Ala Phe
                130                 135                 140

Val Leu Ala Pro Val Leu Val Ala Ile Phe Ala Ile Arg Leu Asp Trp
145                 150                 155                 160

Leu Pro Ala Gly Gly Trp Glu Gly Gly Lys Ala Ala Phe Leu Ile Leu
                    165                 170                 175

Pro Val Leu Ser Leu Ala Ile Gly Ser Val Ala Ser Ile Ala Arg Val
                    180                 185                 190

Met Arg Gly Ala Met Ile Glu Thr Leu Asn Gln Pro Tyr Ile Arg Thr
                    195                 200                 205

Ala Ile Ala Lys Gly Leu Ser Thr Pro Tyr Leu Leu Phe His His Ala
                    210                 215                 220

Leu Arg Pro Ser Leu Ile Pro Val Val Ala Met Leu Gly Pro Ala Phe
225                 230                 235                 240

Val Ala Val Val Thr Gly Ser Val Ile Asp Ile Phe Phe Gly Thr
                    245                 250                 255

Gly Gly Met Gly Gln His Phe Val Ser Gly Ala Leu Asn Arg Asp Tyr
                    260                 265                 270

Gly Leu Val Met Gly Ile Thr Leu Ile Val Ala Ser Leu Thr Ile Phe
                    275                 280                 285

Phe Asn Leu Val Val Asp Leu Leu Tyr Thr Val Ile Asp Pro Arg Ile
                290                 295                 300

Arg Ile
305

<210> SEQ ID NO 21
<211> LENGTH: 277
<212> TYPE: PRT
<213> ORGANISM: Hahella chejuensis

<400> SEQUENCE: 21

Met Arg Phe Arg Lys Asn Arg Ala Ala Met Thr Ser Val Tyr Val Leu
 1                5                  10                  15

Leu Phe Ile Val Val Cys Ile Val Val Gly Pro His Val Ala Pro Phe
                    20                  25                  30

Ser His Asp Glu Ile Asp Trp Ser Val Val Ala Asp Pro Tyr Glu Leu
                35                  40                  45

Gly Lys Pro Ser Leu Glu Thr Gly His Tyr Phe Gly Thr Asp Asp Leu
    50                  55                  60

Gly Gln Asp Leu Phe Ala Arg Thr Met Gln Gly Gly Arg Leu Ser Ile
65                  70                  75                  80

Met Val Gly Phe Met Gly Ala Leu Val Ala Val Leu Ile Gly Thr Val
                    85                  90                  95

Trp Gly Ala Ile Ser Gly Tyr Val Gly Gly Leu Val Asp Ser Val Met
                    100                 105                 110

Met Arg Val Ile Glu Val Leu Asp Ser Val Pro Phe Phe Met Val
                    115                 120                 125
```

```
Ile Leu Phe Val Thr Leu Phe Gly Asn Asn Ile Tyr Leu Ile Phe Ile
    130                 135                 140

Val Ile Gly Met Val Ser Trp Leu Asn Ile Ala Arg Val Val Arg Gly
145                 150                 155                 160

Val Thr Phe Ser Ile Lys Arg Arg Glu Phe Ile Glu Ala Ala His Ser
                165                 170                 175

Ile Gly Val Ser Lys Leu Thr Ile Val Arg Arg His Val Leu Pro Asn
            180                 185                 190

Val Leu Gly Ile Val Met Val Tyr Ser Ser Leu Met Val Pro Gly Phe
        195                 200                 205

Ile Met Phe Glu Ser Phe Leu Ser Phe Leu Gly Leu Gly Val Gln Pro
    210                 215                 220

Pro Asp Thr Ser Trp Gly Ile Leu Ile Ala Glu Gly Ala Lys Thr Ile
225                 230                 235                 240

Asp Val Ala Leu Trp Leu Leu Met Phe Pro Ser Leu Phe Leu Val Ala
                245                 250                 255

Thr Leu Phe Cys Phe Asn Phe Ile Gly Asp Gly Leu Arg Asp Ala Leu
            260                 265                 270

Asp Pro Lys Asp Arg
            275

<210> SEQ ID NO 22
<211> LENGTH: 321
<212> TYPE: PRT
<213> ORGANISM: Hahella chejuensis

<400> SEQUENCE: 22

Met Asn Val Arg Phe Glu Thr Pro Asp Gly Leu Val Gln Ala Val Ser
1               5                   10                  15

Asp Leu Ser Phe Thr Val Arg Ala Gly Glu Thr Leu Gly Ile Val Gly
            20                  25                  30

Glu Ser Gly Ser Gly Lys Ser Gln Ser Val Phe Ala Leu Met Gly Leu
        35                  40                  45

Thr Ala Asp Asn Gly Arg Val Ser Gly Val Ala Asn Phe His Gly Glu
    50                  55                  60

Asn Leu Leu Ala Met Ser Lys Arg Gln Leu Asn Arg Ile Arg Ala Glu
65                  70                  75                  80

Lys Ile Gly Met Ile Phe Gln Asp Pro Met Thr Ser Leu His Pro Phe
                85                  90                  95

Leu Lys Ile Asp Lys Gln Leu Thr Glu Val Leu Met Ile His Lys Gly
            100                 105                 110

Met Ser Lys Ala Ala Ala Arg Ala Glu Ser Ile Arg Met Leu Asp Ala
        115                 120                 125

Val Arg Ile Pro Ser Pro Gln Ala Arg Met Gly Gln Tyr Pro His Glu
    130                 135                 140

Leu Ser Gly Gly Met Arg Gln Arg Ile Met Ile Ala Met Ala Leu Leu
145                 150                 155                 160

Cys Arg Pro Glu Leu Leu Ile Ala Asp Glu Pro Thr Thr Ala Leu Asp
                165                 170                 175

Val Thr Val Gln Ala Gln Ile Leu Ser Leu Leu Trp Glu Leu Gln Gly
            180                 185                 190

Glu Phe Asn Thr Ala Ile Leu Leu Ile Thr His Asp Met Gly Val Val
        195                 200                 205

Ala Glu Met Cys Asp Arg Val Leu Val Met Tyr Gly Gly Arg Lys Met
    210                 215                 220
```

-continued

```
Glu Glu Ala Asp Thr Glu Thr Leu Phe Glu Arg Pro Ala His Pro Tyr
225                 230                 235                 240

Thr Gln Gly Leu Leu Lys Ala Ile Pro Ser Ile Thr Glu Asp Met Pro
            245                 250                 255

Arg Leu Pro Thr Ile Pro Gly Asn Pro Asn Ala Leu Ile Asn Asn
        260                 265                 270

Lys Gly Cys Pro Phe Arg Glu Arg Cys Ser Leu Gln Gln Pro Ser Cys
        275                 280                 285

Glu Ala Ala Ile Pro Pro Leu Thr Arg Leu Gly Ala Thr Gln Leu Ala
        290                 295                 300

Ala Cys His Gly Leu Ala Gln Asn Lys Thr Thr Pro Leu Ala Arg Thr
305                 310                 315                 320

Ala

<210> SEQ ID NO 23
<211> LENGTH: 331
<212> TYPE: PRT
<213> ORGANISM: Hahella chejuensis

<400> SEQUENCE: 23

Met Asn Ala Lys Glu Val Leu Leu Ser Ala Arg Asn Leu Glu Val His
1               5                   10                  15

Phe Pro Ile Gly Lys His Ile Leu Pro Ser Arg Pro Arg Leu Lys
            20                  25                  30

Ala Val Asn Gly Ile Asp Val Asp Val Tyr Arg Gly Glu Thr Leu Gly
        35                  40                  45

Ile Val Gly Glu Ser Gly Cys Gly Lys Ser Thr Leu Ala Arg Ala Leu
    50                  55                  60

Leu Arg Leu Ile Glu Pro Thr Arg Gly Glu Leu Arg Trp Lys Gly Glu
65                  70                  75                  80

Asp Leu Arg Gly Phe Asp Lys Thr Thr Leu Val Arg Arg Arg Glu
            85                  90                  95

Phe Gln Met Val Phe Gln Asp Pro Thr Ala Ser Leu Asn Pro Arg Leu
            100                 105                 110

Thr Val Ser Glu Cys Ile Ala Glu Pro Leu Leu Thr His Glu Pro Gly
        115                 120                 125

Leu Lys Arg Lys Asp Ile Glu Arg Arg Val Ile Ala Met Met Asp Lys
130                 135                 140

Val Gly Leu Ser Ala Ser Gln Arg Asn Arg Tyr Pro His Glu Phe Ser
145                 150                 155                 160

Gly Gly Gln Cys Gln Arg Val Gly Ile Ala Arg Ala Leu Ile Leu Asn
            165                 170                 175

Pro Asp Leu Val Val Cys Asp Glu Pro Val Ser Ala Leu Asp Val Ser
        180                 185                 190

Ile Gln Ala Gln Val Ile Asn Leu Leu Asp Asp Leu Lys Gln Glu Met
        195                 200                 205

Gly Leu Thr Leu Val Met Ile Ala His Asp Leu Ser Val Val Arg His
    210                 215                 220

Ile Ser Asp Arg Val Met Val Met Tyr Leu Gly Lys Pro Met Glu Val
225                 230                 235                 240

Gly Leu Tyr Asp Arg Val Phe Asp Gln Ala Gln His Pro Tyr Thr Lys
            245                 250                 255

Ala Leu Leu Ser Ala Val Pro Ile Ala Asn Pro Lys Leu Ala Arg Gln
        260                 265                 270
```

```
Arg Glu Val Gln Leu Leu Pro Gly Asp Leu Pro Ser Pro Leu Asn Pro
        275                 280                 285

Pro Ser Gly Cys Val Phe Arg Thr Arg Cys Pro Glu Ala Thr Asp Leu
    290                 295                 300

Cys Gly Ser Gln Pro Pro Thr Gln Ser Gly Ser Asp Glu His Arg Ile
305                 310                 315                 320

Phe Cys Ser Asn Thr Leu Leu Leu Ala Gly Gln
                325                 330

<210> SEQ ID NO 24
<211> LENGTH: 595
<212> TYPE: PRT
<213> ORGANISM: Hahella chejuensis

<400> SEQUENCE: 24

Met Asn Thr Pro Ser Val Thr Gln Arg Leu Glu His Leu Arg Lys Ala
1               5                   10                  15

Met Asp Lys Gln Ala Phe Ala Ala Tyr Ile Val Thr Asn Asn Asp Pro
            20                  25                  30

His Ser Ser Glu Tyr Ser Ala Asp His Trp Leu Ala Arg Thr Trp Ile
        35                  40                  45

Ser Gly Phe Asn Gly Ser Ala Gly Asn Val Val Val Thr Gly Asp Gly
    50                  55                  60

Gly Gly Leu Trp Thr Asp Gly Arg Tyr Phe Ile Gln Ala Glu Glu Gln
65                  70                  75                  80

Leu Ala Gly Ser Gly Leu Lys Leu Phe Lys Ala Arg Leu Pro Glu Thr
                85                  90                  95

Pro Thr Ile Pro Gln Trp Leu Ala Ala Thr Leu Pro Glu Asn Ala Arg
            100                 105                 110

Val Gly Val Asp Gly Arg Ser Ile Ser Arg Ala Phe Tyr Gln Glu Leu
        115                 120                 125

Leu Asp Ala Phe Ala Pro Lys Ser Ile Gln Leu Ile Leu Asp Gln Asp
    130                 135                 140

Leu Ile Thr Pro Leu Trp Tyr Asp Arg Pro Ala Arg Pro Lys Ala Pro
145                 150                 155                 160

Val Phe Asn His Glu Leu Arg Tyr Ala Gly Val Asp Ala Gln Glu Lys
                165                 170                 175

Met Gln Arg Ile Arg Asp Trp Met Thr Glu Gln Val Asp Gly Leu
            180                 185                 190

Leu Val Ser Thr Leu Asp Asp Val Met Trp Ala Leu Asn Ile Arg Gly
        195                 200                 205

Gly Asp Thr Pro Tyr Cys Pro Ile Ser Glu Ser Tyr Leu Leu Val Thr
    210                 215                 220

Ala Gln Gln Ser Gln Val Phe Met Asp Arg Asp Lys Leu Pro Glu Ala
225                 230                 235                 240

Val Glu Cys Thr Leu Ala Glu Tyr Gly Val Thr Ala His Gly Tyr Glu
                245                 250                 255

Leu Val Val Glu Ala Val Asn Gln Leu Pro Glu Gly Cys Arg Leu Ala
            260                 265                 270

Ile Asn Pro Ala Ser Ala Asn Ser Leu Leu Val Asn Gln Ile Lys Pro
        275                 280                 285

Glu Ile Thr Leu Val Glu Thr Pro Cys Pro Val Thr Asp Met Lys Ala
    290                 295                 300

Gln Lys Asn Pro Thr Glu Met Glu Asn Phe Glu Gln Ala Leu Arg Leu
```

```
            305                 310                 315                 320
Asp Gly Val Ala Met Val Asn Phe Met Tyr Trp Leu Gln Thr Gln Val
                325                 330                 335

Pro Gly Gly Lys Val Thr Glu Leu Ser Ala Glu Ala Gln Leu Arg Ala
                340                 345                 350

Tyr Arg Arg Ala Thr Ser Ser Tyr Ile Ser Asp Ser Phe Arg Thr Ile
                355                 360                 365

Ala Gly Phe Gly Pro His Ala Ala Lys Met His Tyr Ser Ala Ser Thr
                370                 375                 380

Asp Ser Asn Ala Thr Val Asp Glu Ser Asn Phe Phe Leu Val Asp Ser
385                 390                 395                 400

Gly Gly Gln Tyr Pro Gly Gly Thr Thr Asp Ile Thr Arg Thr Phe His
                405                 410                 415

Phe Gly Thr Pro Thr Ala Gln Gln Arg Lys Asp Tyr Thr Leu Val Leu
                420                 425                 430

Lys Ala Val Ile Arg Leu Thr Gln Thr Val Phe Leu Lys Gly Ala Thr
                435                 440                 445

Gly Ala Asn Leu Asp Ile Met Ala Arg Gly Met Leu Trp Arg His Arg
                450                 455                 460

Ile Asp Tyr Lys Cys Gly Thr Gly His Gly Val Gly Leu Cys Leu Asn
465                 470                 475                 480

Val His Glu Gly Pro Gln Asn Phe Ser Gln Asn Pro Lys Glu Val Ala
                485                 490                 495

Leu Lys Pro Gly Met Val Ile Thr Asn Glu Pro Gly Val Tyr Arg Glu
                500                 505                 510

Gly Glu Tyr Gly Val Arg Ile Glu Asn Ile Met Lys Val Val Glu Leu
                515                 520                 525

Glu Glu Asn Glu Phe Gly Val Phe Tyr Gly Phe Glu Thr Ile Thr Leu
                530                 535                 540

Ala Pro Ile Ala Ile Asn Ala Leu Asp Leu Ser Met Leu Ser Thr Glu
545                 550                 555                 560

Glu Thr Asp Trp Leu Asn Ala Tyr His Trp Arg Val Tyr Glu Ala Leu
                565                 570                 575

Ser Pro Tyr Leu Glu Ala Ser Gln Thr Ala Trp Leu Arg Asn Ala Thr
                580                 585                 590

Lys Pro Val
        595

<210> SEQ ID NO 25
<211> LENGTH: 183
<212> TYPE: PRT
<213> ORGANISM: Hahella chejuensis

<400> SEQUENCE: 25

Met Lys Thr Thr Leu Leu Met Phe His Ser Arg Tyr Arg Pro Ser Arg
1               5                   10                  15

Ile Asn Ala Ala Leu Met Ala Ala Gln Thr Leu Asp Asn Leu Asp
                20                  25                  30

Val Val Asp Met Asn Arg Leu Tyr Pro Asp Glu Arg Ile Asp Val Ala
                35                  40                  45

Thr Glu Ile Glu Arg Leu Leu Gln Ser Glu Arg Leu Ile Leu Gln Phe
        50                  55                  60

Pro Ile Gln Trp Tyr Ser Thr Pro Pro Leu Leu Gln Arg Trp Gln Asp
65              70                  75                  80
```

```
Leu Val Leu Thr His Met Tyr Tyr Leu Asp Tyr Glu Asn Thr Gly Arg
                85                  90                  95

Arg Phe Glu Gly Ala Pro Ile Met Val Ala Ala Thr Ala Gly Asn Thr
            100                 105                 110

Glu Ala Ala Tyr Gln Pro Arg Gly Arg Asn Arg Phe Thr Met Glu Thr
        115                 120                 125

Leu Leu Thr Pro Leu Gln Ala Thr Ala Asn Arg Cys Arg Leu Pro Trp
    130                 135                 140

Gly Asp Pro Phe Val Val Tyr Gln Ala Asp Tyr Leu Met Asp Ala Glu
145                 150                 155                 160

Leu Asp Ile Ala Cys Glu Arg Tyr Leu Thr His Ile Gln Asn Trp Arg
                165                 170                 175

Thr Glu Phe Val Arg Gly Gln
            180

<210> SEQ ID NO 26
<211> LENGTH: 297
<212> TYPE: PRT
<213> ORGANISM: Hahella chejuensis

<400> SEQUENCE: 26

Met Asn Leu Arg Gly Val Asp Leu Asn Leu Leu Val Ile Leu Asp Ala
1               5                   10                  15

Leu Met Asp Glu Arg His Val Thr Arg Ala Ala Lys Arg Leu His Leu
            20                  25                  30

Ser Gln Pro Ala Thr Ser Ser Ala Leu Glu Arg Cys Arg His Leu Phe
        35                  40                  45

Gly Asp Pro Leu Leu Ile Arg Gly Arg Gly Glu Met Arg Leu Ser Ala
    50                  55                  60

Lys Ala Glu Ser Leu Arg Glu Pro Val Lys Ala Leu Leu Ala Gln Ala
65                  70                  75                  80

Glu Arg Val Ile Asn Gln Ala Asp Thr Pro Leu Ala Glu Leu Arg Gln
                85                  90                  95

Thr Leu Arg Ile Leu Met Ala Asp Phe Pro Val Ser Ala Leu Leu Gly
            100                 105                 110

Pro Leu His Gln Arg Leu Met Thr Ser Ala Pro Asn Leu Asp Leu Ile
        115                 120                 125

Ile Gln Thr Trp His Gly Ala Lys Ser Ala Leu Glu Gln Leu Ala Lys
    130                 135                 140

Gly Glu Ala Asp Leu Ala Val Ser Val Phe Pro Asn Val Gly Ala Ser
145                 150                 155                 160

Phe Arg Cys Val Glu Leu Leu Tyr Glu Asp Tyr Cys Val Leu Met Arg
                165                 170                 175

Lys Asp His Pro Ala Ala Gln Asp Phe Asn Leu Gln Gln Trp Leu Ala
            180                 185                 190

Tyr Pro His Val Leu Val Ser Gly Arg Gly Asp Thr Asp Ser Pro Val
        195                 200                 205

Asp Gln Thr Leu Gln Ala His Gly Leu Arg Arg Val Gly Leu Val
    210                 215                 220

Val Pro Tyr Phe Gln Met Ala Pro Asp Leu Val Ala Gln Ser Asp Tyr
225                 230                 235                 240

Ile Ala Leu Leu Pro Ile His Cys Val Pro Gln Asp Thr Thr Lys Phe
                245                 250                 255

Thr Val Phe Pro Pro Ile Pro Val Glu Gly Phe Pro Leu His Leu
            260                 265                 270
```

```
Ala Trp His Val Arg Arg Gln Gly Asp Gln Ala Val Ser His Val Val
        275                 280                 285
Glu Val Ile Arg Glu Val Thr Gly Phe
    290                 295
```

<210> SEQ ID NO 27
<211> LENGTH: 359
<212> TYPE: PRT
<213> ORGANISM: Hahella chejuensis

<400> SEQUENCE: 27

```
Met Glu Asp Ile Met Lys Lys Glu Leu Arg His Arg Glu Val Ala Leu
  1               5                  10                  15
Tyr Lys Tyr Asn Lys Ile Arg Tyr Ser Phe Val Pro Leu Ser Val Gly
                 20                  25                  30
Glu Leu Pro Ile Leu Thr Ser Asp Pro Trp Ser Phe Leu Ser Ser Lys
             35                  40                  45
Leu Gln Ile Leu Pro Lys Lys Arg Gly Asn Asn Arg Leu Lys Ile
     50                  55                  60
Glu Arg Ala Ile Tyr Tyr Ser Gly Leu Ala Glu Asp Phe Tyr Arg Ala
 65                  70                  75                  80
Ala Asn Ser Val Pro Leu Pro Ala Lys Ser Ala Leu Leu Tyr Tyr Gly
                 85                  90                  95
Met Leu Asp Leu Val Lys Cys Tyr Leu Ser Leu His Asp Val Pro Leu
                100                 105                 110
Glu Ser Ser His Glu His His Gly Leu Ile Leu Pro Ile Lys Asn Glu
            115                 120                 125
Gln Val Val Glu Val Lys Gly Lys Met Lys Gly Val Val Asn Ile Phe
        130                 135                 140
Leu Glu Phe Ser Cys Leu Leu Gly Lys Asn Ile Asp Arg Val His Arg
145                 150                 155                 160
Ile Lys Phe Asn Gln Ala Leu Ser His Val Pro Glu Ile His Ser Ile
                165                 170                 175
Tyr Thr Ser Leu Gly His Ile Asn Lys Arg Lys Leu Leu Pro Val Asp
            180                 185                 190
Ile Glu Phe Leu Ile Thr Gln Lys Lys Asp Lys Leu Tyr Thr Glu Ile
        195                 200                 205
Ser Tyr Lys Lys Glu Gln Glu Lys Val Asn Ile Glu Lys Phe Leu
    210                 215                 220
Thr Gly Glu Arg Arg Lys Tyr Phe Lys Lys Ile Lys Ala Asp Asn Glu
225                 230                 235                 240
Lys Ile Ile Tyr His Ser Arg Gln Lys Lys Ile Thr Arg Glu Asn Ile
                245                 250                 255
His Ile Ile Tyr Lys Asn Thr Leu Asn Glu Tyr Lys Lys Leu Glu Ile
            260                 265                 270
Val Pro Ile Leu Thr Arg Gln Gly Tyr Arg Tyr Val Asp Leu Ile
        275                 280                 285
Pro Gly Tyr Leu Pro His Leu Ser Tyr Thr Leu Leu Ala Met Phe Tyr
    290                 295                 300
Leu Gly Gly Ala Ala Arg Tyr Arg Pro Leu Glu Ile Lys Ser Leu Leu
305                 310                 315                 320
Met Gly Glu Leu Arg Pro Leu Val Ser Glu Phe Val Ser Leu Ser Pro
                325                 330                 335
Lys Gln Phe Leu Tyr Gln Met Val Ser Leu Ile Thr Ser Lys Glu Cys
```

Leu Ile Pro Phe Ala Ser Ile
       355

<210> SEQ ID NO 28
<211> LENGTH: 62
<212> TYPE: DNA
<213> ORGANISM: Artificial Sequence
<220> FEATURE:
<223> OTHER INFORMATION: PCR PRIMER

<400> SEQUENCE: 28
cacaaattca tcaaggactt aatggtttaa aggagtcgaa tgattccggg gatccgtcga     60
cc                                                                   62

<210> SEQ ID NO 29
<211> LENGTH: 58
<212> TYPE: DNA
<213> ORGANISM: Artificial Sequence
<220> FEATURE:
<223> OTHER INFORMATION: PCR PRIMER

<400> SEQUENCE: 29
tgctccggga gggattgcgc ctgcgctcag acagggtcat gtaggctgga gctgcttc      58

<210> SEQ ID NO 30
<211> LENGTH: 62
<212> TYPE: DNA
<213> ORGANISM: Artificial Sequence
<220> FEATURE:
<223> OTHER INFORMATION: PCR PRIMER

<400> SEQUENCE: 30
cacgcacagg cttaacccat agaggtaatc aaaatgaaaa tgattccggg gatccgtcga     60
cc                                                                   62

<210> SEQ ID NO 31
<211> LENGTH: 61
<212> TYPE: DNA
<213> ORGANISM: Artificial Sequence
<220> FEATURE:
<223> OTHER INFORMATION: PCR PRIMER

<400> SEQUENCE: 31 cgcttttttct ttttgtagca acattgttcg actcctttat catgtaggct ggagctgctt   60
c                                                                    61

<210> SEQ ID NO 32
<211> LENGTH: 59
<212> TYPE: DNA
<213> ORGANISM: Artificial Sequence
<220> FEATURE:
<223> OTHER INFORMATION: PCR PRIMER

<400> SEQUENCE: 32
agcatcctaa caacaaaaat cacggagtct ggcgagatga ttccggggat ccgtcgacc      59

<210> SEQ ID NO 33
<211> LENGTH: 61
<212> TYPE: DNA
<213> ORGANISM: Artificial Sequence
<220> FEATURE:
<223> OTHER INFORMATION: PCR PRIMER

<400> SEQUENCE: 33
tccctgcacg atcacgccaa atcatcccca ctaagccttt catgtaggct ggagctgctt    60
c                                                                    61

<210> SEQ ID NO 34
<211> LENGTH: 61
<212> TYPE: DNA
<213> ORGANISM: Artificial Sequence
<220> FEATURE:
<223> OTHER INFORMATION: PCR PRIMER

<400> SEQUENCE: 34
ggggagagga cgtgcatcta gtcatgtttg acatagacat gattccgggg atccgtcgac    60
c                                                                    61

<210> SEQ ID NO 35
<211> LENGTH: 59
<212> TYPE: DNA
<213> ORGANISM: Artificial Sequence
<220> FEATURE:
<223> OTHER INFORMATION: PCR PRIMER

<400> SEQUENCE: 35
ttattttaat ccaataaacc taaaggcctt atcagattca tgtaggctgg agctgcttc     59

<210> SEQ ID NO 36
<211> LENGTH: 59
<212> TYPE: DNA
<213> ORGANISM: Artificial Sequence
<220> FEATURE:
<223> OTHER INFORMATION: PCR PRIMER

<400> SEQUENCE: 36
acgcactgaa aaccgaactg aaaaggaccg cccgacatga ttccggggat ccgtcgacc     59

<210> SEQ ID NO 37
<211> LENGTH: 58
<212> TYPE: DNA
<213> ORGANISM: Artificial Sequence
<220> FEATURE:
<223> OTHER INFORMATION: PCR PRIMER

<400> SEQUENCE: 37
gataacgctc acaggcgata tccagttccg catccatcat gtaggctgga gctgcttc      58

<210> SEQ ID NO 38
<211> LENGTH: 62
<212> TYPE: DNA
<213> ORGANISM: Artificial Sequence
<220> FEATURE:
<223> OTHER INFORMATION: PCR PRIMER

<400> SEQUENCE: 38
tgttgctgtg tctgggcggt ctggcgatga gctatgtcta tgattccggg gatccgtcga    60
cc                                                                   62

<210> SEQ ID NO 39
<211> LENGTH: 61
<212> TYPE: DNA
<213> ORGANISM: Artificial Sequence
<220> FEATURE:
<223> OTHER INFORMATION: PCR PRIMER

<400> SEQUENCE: 39

-continued

```
accgcaaacg ggacagcgtt gtttattttg ctaatccgct catgtaggct ggagctgctt    60
c                                                                    61

<210> SEQ ID NO 40
<211> LENGTH: 62
<212> TYPE: DNA
<213> ORGANISM: Artificial Sequence
<220> FEATURE:
<223> OTHER INFORMATION: PCR PRIMER

<400> SEQUENCE: 40
tgttgctgtg tctgggcggt ctggcgatga gctatgtcta tgattccggg gatccgtcga    60
cc                                                                   62

<210> SEQ ID NO 41
<211> LENGTH: 61
<212> TYPE: DNA
<213> ORGANISM: Artificial Sequence
<220> FEATURE:
<223> OTHER INFORMATION: PCR PRIMER

<400> SEQUENCE: 41
accgcaaacg ggacagcgtt gtttattttg ctaatccgct catgtaggct ggagctgctt    60
c                                                                    61

<210> SEQ ID NO 42
<211> LENGTH: 62
<212> TYPE: DNA
<213> ORGANISM: Artificial Sequence
<220> FEATURE:
<223> OTHER INFORMATION: PCR PRIMER

<400> SEQUENCE: 42
tgcactgtgg aagactataa aatgaacttg ggtgaaacga tgattccggg gatccgtcga    60
cc                                                                   62

<210> SEQ ID NO 43
<211> LENGTH: 61
<212> TYPE: DNA
<213> ORGANISM: Artificial Sequence
<220> FEATURE:
<223> OTHER INFORMATION: PCR PRIMER

<400> SEQUENCE: 43
tccggcgcat aagaaagact agcggtcgct aatcagatat catgtaggct ggagctgctt    60
c                                                                    61
```